United States Patent [19]
Entian et al.

[11] Patent Number: 5,837,485
[45] Date of Patent: Nov. 17, 1998

[54] DNA ENCODING AND BIOSYNTHETIC PROCESS FOR THE PREPARATION OF CHEMICAL COMPOUNDS, LANTIBIOTICS

[75] Inventors: Karl-Dieter Entian, Oberursel, Germany; Friedrich Götz, Tübingen, Germany; Norbert Schnell, Pasadena, Calif.; Johannes Augustin, Tübingen, Germany; Germar Engelke, Frankfurt am Main, Germany; Ralf Rosenstein, Reutlingen, Germany; Cortina Kaletta, Münich, Germany; Cora Klein, Offenbach, Germany; Bernd Wieland, Rottenburg, Germany; Thomas Kupke; Günther Jung, both of Tübingen, Germany; Roland Kellner, Heppenheim, Germany

[73] Assignee: Dr. Karl Tomae GmbH, Biberach an der Riss, Germany

[21] Appl. No.: 392,625

[22] Filed: Feb. 22, 1995

Related U.S. Application Data

[63] Continuation of Ser. No. 876,791, Apr. 30, 1992, abandoned, which is a continuation of Ser. No. 784,234, Oct. 31, 1991, abandoned, which is a continuation-in-part of Ser. No. 353,590, May 18, 1989, abandoned.

[30] Foreign Application Priority Data

May 18, 1988 [GB] United Kingdom ............... 88 11761.9

[51] Int. Cl.$^6$ .............................. C12N 15/52; C12N 15/63
[52] U.S. Cl. .................... 435/69.1; 435/320.1; 536/23.1; 536/23.2
[58] Field of Search .............................. 435/252.1, 252.3, 435/252.31, 252.33, 252.35, 252.5, 885, 886, 882, 884, 839, 908, 69.1, 69.4, 69.7, 71.3, 320.1; 536/23.1, 23.2, 23.4

[56] References Cited

U.S. PATENT DOCUMENTS 4,716,115 12/1987 Gonzalez et al. ..................... 435/172.3
5,231,013 7/1993 Jung et al. .............................. 435/71.3

FOREIGN PATENT DOCUMENTS 0 342 658 11/1989 European Pat. Off. .

OTHER PUBLICATIONS

Allgaier, H. et al., *Eur. J. Biochem.*, 160(1): Sep. 22, 1986.
Kupke, T. et al., *J. Bacteriology*, 174 (16) : 5354–61, Aug. 1992.
Kaletta, C. et al., *J. Bacteriology*, 171 (3):1597–1601, Mar. 1989.
Kaletta. C. et al., *DECHEMA Biotechnolog. Conf.*(3, Part A, pp. 33–35) May 1989.
Jung, G., *Angew. Chem. Int. Ed. Eng.*, 30(9):1051–1068, Sep. 1991.
Augustin et al., "Identification of epidermin biosynthetic genes by complementation studies and heterologous expression," *Proceedings of the 1st International Workshop on Lantibiotics. Nisin Novel Lantibiotics* 1991, pp. 277–286.

Schnell et al., "the operon–like organisation of lantibiotic epidermin biosynthesis genes," *Proceedings of the 1st International Workshop on Lantibiotics. Nisin Novel Lantibiotics* 1991, pp. 269–276.
Klein et al., Analysis of Genes Involved in Biosynthesis of the Lantibiotic Subtilin, *Applied and Environmental Microbiology* 58(1):132–142 (1992).
Augustin et al., Genetic analysis of epidermin biosynthetic genes and epidermin–negative mutants of *Staphylococcus epidermidis*, *Eur. J. Biochem.* 204 :1149–1154 (1992).
Banerjee et al., Structure and Expression of a Gene Encoding the Precursor of Subtilin, a Small Protein Antibiotic, *Journal of Biological Chemistry* 263(19):9508–9514 (1988).
Buchman et al., Structure, Expression, and Evolution of a Gene Encoding the Precursor of Nisin, a Small Protein Antibiotic, *Journal of Biological Chemistry* 263(31):16260–16266 (1988).
Entian et al., Structure and DNA–Sequence analysis of the staphylococcal lantibiotics epidermin and gallidermin, *Abstr. Annual Meeting American Society for Microbiology* 89(0):182 abstr. H–78 (1989).
Fiedler et al., Purification of the hydrophilic antibiotics epidermin, gallidermin, and nikkomycin Z by preparative reversed–phase HPLC, *Chem. Abstr.* 110:583, Abstr. No. 210845v (1989).
Fiedler et al., Purification of the Hydrophilic Antibiotics Epidermin, Gallidermin, and Nikkomycin Z by Preparative Reversed–Phase HPLC, *Chromatographia* 26:215–220 (1988).
Gennaro et al., A Site–Specific Recombination Function in *Staphylococcus aureus* Plasmids, *Journal of Bacteriology* 169(6):2601–2610 (1987).
Horinouchi et al., Nucleotide Sequence and Functional Map of pC194, a Plasmid That Specifies Inducible Chloramphenicol Resistance, *Journal of Bacteriology* 150(2):815–825 (1982).
Kaletta et al., Pep5, a new lantibiotic: structural gene isolation and prepeptide sequence, *Arch. Microbiol.* 16–19 (1989).

(List continued on next page.)

*Primary Examiner*—John Ulm
*Assistant Examiner*—Christine Saoud
*Attorney, Agent, or Firm*—Sterne, Kessler, Goldstein & Fox P.L.L.C.

[57] ABSTRACT

A bacterial host is described which is transformed by a plasmid coding for a polypeptide precursor wherein the host comprises a multi-enzyme complex capable of reacting with the expressed polypeptide precursor to produce a polypeptide comprising at least one dehydroamino acid and/or at least one lanthionine bridge. A process for producing a polypeptide comprising at least one dehydroamino acid and/or at least one lanthionine bridge, such as gallidermin, is also described. A plasmid capable of transforming a bacterial host is additionally described.

Also disclosed are recombinant DNA molecules which specify Epi B, Epi C, Epi D, Epi P and Epi Q, enzymes which are involved in the biosynthesis of lantibiotic epidermin.

14 Claims, 44 Drawing Sheets

OTHER PUBLICATIONS

Kellner et al., Gallidermin: a new lanthionine–containing polypeptide antibiotic, *Eur. J. Biochem. 177*:53–59 (1988).

Kellner et al., Gallidermin: a new lanthionine–containing polypeptide antibiotic, *Chemical Abstracts 110:* 4245, abstract No. 4243u 1989).

Khan et al., Complete Nucleotide Sequence of pT181, a Tetracycline–Resistance Plasmid from *Staphylococcus aureus, Plasmid* 10:251–259 (1983).

Koide et al., Cloning and Sequencing of the Major Intracellular Serine Protease Gene of *Bacillus subtilis, Journal of Bacteriolgy 167*(1):110–116 (1986).

Schnell et al., Preptides sequence of epidermin, a ribosmally synthesized antibiotic with four sulfide–rings, *Chemical Abstracts 109*:288, abstract No. 144800c (1988).

Schnell et al., Structural gene isolation and prepeptide sequence of gallidermin, a new lanthionine containing antibiotic, *FEMS Microbiology Letters 58*:263–268 (1989).

Schnell et al., Prepeptide sequence of epidermin, a ribosmally synthesized antibiotic with four sulphide–rings, *Nature 333*:276–278 (1988).

Schnell et al., Analysis of genes involved in the biosynthesis of lantibiotic epidermin, *Eur. J. Biochem. 204*:57–68 (1992).

Shiba et al., Lanthionine peptide, *Chemical Abstracts 104*:206, abstract No. 2246z (1986).

Shiba et al., Lanthionine Peptide, *Kagaku 40*:416–417 (1985) (with English translation).

Vieira et al., The pUC plasmids, an M13mp7–derived system for insertion mutagenesis and sequencing with synthetic universal primers, *Gene 19*:259–268 (1982).

Yanisch–Perron et al., Improved M13 phage cloning vectors and host strains: nucleotide sequences of the M13mp18 and pUC19 vectors, *Gene 33*:103–119 (1985).

FIG.1A

```
1
- TTTAAACTTTATATCATTAATATGTTTAGGAAAAGTAGAAGAAAATTACACTTTTGTAATTTTCTGAATATACATA
                                                                             am

100
                     -
GTATTTATTTGGGGAGTACTAAAAATAATGAAAAGGGTTTTATAATCCTTTTTATAAATTTTT AGGAGT GTTT

200
                                               -
AAA ATG GAA GCA GTA AAA GAA AAA AAT GAT CTT TTT AAT CTT GAT GTT AAA GTT AAT GCA
 M   E   A   V   K   E   K   N   D   L   F   N   L   D   V   K   V   N   A
 -    -30                                   -20
```

FIG. 1B

```
AAA GAA TCT AAC GAT TCA GGA GCT GAA CCA AGA ATT GCT AGT AAA TTT ATA TGT ACT CCT
 K   E   S   N   D   S   G   A   E   P   R ▲ I   A   S   K   F   I   C   T   P
    -10                                    -1 +1

300
GGA TGT GCA AAA ACA GGT AGT TTT AAC AGT TAT TGT TAATTCAGAAGAATTAGATTGGCAGGG
 G   C   A   K   T   G   S   F   N   S   Y   C
    +10                                   +20

400
CTTCAATAGAGGCTCTGTCTCTTAATTTGAGGTGAAATAGAATTGGATAATATATTGTTCCATCGAATATATATATGGT
         am                                                  am
```

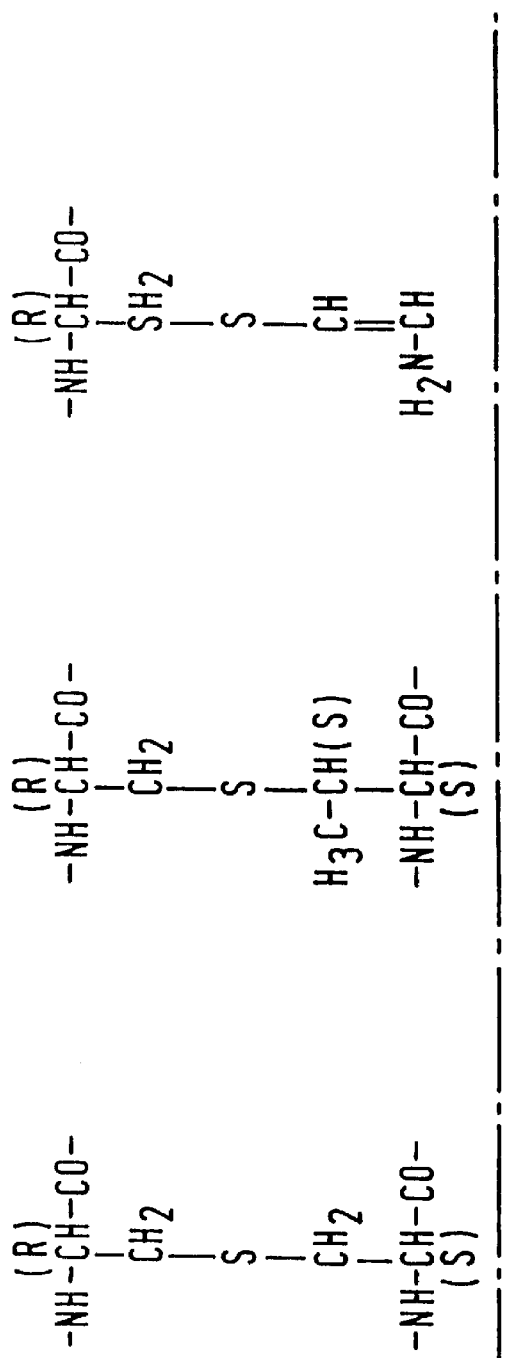
FIG.5A Unusual amino acids found in lanthionine peptide antibiotics ("lantibiotics") derived from protein proantibiotics

EMS 5 plus pCuGal (Gallidermin)

ESTD

| RT | AREA | TYPE | CAL # | AMOUNT |
|---|---|---|---|---|
| 0.73 | 8.4107E+07 | 1SBH | | 0.000 |
| 0.88 | 434710 | DTBB | | 0.000 |
| 1.01 | 3.7223E+07 | SHH | | 0.000 |
| 1.29 | 4978700 | SHH | | 0.000 |
| 1.38 | 5.3775E+07 | ISHH | | 0.000 |
| 1.53 | 349830 | TBB | | 0.000 |
| 2.78 | 343360 | TPB | | 0.000 |
| 3.78 | 444590 | TBY | | 0.000 |
| 4.03 | 218110 | TYY | | 0.000 |
| 7.54 | 408470 | TYB | 1 | 11.519 |
| 9.63 | 132570 | TBP | | 0.000 |

TOTAL AREA = 1.8242E+08
MIN FACTOR = 1.0000E+00

Gallidermin - Standard

ESTD

| RT | AREA | TYPE | CAL # | AMOUNT |
|---|---|---|---|---|
| 0.80 | 111200 | YH | | 0.000 |
| 0.87 | 1.0928E+07 | SHB | | 0.000 |
| 0.99 | 153190 | DTBB | | 0.000 |
| 5.92 | 156570 | PY | | 0.000 |
| 6.36 | 967060 | YY | | 0.000 |
| 7.15 | 580800 | PY | | 0.000 |
| 7.54 | 7492100 | YB | 1 | 211.280 |
| 8.65 | 212540 | BB | | 0.000 |
| 9.61 | 413430 | PY | | 0.000 |
| 9.68 | 256920 D | YY | | 0.000 |
| 9.94 | 255140 I | YH | | 0.000 |

TOTAL AREA = 2.1527E+07
MIN FACTOR = 1.0000E+00

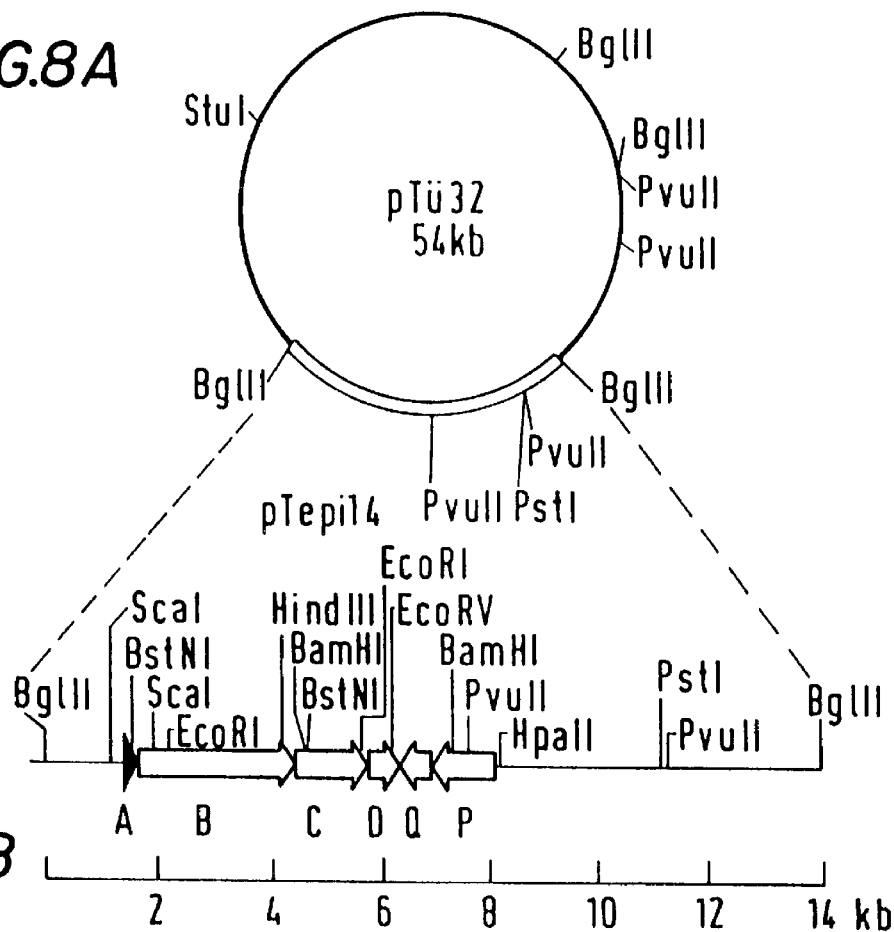

FIG. 9A

```
         BglII                            20                          40
         AGATCTTGTGTTATATAACTAAACAAATTTCTCCATTCGTATTTAGAAAATTGACT
          D  Q  T  I  Y  S  F  L  N  R  W  E  Y  K  S  F  Q  S
    60                          80                          100                         120
TTTATCAAGTTTATCCAAATATATATTTCCAGTATATTCTGTATTAACCCAGCTAATATATTT
 D  L  K  K  D  L  Y  I  N  G  T  Y  E  T  N  L  G  A  L  I  N
                            140                         160                         180
AATAATGTACTTTTTCCACACCCCACTTTCACCCTATAATATTGTAGATATAACCTTTATGAAGAT
 L  L  T  S  K  G  C  G  S  E  G  I  I  N  Y  I  Y  G  K  H  L  D
               200                         220                         240
CCAAACTTATAGAGAATTTATTGTTTATTGTCTTTTGTGAAGTTCAAATCATTATTCCAT
 L  S  I  S  N  I  I  Q  K  N  D  K  T  F  N  L  D  N  I  E  M
                            260                         280                         300
TTTTTGAACAAAGTTATTGTAAGTTGTTTTAATAGTAATACCTCTTCTGGTTCTTTATTTATT
 K  Q  V  F  N  N  Y  T  T  K  I  T  L  V  E  E  P  E  K  N  I
                  320                         340                         360
TTTAAAATTCTATCTGAAGATCCAATTGCTCGTTGTACTTCCGTCCAATAAGATGTAATAGATA
 K  L  I  R  D  S  S  G  I  A  R  Q  V  E  T  W  Y  S  T  I  S  V
```

FIG.9B

```
         380                400                420                440
CTATTGGATTAATAATTTGAAATATAAACATAAGCAAACATATCTCCGCTTTTCATCAT
 I  P  N  I  Q  E  L  Y  L  V  Y  A  F  M  D  G  S  K  M  M
                460                480                500
ATTATTTCCATTAAGTAATAACCCAAAAATAAAAATGTTAATAAATAGAATTAAG
 N  N  E  H  L  Y  Y  G  L  F  L  I  G  F  I  N  I  F  L  I  L
         520                540                560
TTCATAATTGGTTCGAAAAAGATAATACTTTGATCTTATGTAACTCTATATCGAATATATTTT
 N  M  I  P  E  F  F  S  L  V  K  I  K  H  L  E  I  D  F  I  N  K
                580                600                620
TTAATAGGGTATAGTTTTTTATTTTTCGATATTATATGTACTTAAAGTTTTTTATTAATTTTAT
 L  L  T  Y  N  K  I  K  E  I  N  Y  T  S  L  T  K  I  L  K  I
         640                660                680
TGTAGAGATAATCTATTACTATAATAAGAAGATAATTTAGCAGTAGCTTCTTGAGATTACTTGAT
 T  S  L  R  N  S  Y  Y  S  S  L  K  A  T  A  E  Q  S  K  S  S
                700                720                740                760
ACTCTTTTCATTATATTCCTATAGGTAGTATTACAATTATCAATATAGGTAATGTACACACTA
 V  R  K  M  I  N  G  I  P  L  I  V  I  I  L  I  P  L  T  C  V  L
```

FIG.9C

```
              780                800                820
AATATAATGTCAAGGTTTTGTTAATTATATAAAAATATTAGTGATACTATAACTGAAAATAA
 Y  L  T  K  N  I  I  Y  L  F  I  L  S  V  I  V  S  F  L
                     oc N  Y  I  F  I  N  T  I  S  Y  S  F  I  F 840                860                880
ATTCTACAGAAAAAACTCTAGTTATGTTCATAGTATCGTTACTAACCTACTAGTTAAGTTACT
 N                    E  V  S  F  V  R  T  I  N  M  T  D  N  V  L  R  S  T  L  N  S
     am 900                920                940
TGCTGAGTTTTTAAGTGAAAACTATAAGGTAACTTTATCACTTTATTCCATGTAACACTTCTA
 A  S  N  K  L  H  F  S  Y  P  L  K  I  V  K  N  W  T  V  S  R 960                980                1000
ATGTTTTGTATTATTTTTTGACCTATATATCCAAGAATATAAGTAGAAACACCAGAAAATATTA
 I  N  Q  I  I  K  Q  G  I  Y  G  L  I  Y  T  S  V  G  S  F  I  L 1020               1040               1060               1080
AAGTCAGACCAAAACATATAAATGATTACAATTTATCTGTTGATAAGCTAGATTTGTTTAA
 T  L  G  F  C  I  I  I  V  I  K  D  T  S  L  S  S  K  N  L 1100               1120               1140
GGCATTTCTAATTATTAAAGGAATGTATAATGAAAAACTAGTTCCAATCAAACTAAATATTAGT
 A  N  R  I  I  L  P  I  Y  L  S  F  S  T  G  I  L  S  F  I  L 1160               1180               1200
CCAATACTTAAAAGTAGAGTGTTAGTTTGGTTATTTCCATAAATCATATAGACCTTTGATAA
 G  I  S  L  L  L  T  N  P  K  T  I  K  W  L  D  Y  L  G  K  I  I
```

FIG.9D

```
         S/D                                      1260
TATCATCACCTTTTAAACTTTATATCATTAATATAATGTTTAGGAAAAGTAGAAGAAAATTACA
 D  D  G  K  L  S  < epiY IR  1280                    1300                    1320
CTTTTGTAATTTTCTGAATATACATAGTATTTATTTTGGGGGAGTACTAAAATAATAATTGAAA 1340 IR           1360        S/D     1380epiA >        1400
AGGGTTTTATAATCCTTTTTAATAAATTTTTAGGAGTGTTTAAAATGGAAGCAGTAAAAGAAAA
                                           M  E  A  V  K  E  K 1420                    1440                    1460
AAATGATCTTTTTAATCTCTGATGTTAAAGTTGTAAATGCAAAAGAATCTAACGATTCAGGAGCTGAA
 N  D  L  F  N  L  D  V  K  V  V  N  A  K  E  S  N  D  S  G  A  E 1480                    1500                    1520
CCAAGAATTGCTAGTAAATTTATATGTACTCCTGGATGTGCAAAAACAGGTAGTTTTAACAGTT
 P  R  I  A  S  K  F  I  C  T  P  G  C  A  K  T  G  S  F  N  S 1540                    1560                    1580
ATTGTTGTTAATTCAGAAGAATTAGATTGGCAGGGCTTCAATAGAGGCTCTGTCTTAATTTTGA
 Y  C  C  oc                                                 epiB >
```

FIG. 9E

```
S/D1600                      1620                    1640
GGTGAAATAGAATTGGATAATATATTGTTCCATCGAATATATATGGTAAGAACTCCTATAT
 G  E  I  E  L  D  N  I  F  V  P  S  N  I  Y  M  V  R  T  P  I 1660                    1680                    1700                    1720
TTTCAATTGAATTATATAATCAATTCTTAAAATCTGACAATAGATTATGACTTAATTTACA
 F  S  I  E  L  Y  N  Q  F  L  K  S  D  N  I  D  Y  D  L  I  L  Q 1740                    1760                    1780
AAACGATATTTTAAAGAATCTATAATGACAACGACATATAATCTTTATCAAGTATTGGCAAA
 N  D  I  F  K  E  S  I  M  T  T  T  Y  N  L  Y  Q  S  I  G  K 1800                    1820                    1840
ATAGACTGGGAAAAGGATAATAAAAAACCAGAAATGTAAAGAAAGTTTATTAAAATATCTCA
 I  D  W  E  K  D  N  K  K  T  R  N  V  K  E  S  L  L  K  Y  L 1860                    1880                    1900
TAAGAATGAGTACTAGAAGTACACCATATGGAATGCTAAGCGGTGTAGCTTTAGGGAATTTAG
 I  R  M  S  T  R  S  T  P  Y  G  M  L  S  G  V  A  L  G  E  F  S 1920                    1940                    1960
TGAAAATAATAATATTAAAATTAAGGACTCTTCGTTTCATAAAAAGATGTAAAAATAGATGGG
 E  N  N  I  K  I  K  D  S  S  F  H  K  K  D  V  K  I  D  G 1980                    2000                    2020                    2040
CAATGGTTATATAAATTAGTCCATTATTTAGAAAGCGATTACACATATTATAAAGACAGTTTTG
 Q  W  L  Y  K  L  V  H  Y  L  E  S  D  Y  T  Y  Y  K  D  S  F
```

FIG. 9F

```
                        2060                      2080                      2100
TCATATGGAATCAACAAAATTATATTTATAACAATCGTTTATATTTAGATAATAATTCATCAAT
 V  I  W  N  Q  Q  N  Y  I  Y  N  N  R  L  Y  L  D  N  N  S  S  I 2120                      2140                      2160
CACTGAAAATAAAGAAATGATGTATTATCTGTCAAATACAATTCTATATTAGTGTTTATACAT
 T  E  N  K  R  N  D  V  L  S  V  K  Y  N  S  I  L  V  F  I  H

EcoRI 2180                      2200                      2220
GAGAATTCTAAAAAAAATATTACTTATGAAGAACTTGTACAATTGATATCTAGTAAGTACAGTA
 E  N  S  K  K  N  I  T  Y  E  E  L  V  Q  L  I  S  S  K  Y  S 2240                      2260                      2280
TAGAAAATAAAGAGAAGAAGTAAAAGTATTTGTTCAAGAACTCATAAATAAAGAAATTATTTTC
 I  E  N  K  E  E  V  K  V  F  V  Q  E  L  I  N  K  E  I  I  F  S 2300                      2320                      2340                      2360
TGATTTGAGACCTACATTAGAGAATAAAAATCCTTTAGATTACATTATTAATAGTTAAATCCA
 D  L  R  P  T  L  E  N  K  N  P  L  D  Y  I  I  N  S  L  N  P 2380                      2400                      2420
AAAAATAGTTTAGTTGGAACACTTATTAATATTTCTAATGAAATTACAAAATATTCTAAAATGC
 K  N  S  L  V  G  T  L  I  N  I  S  N  E  I  T  K  Y  S  K  M
```

FIG. 9G

```
                    2440                        2460                        2480
CTTTAGGAAAAGGAGAGAATATAAATATTTAGATATTGTTAATTTAATGTCACAATTATTGTTTC
 P  L  G  K  G  E  Y  K  Y  L  D  I  V  N  L  M  S  Q  L  F  V  S
       2500                        2520                        2540
TAAAAACTATTTGCAAATAGATACCTATATAGATTATTCAAGAAATGAATTAAAACAAAGTTTA
 K  N  Y  L  Q  I  D  T  Y  I  D  Y  S  R  N  E  L  K  Q  S  L
                    2560                        2580                        2600
GCTGATAATATTAGTGAAGCAGCATATATTCTCTGGTTATTATCCTAATCATTTTGGTACAA
 A  D  N  I  S  E  A  A  Y  I  L  W  L  L  S  P  N  H  F  G  T
       2620                        2640                        2660                        2680
AAACTATTAGGAATTATCACGAATTTTTTATGGATAAATATGGATTTGAACAACTAGTAAATTT
 K  T  I  R  N  Y  H  E  F  F  M  D  K  Y  G  F  E  Q  L  V  N  L
                    2700                        2720                        2740
AAAGCAATTGCTCTCAGATATAAATGGATTTGGCTATCCCAAAAAGACAGTTATAGTTTTTCT
 K  Q  L  L  S  D  I  N  G  F  G  Y  P  K  K  D  S  Y  S  F  S
       2760                        2780                        2800
AATAACATTGCATTTTTAAAAGAAAAGTATTGCTTGCAATTCAAAATAACAGCCATATTGAAA
 N  N  I  A  F  L  K  E  K  Y  L  L  A  I  Q  N  N  S  H  I  E
                    2820                        2840                        2860
TAACAGAAAACGACGTTAAAAATTTAGAAAAAATAATACAGTTTCTAAAATCAATGCCCTGT
 I  T  E  N  D  V  K  N  L  E  K  N  N  T  V  S  K  I  N  A  P  V
```

FIG.9H

```
      2880                        2900                        2920
TTCAACTGAAATATATAGTGAGATATATTTGGAAATTCAATAAAAGGTTATGAGGATTTGCC
 S  T  E  I  Y  S  E  I  Y  F  G  N  S  I  K  G  Y  E  D  F  A 2940                        2960                        2980                        3000
GTGATAAGTCCAATATTAGGATCTTTTAATGCCGGTGCAACTTTTGGAAGGTTTACGGGAAATT
 V  I  S  P  I  L  G  S  F  N  A  G  A  T  F  G  R  F  T  G  N 3020                        3040                        3060
TCAATATAAAGAAAAAAATCAATTACAAAAGAAATAGTGCATCATTACAATAATTACATGAA
 F  N  I  K  K  K  N  Q  L  Q  K  E  I  V  H  H  Y  N  N  Y  M  N 3080                        3100                        3120
TGAAAATGGTTTAGAATAAGCCAATTAAATGAAGGTCCCTCTTAACTCAAGAATGTAAATATT
 E  N  D  L  E  I  S  Q  L  N  E  A  P  L  N  S  R  N  V  N  I 3140                        3160                        3180
TTGAATAATAATAGAATATATAATACTTGTTTTAAATTTAAATTTACCTAAAGTGATATAGATA
 L  N  N  N  R  I  Y  N  T  C  L  N  L  N  L  P  K  S  D  I  D 3200                        3220                        3240
TAAATGACATATTTATTGGAGCTACATTTAACAAACTTTATCTATATTCTGAAAAACATGATTC
 I  N  D  I  F  I  G  A  T  F  N  K  L  Y  L  Y  S  E  K  H  D  S
```

FIG.9I

```
3260                  3280                  3300                  3320
AAGAATTGTATTCGTATCTAATTCAATGTTTAATTATGAGTTTGGATCTGAATTATACAAATTT
 R  I  V  F  V  S  N  S  M  F  N  Y  E  F  G  S  E  L  Y  K  F
                      3340                  3360                  3380
TTAAGAGAAATTTCATTTGAAAAAACAAAATTTATACAACCTATAACTGAAGAAGGCATTGACT
 L  R  E  I  S  F  E  K  T  K  F  I  Q  P  I  T  E  E  G  I  D
           3400                  3420                  3440
CATTACCTTTTTGTCCAAGAATTATTATAAAGAATTATTTTAAAACCAGCTACTTGGAAAAT
 S  L  P  F  C  P  R  I  I  Y  K  N  I  I  L  K  P  A  T  W  K  I
                      3460                  3480                  3500
AAATTCAGAAATGTTTTCTGAAACTGAAAATTGGTTAAATAGGTTCGCAACTATTAGAGAAAAA
 N  S  E  M  F  S  E  T  E  N  W  L  N  R  F  A  T  I  R  E  K
           3520                  3540                  3560
TGGCATATATTCCAAAAGATGTAATTATTGCTTTTGGAGATAATCGATTGCTATTAAATTTATTAA
 W  H  I  P  K  D  V  I  I  A  F  G  D  N  R  L  L  L  N  L  L
                      3580                  3600                  3620                  3640
ATGACAAGCATCTCATTATACTAAAAAAAAGAACTAAAAAAACATGGTAGGATTCGAATATTAGA
 N  D  K  H  L  I  I  L  K  K  E  L  K  K  H  G  R  I  R  I  L  E
HindIII               3660                  3680                  3700
AAGCTTTATCAATGAATCTAATAATGAGAGAATGTTAGAAATTGTTACGCCATTATATAAAAAA
 S  F  I  N  E  S  N  N  E  R  M  L  E  I  V  T  P  L  Y  K  K
```

FIG.9J

```
                    3720                    3740                    3760
ACTAGTTTAAAAGAGAACAATCTTTCATTATACCTAAAAATAGAAATAAGCACTTCAATAATCTTA
 T  S  L  K  E  Q  S  F  I  I  P  K  N  R  N  K  H  F  N  N  L 3780                    3800                    3820
AAGATTGGTTTTCAATTCATTTAAGTATTCCTAAAACATACCAAGATAATTTTATTCAAGATTA
 K  D  W  F  S  I  H  L  S  I  P  K  T  Y  Q  D  N  F  I  Q  D  Y 3840                    3860                    3880
TCTATTACCATTTATAACGGAATTAAAAGTTAATAATAAATTTTATTAATAATTTTTTTACATAAAA
 L  L  P  F  I  T  E  L  K  V  N  N  F  I  N  K  F  F  Y  I  K 3900                    3920                    3940                    3960
TTTAAAGAAGATGAAGATTTTATAAAATTAAGATTATTAAGAGAAGATGAAGATTATTCTCAAA
 F  K  E  D  E  D  F  I  K  L  R  L  L  R  E  D  E  D  Y  S  Q 3980                    4000                    4020
TTTATTCTTTCATAAAAAATTGGAAAGATTATTGCTTATTAAATAGTGAATTATATGACTATTC
 I  Y  S  F  I  K  N  W  K  D  Y  C  L  L  N  S  E  L  Y  D  Y  S 4040                    4060                    4080
TATAGTTGATTATGTTCCTGAAGTATATAGATAGGGTCCACACGTAATTGAAGATATTGAG
 I  V  D  Y  V  P  E  V  Y  R  Y  G  G  P  H  V  I  E  D  I  E
```

FIG. 9K

```
                4100                         4120                          4140
AATTTTTTATGTATGATAGTCTATTATCAATAAATATATCAATCAGAGTTCAAATTCCAA
 N  F  F  M  Y  D  S  L  L  S  I  N  I  I  Q  S  E  F  K  I  P
                4160                         4180                          4200
AAGAATTATCGTTGCTATATCAATAGATTTTTATTAGATTATTAGAAATTAATAAAAGTGA
 K  E  F  I  V  A  I  S  I  D  F  L  L  D  Y  L  E  I  N  K  S  E
       4220                         4240                          4260                  4280
GAAAGAAGAAATTTAATTAATAATGCGGAAGATTTATATCGTAGTAATGACATAAGAGAATAT
 K  E  E  I  L  I  N  N  A  E  D  L  Y  R  S  N  D  I  R  E  Y
                4300                         4320                          4340
AAAAATTTATTAGCTAAACTTACCAATCCTAAAAAATATGAAATTTTAAAAAAGAATTTC
 K  N  L  L  A  K  L  T  N  P  K  N  D  Y  E  I  L  K  K  E  F
                4360                         4380                          4400
CGAATCTTCATGAATTTCTATTTAATAAAATTAGTATTTTAGAAAATCTTAAAAGACACTACA
 P  N  L  H  E  F  L  F  N  K  I  S  I  L  E  N  L  K  K  T  L  Q

HindIII           s/D    epic >                              4460
AAAAAGCTTATATACTTCACGTTCTAGGATAATTGGCAGTTTTATACACATGCGTTGTAATAGA
 K  S  L  Y  T  S  R  S  R  I    G  S  F  I  H  M  R  C  V  V  I  E
                                  L  A  V  L  Y  T  C  V  V  I  E
```

FIG.9L

```
        4480                    4500                    4520
ATATTCGGTATTAATCCTGAAAAAGAAAAATTTGTTTTATCTATTTTAATGAAATTACAAAA
 I  F  G  I  N  P  E  K  E  K  F  V  L  S  I  F  N  E  I  T  K
 Y  S  V  L  I  K  K  K  N  L  F  Y  L  F  L  M  K  L  Q  K 4540                    4560                    4600
CTAAAAAATATTGGGATGGTTGTGATTAATATATTAATAACATTAAAAAAATTTAGAAAATAAAA
 T  K  K  Y  W  D  G  C  D  *  *  *  *
 L  K  N  I  G  M  V  V  I  N  I  N  N  I  K  K  I  L  E  N  K 4620                    4640
TCACCTTTTTGTCTGACATTGAAAAAGCTACATATATTATAGAAAATCAAAGTGAGTATTGGGA
                             I  T  F  L  S  D  I  E  K  A  T  Y  I  I  E  N  Q  S  E  Y  W  D 4680                    4700                    4720
TCCCTTATACTCTATCTCATGGTTATCCAGGTATAATACTTTTTTTAAGCGCATCAGAAAAAGTA
 P  Y  T  L  S  H  G  Y  P  G  I  I  L  F  L  S  A  S  E  K  V 4740                    4760                    4780
TTTCATAAAGATTTAGAAAAAGTAATACATCAATATATTAGAAAACTAGGCCCTTATTTAGAAA
 F  H  K  D  L  E  K  V  I  H  Q  Y  I  R  K  L  G  P  Y  L  E 4800                    4820                    4840
GTGGTATTGATGGATTTTCACTTTTTAGTGGTCTTTCCGGAATTGGATTTGCGCTAGACATTGC
 S  G  I  D  G  F  S  L  F  S  G  L  S  G  I  G  F  A  L  D  I  A
```

FIG. 9M

```
        4860            4880            4900            4920
GTCTGATAAACAGTACTCTTATCAAAGTATCTTAGAACAAATTGATAATTTACTTGTTCAATAT
 S  D  K  Q  Y  S  Y  Q  S  I  L  E  Q  I  D  N  L  L  V  Q  Y
        4940            4960            4980
GTTTTTGATTTTTTAAATAACGATGCATTGGAAGTAACCCCTACTAACTATGATATAATACAAG
 V  F  D  F  L  N  N  D  A  L  E  V  T  P  T  N  Y  D  I  I  Q
        5000            5020            5040
GATTTTCTGGTATAGGAAGGTACTTGTTAAATAGAATATCGTATAATTATAATGCAAAAAAAGC
 G  F  S  G  V  G  R  Y  L  L  N  R  I  S  Y  N  Y  N  A  K  K  A
        5060            5080            5100
ATTAAAGCATATACTTAATTACTTCAAAACAATTCATTACTCTAAAGACACAATTGGTTAGTTTCA
 L  K  H  I  L  N  Y  F  K  T  I  H  Y  S  K  D  N  W  L  V  S
        5120            5140            5160
AATGAACATCAATTTTTAGATATAGATAAGCAAAATTTCCGTCAGGAAATATAAATTAGGAT
 N  E  H  Q  F  L  D  I  D  K  Q  N  F  P  S  G  N  I  N  L  G
        5180            5200            5220            5240
TAGCGCATGGTATTTTAGGTCCTCTATCATTAACAGCTTTGAGTAAAATGAATGGGATTGAAAT
 L  A  H  G  I  L  G  P  L  S  L  T  A  L  S  K  M  N  G  I  E  I
        5260            5280         EcoRI
CGAAGGCCATGAAGAGTTTTACAAGACTTCACTTCATTTTGCTCAAACCTGAATTCAAAAAT
 E  G  H  E  E  F  L  Q  D  F  T  S  F  L  L  K  P  E  F  F  K  N
```

FIG.9N

```
                                             5360
     5320                       5340
AATAATGAATGGTTCGATCGCTATGATATATTAGAAAATTATATACCTAATTATTCCGTCAGAA
 N  N  E  W  F  D  R  Y  D  I  L  E  N  Y  I  P  N  Y  S  V  R 5420
     5380                       5400
ACGGTTGGTGTGTTACGGTGATACAGGGATTATGAATACATTACTTTTGTCTGGTAAAGCCTTAAA
 N  G  W  C  Y  G  D  T  G  I  M  N  T  L  L  L  S  G  K  A  L  N 5480
     5440                       5460
TAATGAAGGCTTAATTAAAATGTCTAAAAATATTTTAATTAACATATAATAGATAAGAATAATGAT
 N  E  G  L  I  K  M  S  K  N  I  L  I  N  I  D  K  N  D 5560
     5500                       5520                       5540
GATTTAATCAGTCCAACCTTCTGTCACGGACTAGCCATCGCACTTAACCATTATTCATCAAGCGA
 D  L  I  S  P  T  F  C  H  G  L  A  S  H  L  T  I  I  H  Q  A 5620
     5580                       5600
ATAAATTCTTTAATCTATCTCAAGTAAGCACATATCGATACCATTGTCAGAAAATTATTAG
 N  K  F  F  N  L  S  Q  V  S  T  Y  I  D  T  I  V  R  K  I  I  S 5680
     5640                       5660
TCATTATTCTGAAGAAAGTAGTTTTATGTTCCAAGACATAGAGTACTCATACGGACAAAAATT
 H  Y  S  E  E  S  S  F  M  F  Q  D  I  E  Y  S  Y  G  Q  K  I
```

FIG. 90

```
            5700    EcoRI      5720                          5740
TATAAAAACAAAGTGGGAATTCTAGAGGGTGAATTAGGTGTGTTCTTTTAGCTTTACTAGATTATA
 Y  K  N  K  V  G  I  L  E  G  E  L  G  V  L  L  A  L  L  D  Y 5760                 5780                 5800        S/D
TTGATACACACAAAACCAATCAAGGAAAAATTGGAAAAATATGTTTTAATAACATAATAGGAGGA
 I  D  T  Q  N  Q  S  R  K  N  W  K  N  M  F  L  I  T  oc 5820  epiD >        5840                     5860          5880
ATAAGATATATGTATGGAAAAATTATTGATGTCGCTACAGCATCGATAAATGTAATTAATATTAAT
            M  Y  G  K  K  L  L  C  A  T  A  S  I  N  V  I  N  I  N 5900                 5920                 5940
CACTACATAGTTGAGTTAAAGCAACATTTTGATGAAGTTAATATATTATTTAGTCCTAGTAGTA
 H  Y  I  V  E  L  K  Q  H  F  D  E  V  N  I  L  F  S  P  S  S 5960                 5980                 6000
AAAATTTTATAAATACTGATGTTCTCAAGTTATTTTGTGATAACTTGTACGATGAAATTAAAGA
 K  N  F  I  N  T  D  V  L  K  L  F  C  D  N  L  Y  D  E  I  K  D 6020                 6040                 6060
TCCTCTTTTAAATCATATCAATATTGTAGAAAATCATGAATATATTTTAGTATTACCTGCATCA
 P  L  N  H  I  N  I  V  E  N  H  E  Y  I  L  V  L  P  A  S 6080                 6100                 6120
GCAAATACTATTAATAAAAATAGCTAAAGCTAAATCTTTTAACTACTGTATGTTTAA
 A  N  T  I  N  K  I  A  N  G  I  C  D  N  L  L  T  T  V  C  L
```

FIG. 9P

```
       EcoRV          6160                    6180                     6200
     CCGGATATCAAAAATTATTTATATTTCCAAATATGAACATAAGAATGTGGGGAAATCCATTTT
      T  G  Y  Q  K  L  F  I  F  P  N  M  N  I  R  M  W  G  N  P  F  L 6220                    6240                     6260
     ACAAAAAAATATTGATTTACTTAAAAATAATGATGTGAAAGTGTATTCCCTGATATGAATAAA
      Q  K  N  I  D  L  L  K  N  N  D  V  K  V  Y  S  P  D  M  N  K 6280                    6300                     6320
     TCATTCGAAATATCTAGTGGCCGTTACAAAAATACAATATCACAATGCCTAATATTGAAAATGTAC
      S  F  E  I  S  S  G  R  Y  K  N  N  I  T  M  P  N  I  E  N  V 6340            6360  Terminator  6380
     TAAATTTTGTATTAAATAACGAAAAAGACCTTTGGATTAACAAAGGTCTTTTTCTAATTAAAT
         oc  C  L  D  K  R  I  L  I
      L  N  F  V  L  N  N  E  K  R  P  L  D  oc 6400                    6420                     6440
     TTTATATCCGAGTTTACGTTCATTAATAATTTCTATCTCTTTACAATTTTTAAACTATCCCTT
      K  Y  G  L  K  R  E  N  I  I  E  I  E  K  C  N  K  L  S  D  R 6460                    6480                    6500                 6520
     AATCGATGGATATACACATTTATTGTATTAGAATCAACAAAGTCTTCTGTATCCCACACTCCCT
      L  R  H  I  Y  V  N  I  T  N  S  D  V  F  D  E  T  D  W  V  G  K
```

FIG. 9Q

```
6540                          6560                          6580
TTTTAATTCCTCTTTGATACATATCTTCCAAGATTAATATAAGCACCGTAGAATTTTAA
 K  L  E  E  K  S  V  Y  R  G  L  N  I  Y  L  C  R  L  I  K  L 6600                          6620                          6640
TTCTATATTAGAAAAGATTAACTAAGTAATTATTAAACACAAATTGATGGTTTTCAAAGTCTATA
 E  I  N  S  L  N  V  L  Y  N  N  F  V  F  Q  H  N  E  F  D  I 6660                          6680                          6700
AAATCATCATTAACATATTTAATATTCACTTTTTTTATTTCATTTAAAATTCTACATAATATTAAAC
 F  D  D  N  V  Y  K  I  Y  K  K  I  E  N  L  I  R  C  L  I  L  S 6720                          6740                          6760
TTTTGCTTTCATTATTTTTTATAAATCTATGCCTAAACTATAAAAATAACACTTCCT
 K  S  E  N  N  K  I  I  Y  L  D  I  G  L  S  Y  F  Y  C  K  R 6780                          6800                          6820                          6840
ACTATAGCTAGTATTACCCTGTTATTATAACTATTGGAATTTTCCTATAAATTCTTTTAAAAAC
 S  Y  S  T  N  G  T  I  I  V  I  P  I  K  G  I  F  E  K  L  F 6860                          6880                          6900
GTATAATACTCATCAAACTTTCATACACAATTTATAAAATTTGGGTCTATATTGAAGAATTAA
 T  Y  Y  E  D  F  K  E  Y  V  I  I  F  N  P  D  I  N  S  S  N  I 6920                          6940                          6960
TTGTAATTCTTCTATCTAATTCTAAAATACTTTCAATAAGAATAGAATCTACCTCACCGACAAT
 T  I  R  R  D  L  E  L  I  S  E  I  L  I  S  D  V  E  G  V  I
```

FIG. 9R

```
              6980                        S/D      7000                                     7020
ATTAATAGAAATCATTTTATTCCCTTCATTCTTTAAGTAATTTGTATACGTCTAGTTTTCATT
 N  I  S  I  M  < epiQ   op   E  K  L  L  K  Y  V  D  L  K  G  N
                      7040                         7060                        7080
ACCATAATGTTTTTTATCCATATATTTTTCTTTTTCTATCCCTTTTTTCTTAAATAACTCTATA
 G  Y  H  K  K  D  M  Y  K  E  K  E  I  G  K  K  K  F  L  E  I
          7100                       7120                     7140                  7160
GCTGTTTCGGGTTGGTCTTTTAATTGATACTTATCAATTTCTAGTGCTAAAGCTCCAGAAACCT
 A  T  E  P  Q  D  K  L  Q  Y  K  D  I  E  L  A  L  A  G  S  V  K
                   7180                      7200                    7220
TGGGTGCAGCAAGTGATGTCCCTGATTGATATATGTATCTTCCATTAGAAGAAGTACTAAAAC
 P  A  A  L  S  T  G  S  Q  Y  I  Y  R  G  N  S  S  T  S  L  V
                7240                     7260                      7280
ACTTTGTTTTTGCATATATCCTTTTTCTAACCAAGCATCTTTTCCATACTTATCTAAAAGTTTA
 S  Q  K  Q  M  Y  G  K  E  L  W  A  D  K  G  Y  K  D  L  L  K
            7300                     7320                     7340
TAAGAACCTCCTATCGTCATTAAATCTATAAATTATTCCATAATTAGAAAACTCAGAAATAT
 Y  S  G  G  I  T  M  L  D  I  F  N  N  G  Y  N  S  F  E  S  I  Y
```

FIG.9S

```
        7360      BamHI      7380                        7400
     AATCATTATCATCGATGGATCCATACAGTCATATAACATTATTAGATTTGCTGGGCTATCATATAC
      D  N  D  D  I  S  G  V  T  M  V  N  N  L  N  A  P  S  D  Y  V
     7420                       7440                      7460                7480
     CTTTTTTGATGTTTTTAGAATTTAGATTCTTTTTTATTATTCTTTTTTATTCTTTTTTTACTTTTTTTTACATTG
      K  K  S  T  K  S  N  L  N  R  R  K  K  N  I  E  K  -  V  K  K  V  N
                 7500                      7520                    7540
     ATACCGTCATTACCCACAGCTGCAACAACAATACTACCTTTTTTTTGAGCATAGTTTATAGCTT
      I  G  D  N  G  V  A  A  V  V  I  S  G  K  K  Q  A  Y  N  I  A  K
                       7560                    7580                      7600
     TCTGTAGTGCATCGTAATCAACTTTTTCATCATCTCTTAATTTTTTTTATTTTGATTATCTTT
      Q  L  A  D  Y  D  V  K  E  D  D  R  L  K  K  N  Q  N  D  K
     7620                      7640                    7660
     AATTAAATAATTTCCTAAACTAACGTTGATTACATCATTGTCATCATTGCTGCATCAATAATT
      I  L  Y  N  G  L  S  V  N  I  V  D  N  D  D  N  A  A  D  I  I
                     7680                       7700                7720
     CCTTTAGATACCCAAAGCATTTCACTTTTCTTTGAGCCAAATACTCGGTATACATTCATCCTA
      G  K  S  V  W  L  M  E  S  K  K  S  G  F  V  R  Y  V  V  N  M  E  V
     7740                      7760                     7780                7800
     CTCCAGGGTTTACACCTTTTAAATTACCGTTTGCTCCTATTTGTCCTGCTACTAATGTACCATG
      G  P  N  V  G  K  L  N  G  N  A  G  I  Q  G  A  V  L  T  G  H
```

FIG.9T

```
                                            7840                        7860
ATTCAATTTATCTTCTTCAAAATTTTTATTCCTGATTCATCGTTTTCGCTACCTCTAAAACCA
 N  L  K  D  E  E  F  N  K  N  G  S  E  D  N  E  S  G  R  F  G
         7880                       7900                       7920
TTTTAGGCACTTCATTAACTATCTTATTATACTCTTAAATCTGTATGACTACTATTCACAC
 N  K  P  V  E  N  V  I  K  N  I  S  K  L  D  T  H  S  S  N  V  G
               7940                       7960                       7980
CAGAATCTACTAAAGCAACTTTTGCTTTTTCTATCTGGACTTAGCTTATAACTTTTACCTTC
 S  D  V  L  A  V  K  A  K  K  R  D  P  S  L  K  Y  S  K  G  E
                     8000                       8020                       8040
ATTTGTTATTTTTCGCATATCCCATTGTCTGTCAAATAAATCATGGCTGCCATTTTTTATTA
 N  T  I  K  R  M  D  W  Q  R  D  F  L  D  H  S  G  N  K  K  N
         8060                       8080                       8100                       8120
TTTAAATTTTTTCCTGTCTTTACAGATTTTCAACTACACAAGTGGAACAGGTAGGATTACAA
 N  L  N  K  G  T  K  V  S  K  E  V  V  C  T  S  C  T  P  N  V  F
                     8140                       8160                       8180
ACTTGACGTTTTTATTACTCTTTATTAGTGAATTAATTTGATTTGCTAGTTTTAATTTGTGC
 K  V  N  K  N  S  K  I  L  S  N  L  K  S  K  S  T  K  I  Q  A
```

FIG. 9U

```
                     8200           HindII  8220                        8240
TGTATGTAGTTCAGGAATTTTATAAGTTAACTCGATATTTTTTGTTTAATGGATTCTTAAAA
 T  H  L  E  P  I  K  Y  T  L  E  I  N  K  Q  K  I  S  E  K  F 8260                      8280                   8300
GTTTTTGCATTATCATATTCAACACTATAAATAACTTAATTCTTCATTAGTGAACTTCCAAAAG
 V  F  A  I  I  I  S  T  L  *
 T  K  A  N  D  Y  E  V  S  Y  Y  S  L  E  E  N  L  S  S  G  F  A 8320               8340                    8360
CATACTCATTTGCAAAAAACTAATGACAATATTAAAAAAACAATGAAAAATTAAATTGTT
 Y  E  N  Q  L  F  V  L  S  L  I  L  F  V  I  F  F  K  N 8380     S/D    8400                     8420              8440
CATATAGCACCTCTAACATATTATTATTAACATTAATTAACACTTATGTTTTTACTTTT
 M < epiP 8460                  8480                 8500
TTATTTATATTATATCTTTAATAATGTTCTGTTGCAAGATGAAAATACGAGGTATCAAGTACCG 8520                    8540                    8560
ATACAGGGAGTATTACACTCAATTAATTAAAATAAAATATGTTGTGATTAAAATTTATTTAT 8580                  8600             KpaII
AAAAGTATGGGCAATTTATTATTATTATTCAAGTTAAAACAAAGAGTCCGGGACATAAAGTTTCAGC 8640                    8660                    8680
CTCTTCGTCCTAATTACCAAAAATCCTTTTTAGATTGGTTTTTTCTAATT

8700
TTTT
```

FIG.11A

```
Active site I:
                                          *
EPIP    130  EGKSYKLSPDRKKAKVALVDSGVNSSHTDLKSINKIVNEVP  170
             ..:::::.:::::::
SUBSI   119  APALHSQGYTGSNVKVAVIDSGIDSSHPDLNVRGGASFVPS  159
             ..:   :.: :.:.:
ISPI     31  APEMWAKGVKGKNIKVAVLDTGCDTSHPDLKNQIIGGKNFS   71
             .::.:::.:::.:
SUMYTV   19  QAPQAWDIAEGSGAKIAIVDTGVQSNHPDLAGKVVGGWDFV   59
                                          *
```

FIG. 11B

```
Active site II:
                                                              *
EPIP   170  PKNGERGSENDESGNKNFEEDKLNHGTLVAGQIGANGNLKGVNPGVEMNVY  220
            :.  :::.:    ......    .::  :::  :::  :: .:  :::
SUBSI  146  PDLNVRGGASFVPSETNPYQDGSSHGTHVAGTIAALNNSIGVLGVSPSASL  196
            : :. ::. :. .:.:  :.:: ::.:::::::  ::: :: :: .::
ISPI   163  QIIGGKNFSDDDGGKEDAISDYNGHGTHVAGTIAANDSNGGIAGVAPEASL  113
                                 ::: :: ::::::  :
SUMYTV  67                       NGNGHGTHCAGIAAAVTNNST              87
                                           *
Active site III:
                                                              *
EPIP   380  YMQKQSVLSTSSNGRYIYQSGTSLAAPKVSGALALEIDKYQ            420
            :: :: :.   :: :.  :::.:::::.::.::: :::::
SUBSI  305  MAPGVSIQSTLPGGTYGAYNGTSMATPHVAGAAALILSKHP            345
            .::: .   ::::   .::::::: :::::.::: :
ISPI   224  VAPGENILSTLPNKKYGKLTGTSMAAPHVSGALAL-IKSYE            263
            .::: :: : .:. ...  :::::: :::::::
SUMYTV 203  AAPGSWIYSTYPTSTYASLSGTSMATPHVAGVAGLLASQGR            243
                                           *
```

FIG. 12

```
               10         20         30         40         50         60
EPIQ   MISINIVGEVDSILIESILELDRRITINSSNIDPNFIIVYEKFDEYTFLKEFIGKIPIV
                                              : :: :
PHOB   VLEQNGFQPVEAEDYDSAVNQLNEPWPDLILLDWMLPGGSGIQFIKHLKRESMTRDIPVV
              30         40         50         60         70         80
                                                                    110

70         80         90        100        110        120
EPIQ   IITGNTSYSRKCYFYSLGIDLYIIKNNESKSLILCRILNEIKKYIKYVNDDFID----F
       : :::: .    . : ::::   :::: . :::.:  ::        .
PHOB   MLTARGEEDRVRGLETGADDYITKPFSPKELV-ARIKAVMRRISPMAVEEVIEMQGLSL
              120        130        140        150        160        170
                  90        100        110        120        130

130        140        150        160        170
EPIQ   E--NHQFVFNNYLVNLSNIELKILRCLYINLGRYVSKEELKKGVWDTEDFVDSNTINVYI
        . .:    :.: :: :: . ::  :. .  .::::: .   ::::::    ::::
PHOB   DPTSHRVMAGEEPLEMGPTEFKLLHFMTHPERVYSREQLLNHVWGTNVYVEDRTVDVHI
              150        160        170        180        190
                180        190        200

EPIQ   HRLRDSLKNCKEIEIINE-RKLGYKILIRKDLC
        .: ::: .      :.:  ::  ::  .::
PHOB   RRLRKALEPGGHDRMVQTVRGTGYRFSTRF
              210        220
          200
```

DNA ENCODING AND BIOSYNTHETIC PROCESS FOR THE PREPARATION OF CHEMICAL COMPOUNDS, LANTIBIOTICS

CROSS-REFERENCE TO RELATED APPLICATION

This application is a continuation, of application Ser. No. 07/876,791, filed Apr. 30, 1992, now abandoned, which is a continuation of application Ser. No. 07/784,234, filed Oct. 31, 1991, now abandoned, which is a continuation-in-part of application Ser. No. 07/353,590, filed May 18, 1989, now abandoned, the disclosure of which non-abandoned application is entirely incorporated here by reference.

FIELD OF THE INVENTION

This invention relates to the biosynthesis of chemical compounds, and in particular to the biosynthesis of chemical compounds containing dehydroamino acid residues and/or thioether bridges. The invention also relates to the use of recombinant genetics to prepare enzymes involved in the biosynthesis of such chemical compounds.

BACKGROUND OF THE INVENTION

Some polypeptide antibiotics such as nisin, subtilin, duramycin, cinnamycin, ancovenin, Ro 09-0198 and epidermin contain dehydroamino acids and lanthionine bridges. These polypeptides are produced by various respective strains of microorganism. Nisin for example can be produced by cultivating strains of *Streptococcus lactin*, and subtilin by cultivation of *Bacillus subtilis*.

The genetic basis for the biosynthesis of these antibiotics has not, hitherto, been elucidated. Thus, it has not been known, for example, whether biosynthesis of such antibiotics and, in particular, the formation of the unusual amino acids found therein occurs via ribosomal synthesis or via multi-enzyme complexes.

It addition it was not know whether the precursor proteins of such antibiotics were coded by distinct structural genes or were the degradation products of larger proteins.

In the course of work carried out to establish the structural gene of epiderm, we have been able to establish that surprisingly the above mentioned antibiotics, in particular epidermin, are each coded by a distinct structural gene, and that processing of a presequence polypeptide is carried out by an enzymatic complex which effects formation of dehydroamino residues and/or thioether bridges.

Furthermore, the multi-enzyme complex may be involved in the secretion of the protein through the cell membrane into the culture supernatant, as well as processing a pre-polypeptide. In this connection, such activity may be associated with a pre-sequence possessed by the pre-polypeptide, e.g., as in the case of the −30 to −1 sequence of pre-epidermin as described below.

DESCRIPTION OF THE DRAWINGS

FIGS. 1A and 1B (SEQ ID NO:10) depict the nucleotide sequence of the epidermin structural gene (epi A) and the deduced amino acid sequence of pre-epidermin. A Shine-Dalgarno sequence is boxed and the proteolytic cleavage site at which the propeptide is processed is indicated by an arrow. Inverted repeats are underlined and potential stop codons are noted as am (amber) and oc (ochre).

FIGS. 5A and 5B depict examples of unusual amino acids which are found in lanthionine antibiotics and which can be formed in peptide products using the method of this invention.

FIG. 7B depicts the elution pattern of a standard containing gallidermin. Gallidermin is eluted at 7.54 minutes.

FIGS. 8A–8C is a genetic analysis of episome pTü32 of *S. epidermidis* plasmid pTü32, including 8A: a restriction map of episome pTü32, and 8B: a restriction map of the 13.5 kb BglII fragment of pTü32. The filled arrow corresponds to the epiA structural gene. Open arrows represent reading frames epiB, C, D, P and Q.

Figure 2A:
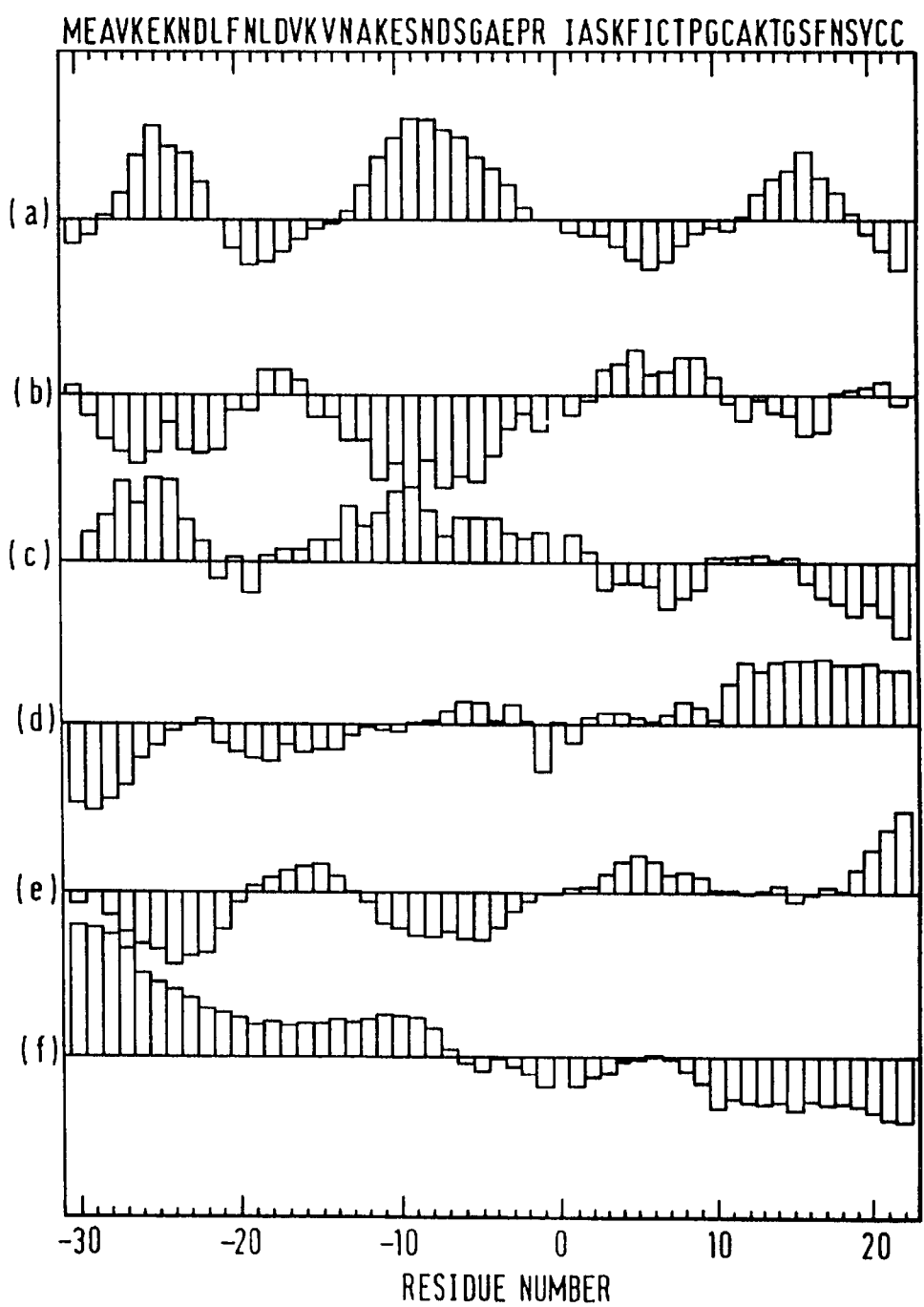
FIG. 2A (SEQ ID NO:11) depicts a prediction plot for pre-epidermin using a Hyron program, in which the respective bar charts show: (a) flexibility; (b) hydropathy; (c) hydrophilicity; (d) propensities for turn; (e) β-sheet; and (f) α-helix conformation.

8C: Southern hybridization of pTü32 digested with different restriction enzymes (EcoRi, EcoRV, BglII, SphI) using a 15-mer oligonucleotide (5'CACATCCAGGAGTAC-3') (SEQ ID NO:1) specific of epiA.

FIG. 9A–9U corresponds to the nucleotide sequence of SEQ ID NO:16 as an 8700 nucleotide sequence of the BglII/HpaII fragment of pTü32 containing reading frames epiA (nucleotides 1381–1536 of SEQ ID NO:16), epiB (nucleotides 1593–4662 of SEQ ID NO:16), epiC (nucleotides 4441–5805 of SEQ ID NO:16), epiD (nucleotides 5824–6366 of SEQ ID NO:16), epiP (nucleotides complimentary to the DNA sequence 8379-6996 of SEQ ID NO:16), epiQ (nucleotides complimentary to the DNA sequence 6983-6369 of SEQ ID NO:16); epiY (nucleotides complimentary to the DNA sequence 1227-784 of SEQ ID NO:16); epiY' (nucleotides complimentary to the DNA sequence 1226-831 of SEQ ID NO:16); and epiY" (nucleotides complimentary to the DNA sequence 827-3 of SEQ ID NO:16), and Y" and the deduced amino acid sequences: EpiY" as amino acids 275–1 (SEQ ID NO: 17) of FIG. 9), encoded by nucleotides complimentary to nucleotides 827–3 of FIG. 9 (SEQ ID NO:16); EpiY as 148 amino acids (SEQ ID NO:18) encoded by 444 nucleotides complimentary to 1227–784 of FIG. 9 (SEQ ID NO:16); EpiA as 52 amino acids (SEQ ID NO:19) encoded by 156 nucleotides 1381–1536 of FIG. 9 (SEQ ID NO:16); EpiB as 990 amino acids (SEQ ID NO:20) encoded by 2970 nucleotides 1593–4562 of FIG. 9 (SEQ ID NO: 16); EpiC as 455 amino acids (SEQ ID NO:21) encoded by 1365 nucleotides 4441–5805 of FIG. 9 (SEQ ID NO:16); EpiD as 181 amino acids (SEQ ID NO:22) encoded by 543 nucleotides 5824–6366 of FIG. 9 (SEQ ID NO:16); EpiP as 461 amino acids (SEQ ID NO:24) encoded by 1383 nucleotides complimentary to 8379–6996 of FIG. 9 (SEQ ID NO:16); and EpiQ as 205 amino acids (SEQ ID NO:23) encoded by 615 nucleotides complimentary to 6983–6369 of FIG. 9 (SEQ ID NO:16) of the respective proteins. S/D sequences and termination structures are overlined. IR indicates inverted repeats. The start of the open reading frames of epiY, epiA, epiB, epiC, epiD, epiQ and epiP are indicated by bold letters. The N-terminal amino acid residues (possible translational start sites) are boxed.

FIGS. 10A–10B shows the results of a Northern blot analysis of epiA (10A) and epiB (10B) expression in *S. epidermidis*, in which total RNA (40µg, lanes 1, 3, and 5, or 20 µg, lanes 2, 4, and 6) were separated on 1.2% agarose gels and hybridization was performed with an antisense RNA probe (SP6 transcript. Filters were washed with increasing stringency; lanes 1, 2:1×SSC, 0.1% SDS, exposition time, 4 h, lanes 3, 4:0.5×SSC, 0.1% SDS, exposition time 16 h; lanes 5,6:0.1×SSC, 0.1% SDS, exposition time, 3 days). The positions of 235 and 165 RNAs were used as a size standards.

FIGS. 11A and 11B show sequence homologies between EpiP and different serine proteases at the active sites (SUBSI, subtilisin I168 precursor of *B. subtilis* (Terzaghi et al., *Appl. Microbiol.* 29: 807–813 (1975); ISPI, major intracellular serine protease from *B. subtilis* (Maniatis et al., *Molecular Cloning. A Laboratory Manual*; 2nd ed. Cold Spring Harbour Laboratory Press (1990); SUMYTV, thermitase from *Thermoactinomyces vulgaris* (Stahl et al., *J. Bacteriol.* 158–411-418 (1984)). Three active sites are compared. In active site I, amino acids 130–170 of EPIP (SEQ ID NO:25) are compared to amino acids 119–159 of SUBSI (SEQ ID NO:26); amino acids 31–71 of ISPI (SEQ ID NO:27); and amino acids 19–59 of SUMYTV (SEQ ID NO:28). In active site II, amino acids 170–220 of EPIP (SEQ ID NO:29) are compared to amino acids 146–196 of SUBSI (SEQ ID NO:30); amino acids 163–213 of ISPI (SEQ ID NO:31); and amino acids 67–87 of SUMYTV (SEQ ID NO:32). In active site III, amino acids 380–420 of EPIP (SEQ ID NO:33) are compared to amino acids 305–345 of SUBSI (SEQ ID NO:34); amino acids 224–263 of ISPI (SEQ ID NOS:35–36); and amino acids 203–243 of SUMYTV (SEQ ID NO:37) conserved asparagine (asp), histidine (his), and serine (ser) residues are marked by asterisks. Similar amino acid residues are indicated by points and identical amino acid residues by colons.

FIG. 12 shows sequence homologies between epiQ and PhoB (Makino et al., *J. Mol Biol.* 190:37–44 (1986)). Similar amino acid residues are indicated by points and identical amino acid residues by colons. Amino acids 1–205 (1–115 as SEQ ID NO:38 and 116–205 as SEQ ID NO:41) of EpiQ (PIQ) are compared to amino acids 21–229 (21–113 as SEQ ID NO:39 and 114–229 as SEQ ID NO:40) of PhoB.

Figure 13A:
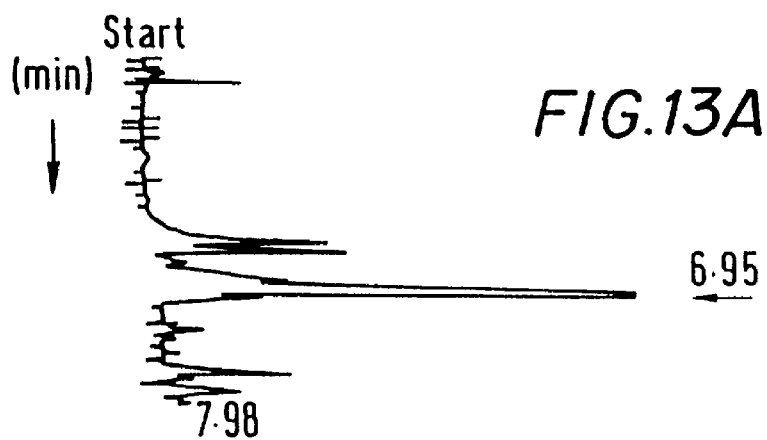
Figure 13B:
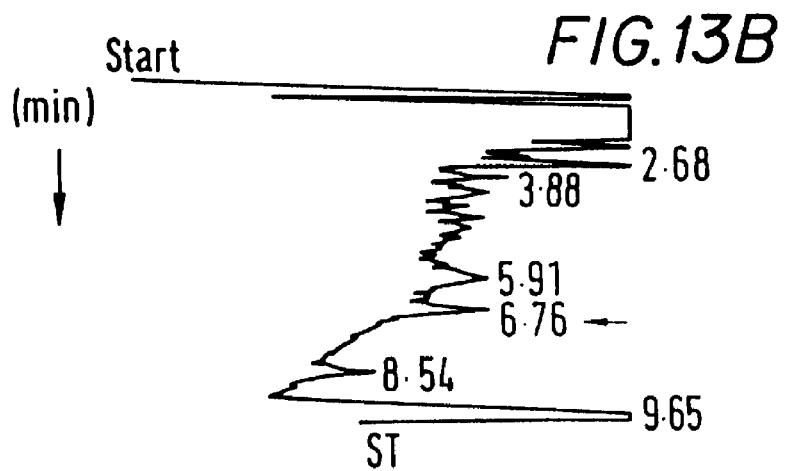

FIGS. 13A–13B show HPLC elution profiles of epidermin which was produced in *S. carnosus* TM300.

13A: Elution profile of epidermin standard substance (6.75 min, indicated by an arrow).

13B: Elution profile of epidermin standard substance (6.75 min, indicated by an arrow) isolated from culture filtrates of *S. carnosus* TM300 pTepi14. Culture filtrates were adsorbed to XAD 1180, eluted with methanol and finally concentrated by evaporation.

13C: Elution profile of untransformed *S. carnosus* TM300 culture filtrate treated as in 13B. The solid line indicates the elution region of epidermin.

Figure 14:
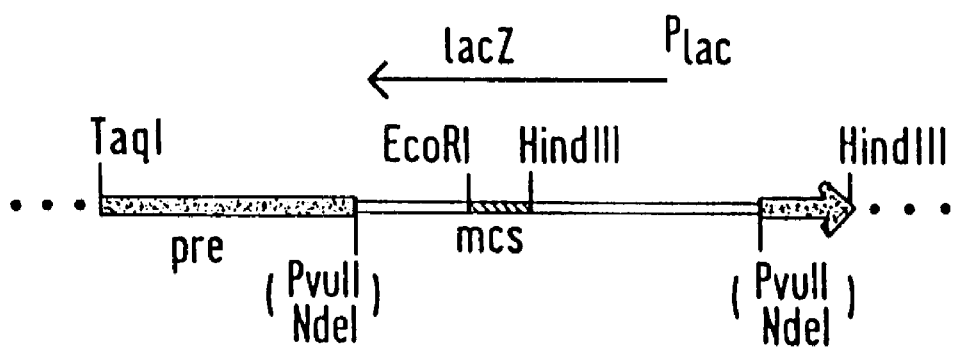

FIG. 14 shows the construction of pT181mcs. The PvuII$^{309}$–Pvu$^{631}$ fragment of pUC19, part of lacZ and the multiple cloning site (mcs), was inserted into the single NdeI site within pre of pT181 (Gennaro et al., *J. Bacteriol.* 169:2601–2610 (1987); Kahn et al., *Plasmid* 10:251–259 (1983)) by blunt-end ligation. lacZ is in the opposite orientation to a pre. Black bar, interrupted pre; open bar, inserted pUC19 fragment.

Figure 15:
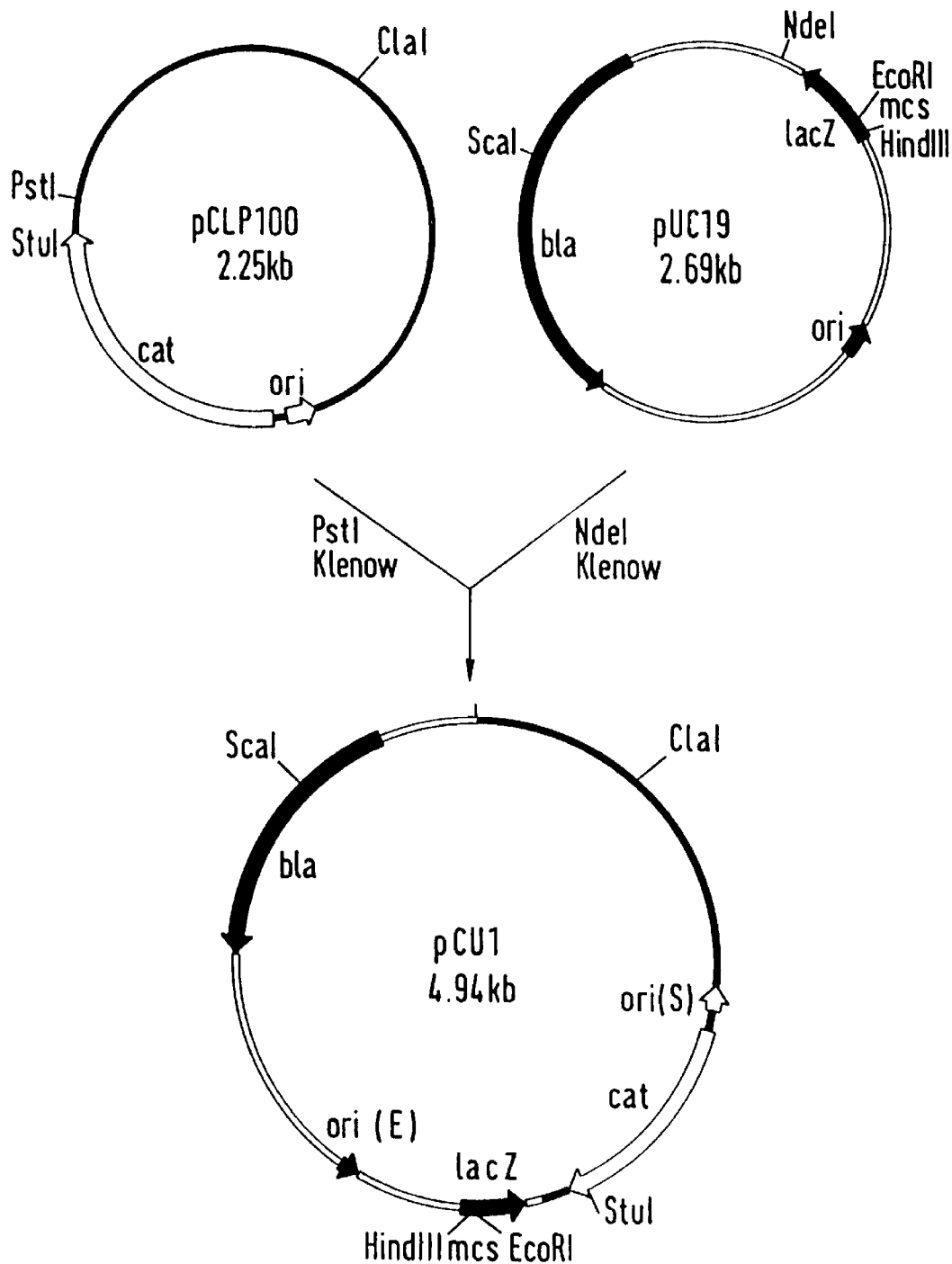

FIG. 15 shows the construction of pCU1. PCLP100is a derivative of pC194 (Horinouchi et al., *J. Bacteriol.* 150:815–825 (1982)) containing a single Pst1 site which was generated by opening pC194 at the HindIII site, deleting the ends with Ba131(approximately 950 bp) and inserting a PstI-linker by blunt-end ligation. PCU1 was then generated by blunt-end ligation of pCPL100 and pUC19 (Vieira et al., *Gene* 19:259–268 (1982)) via the single PstI and NdeI sites, respectively. The multiple cloning site (mcs) in front of lacZ was used for cloning various epi gene-containing fragments. This shuttle vector replicates both in staphylococci and *E. coli*.

Figure 16A:
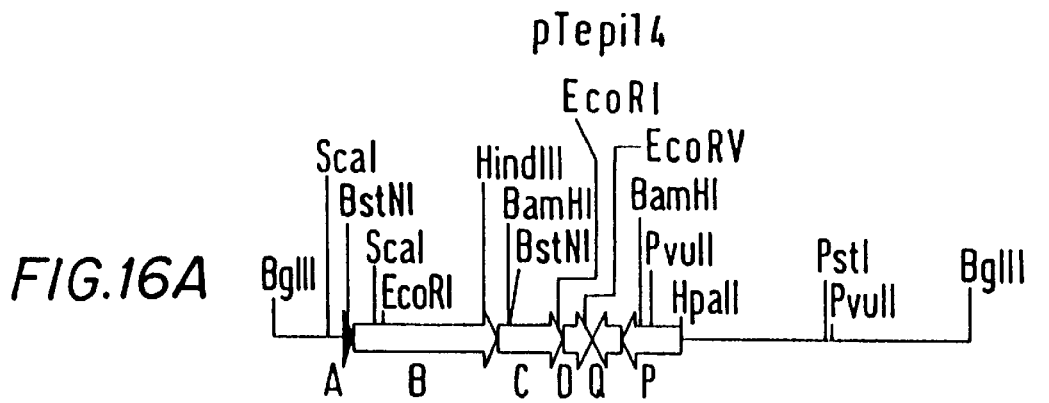
Figure 16B:
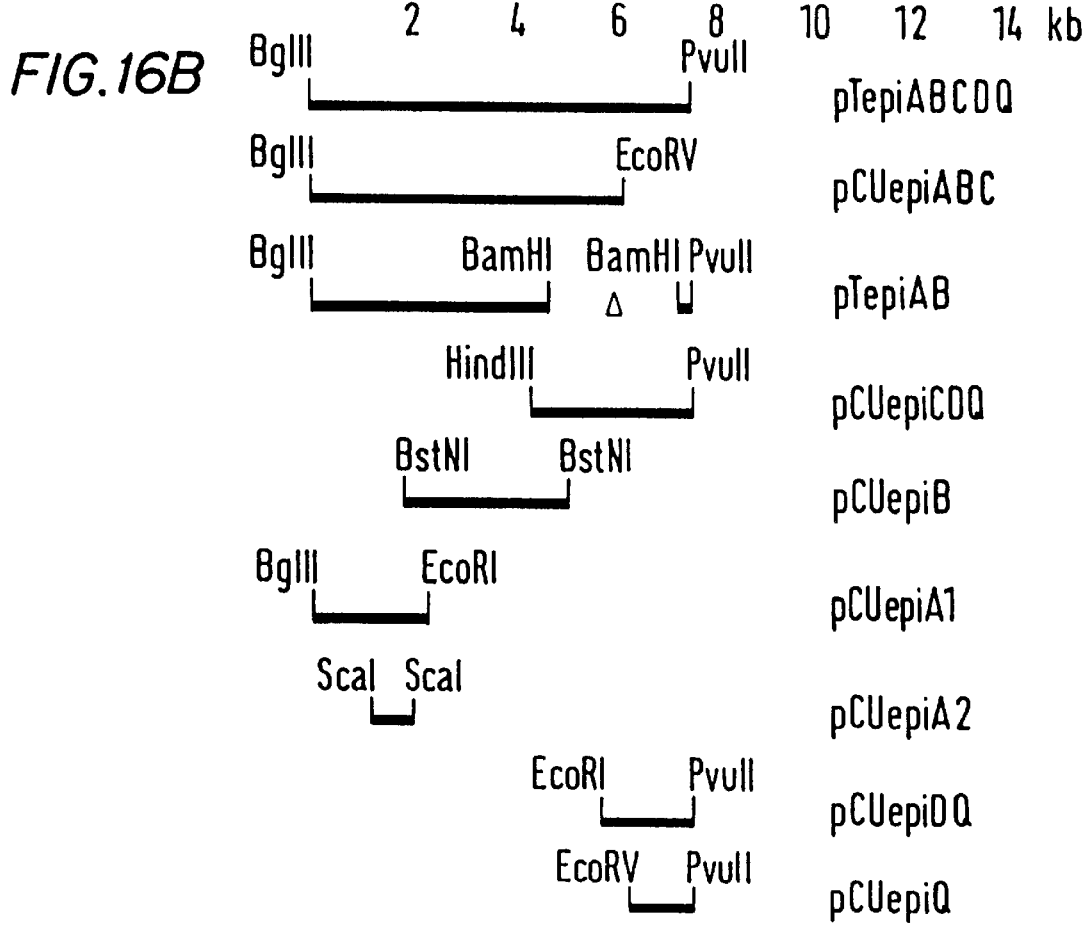

FIGS. 16A and 16B show:

A) the generation of pTepi14 by cloning the 14 kb BglII fragment of pTü32 in pT181mcs. This fragment containing the entire genetic information necessary for epidermin production in *S. carnosus*. The indicated ORFs and their transcriptional directions (indicated by arrows) are deduced from the DNA sequence. epiA, the structural gene, is presented by the black arrow.

B) various pTepi14 DNA fragments subcloned into pT181mcs (pT . . .) or pCU1 (pCU . . .). The respective plasmids were used to complement the *S. epidermidis* Epi⁻ mutants. The complete ORFs represent in the plasmid are indicated.

Figure 17:
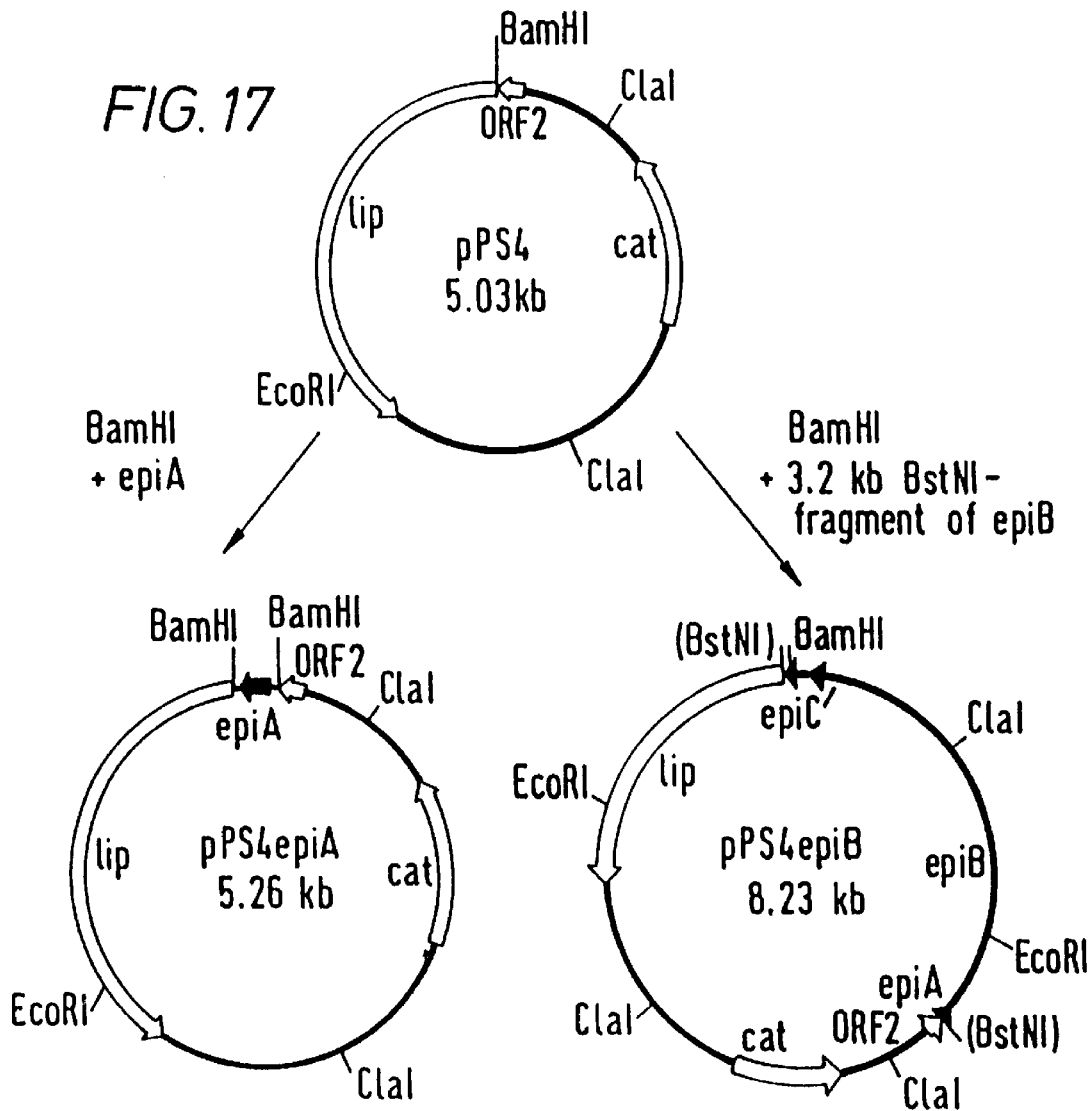

FIG. 17 shows the construction of pPS4epiA and pPS4epiB. pPS4 is a derivative of pLipPS1 (Liebl et al., *Mol. Gen. Genet.* 204:166–173 (1986)). A single BamHI site was inserted after a strong staphylococcal promoter. Cloning of genes into the BamHI site under the control of the ORF2 promoter normally leads to good expression in staphylococci. epiA was PCR-amplified and contained flanking BamHI sites. The 3.2 kb BstNI fragment containing epiB was inserted into the BamHI site by blunt-end ligation. The respective EMS-mutants were complemented only when epiA and epiB were under the control of the ORF2 promoter. lip, lipase gene; cat, chloramphenicol acetyl transferase gene; ORF2, *S. carnosus*-specific truncated ORF.

Figure 18:
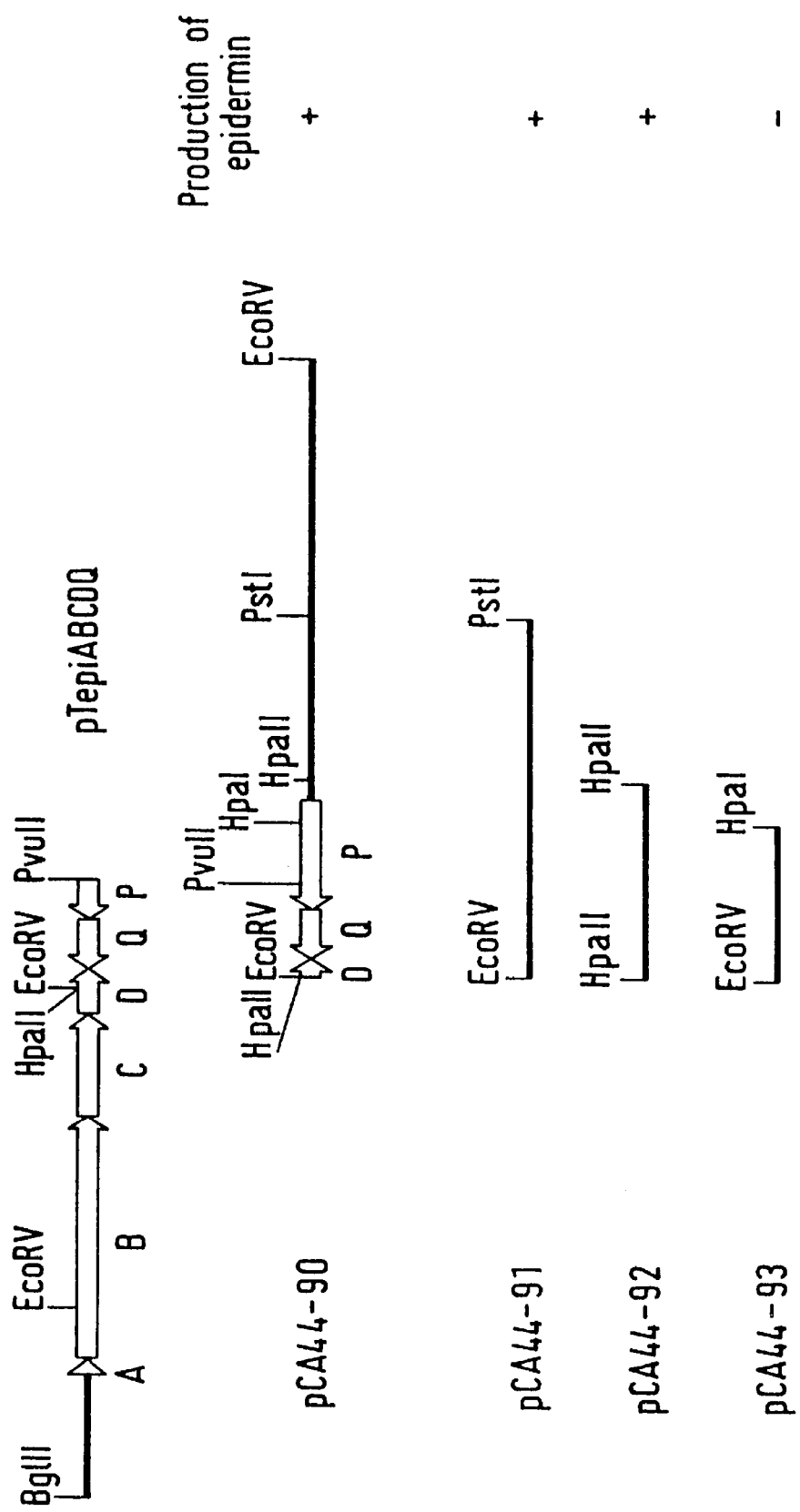

FIG. 18 shows the complementation of epidermin production in *S. carnosus* (pTepiABCDQ) by flanking DNA fragments. The fragments were subcloned into the compatible plasmid.

DESCRIPTION OF THE PREFERRED EMBODIMENTS

Broadly speaking the present invention provides in one aspect a bacterial host containing a plasmid, wherein said plasmid codes for a polypeptide which is not normally produced by said host, and wherein said host during cultivation provides a multi-enzyme complex whereby a polypeptide is produced which contains at least one dehydroamino acid and/or at least one lanthionine bridge, said produced polypeptide being foreign to said host.

A suitable multi enzyme complex is one which is capable of effecting at least one of the following operations, namely water elimination and sulphide bridge formation; the complex may also effect decarboxylation and double bond formation.

Suitable hosts for carrying out the process of the present invention are those which, without modification of their genetic material, are capable of producing polypeptides containing a dehydroamino acid residue and/or lanthionine bridge and/or a methyl lanthionine bridge. Examples of such hosts are *Streptococcis lactis, Bacillus subtilis, Streptomyces cinnamoneus, Streptomyces sp. Streptoverticullum griseoverticillum, Staphylococcus epidermidis Staphylococcus epidermin* strain 5, *Staphylococcus gallinarum* and mutant strains thereof, e.g., a mutant strain of *S. epidermin* DSM 3095 which is incapable of producing epidermin.

Strains which are of special interest are *Staphylococcus gallinarum* (F16/P57) Tü 3928 which has been deposited with the Deutsche Sammlung von Microorganismen under the terms of the Budapest Treaty on 18 May 1988 and has received the depository number Tü 3928 in DSM 4616 and *Staphylococcus epidermidis DSM* 3095 which was deposited by the present applicants with the Deutsche Sammlung von Microorganismen under the terms, Mascheroder Weg 1B, 38124 Braunschweig, Germany, of the Budapest Treaty on 26th Oct. 1984.

In order to transform a suitable host, a suitable plasmid may be modified by known genetic engineering techniques.

Desirably a plasmid from a host which produces a polypeptide containing at least one dehydroamino acid residue and/or at least one sulfide bridge is treated by modifying or replacing the gene coding for a pre-polypeptide to provide a plasmid coding for a polypeptide foreign to said host and then transforming said host with the altered plasmid.

Any of a variety of methods may be used to replace or modify a gene coding for the pre-polypeptide.

DNA coding for the pre-polypeptide sequence of the desired compound can be prepared by chemical synthesis. Suitable chemical syntheses have been disclosed in *Anal. Biochem.* 121, 365 (1982). The known techniques allow the preparation of polynucleotides, e.g., of up to 60 to 100 bases to be prepared.

Suitable protected nucleotides can be linked by the phosophotriester method Agarwal et al., (*Agnew, Chem.* 84, 489 (1972)), the phosphotriester method (Reesem., *Tetrahedron* 39, 3, (1983)) or the phosphitetriester method (Letsinger et al., *J. Am. Chem. Soc.* 98, 3655 (1976)) or the phosphoramidite method. The solid phase method allows for simplification of the synthesis of the polynucleotides.

The double stranded DNA can be constructed enzymatically from chemically prepared short but overlapping segments.

For example, overlapping polynucleotide sequences from both DNA strands can be used, which are held together in the correct conformation by base pairing and are then chemically linked by the enzyme DNA ligase (Khorana et al., *J. Biol. Chem.* 251, 565 (1976)).

Another possibility comprises incubating in each case one polynucleotide sequence from the two DNA stands with a short overlapping segment in the presence of the four required deoxynucleoside triphosphates with a DNA-polymerase, for example, DNA-polymerase I, the Klenow fragment of polymerase I or T4 DNA-polymerase, or with reverse transcriptase. The two polynucleotide sequences are thereby held together in the correct arrangement by base pairing and are supplemented with the required nucleotides by the enzyme to give a complete double-strand DNA (Narany et al., *Anal. Biochem.* 121, 365 (1982)).

Another suitable method for obtaining the DNA coding for a polypeptide comprises isolating the DNA from the genomic DNA of a tissue or cell culture or microorganism, lysing the cells e.g. with SDS or proteinase K, or if desired mechanically, and deproteinising the DNA by repeated extraction with phenol.

The RNA can be preferably digested with RNase. The obtained raw DNA is partially digested with suitable restriction enzymes e.g. HaeIII and AluI and fragments isolated and multiplied in a suitable phage or cosmid, e.g. in charon 4A or EMBL-3 phage and assayed for the desired sequences e.g. with a radioactively labelled DNA probe.

The DNA coding for a desired polypeptide can also be obtained by reverse transcription of isolated mRNA into cDNA. This may be the preferred method if the DNA structure is not known. In this method the DNA is obtained from genomic DNA in a cDNA library via the mRNA. The cDNA library comprises the genetic information which is complementary to the mRNA isolated from cells.

To obtain a cDNA library, the mRNA is isolated from cells expressing the desired basic (possibly unmodified) protein. This mRNA is converted into double stranded cDNA.

Standard methods well known in the art are applied in the preparation of mRNA. The cell membrane is broken and the cell content released from which the mRNA is isolated. The cell membrane is preferably broken by physical methods or lysis with detergents such as SDS, guanidine thiocyanate, definite salt conditions or homogenization, preferably by mixing. The mRNA is isolated by the standard methods of phenol extraction, ethanol precipitation, centrifugation and chromatography, preferably a combination of several methods. Centrifugation is preferably done over gradients, for example over a CsCl gradient. For chromatography, preferably columns are used, especially oligo-dT columns.

The total mRNA can be converted directly into Ds-cDNA following the methods of the art. Preferably the mRNA coding for a desired polypeptide is further enriched using several techniques, such as electrophoresis, chromatography and centrifugation, preferably sucrose gradient centrifugation.

Fractions containing mRNA coding for a desired polypeptide can be detected by various methods, such as in vivo or in vitro translations, followed by detection of a relevant activity or, when the nucleotide sequence is known, by hybridization with an oligonucleotide probe.

In vivo translation systems can be prokaryotic or eukaryotic systems. A preferred in vivo translation system is the Xenopus laevis oocyte system (see Maniatis et al., *Molecular Cloning, A Laboratory Manual*, Cold Spring Harbor Laboratory (1982)). In vitro systems are, for example, wheat germ and rabbit reticulocyte lysates, both of which are commercially available.

From any pool of mRNA derived from unfractionated or fractionated mRNA, ds-cDNA can be obtained by the well known methods of the art (preferred general methods are described in Maniatis et al. (supra), Okayam and Berg, *Molecular and Cell Biology* 2, 161–170 (1982) and Heidecker, *Nucleic Acid Research* 11, 4891–4906 (1983)). In general, the mRNA is converted first to ss-cDNA using reverse transcriptase or DNA-polymerase I (Klenow fragment). Two methods are alternatively used for priming the synthesis of the ds-cDNA. The first method was the natural loop formation of the ss-cDNA. The second method is that of tailing the ss-cDNA with a homopolymeric tail such as poly-dC or poly-DT.

The mRNA fraction of which the corresponding polypeptide shows the highest activity in the detection system is transcribed into the complementary cDNA by methods well known in the art. The mRNA and oligo-dT as a primer are mixed, dNTPs are then added as starting material and the synthesis of the cDNA-mRNA hybrid molecule is realized by the enzyme reverse transcriptase. The RNA molecules are degraded by addition of NaOH. DNA polymerase is admixed, preferably the Klenow fragment of the DNA polymerase I, and the mixture is incubated at a suitable temperature, preferably 12°–15° C. The mixture is incubated with nuclease S1 and the ds-cDNA corresponding to the mRNA coding for a desired polypeptide is obtained.

For amplification the obtained ds-cDNA can be spliced into suitable vector e.g. the plasmid pUC-KO and the obtained hybrid vector multiplied by use of a suitable host, e.g. *E. Coli* HB101. Reisolation of the hybrid vectors, and recovering the isolated cDNA therefrom allows a structure determination of the DNA coding for a desired polypeptide.

Preparation of a Hybrid Vector

A hybrid vector of the invention can be prepared by splicing a DNA coding for a polypeptide of the desired sequence into a suitable vector.

Suitable vectors are carriers for integrated passenger DNA, which can be used to transform a host microorganism.

Suitable as vectors are plasmids derived from microorganisms which in an untransformed state produce polypeptides which contain dehydroamino and/or sulfide groups. Suitable vectors carry the insert DNA at a defined position.

In general, such vectors may contain a replicon and a control sequence, i.e. a promoter, which are derived from the host cell or a species compatible with the host cell in which they are used. The vector ordinarily carriers a replicon site and may contain sequences (marker genes) which are capable of providing phenotype selection in transformed cells. Suitable marker genes may provide antibiotic resistance or resistance to heavy metals or they may complement a genetic defect of the host. Further useful sequences in such vectors are enhancer and activator sequences.

One suitable starting vector is a 54 Kbp plasmid pEpi32 from the strain *Staphylococcus epidermidis* DSM 3095. This plasmid, which is characterized below, contains the epiA gene encoding for a 52-prepeptide, which is processed to a tetracyclic 21-peptide amide antibiotic. A vector carrying a passenger DNA is designated a hybrid vector.

The desired DNA is spliced into the starting vector by conventional methods.

A starting plasmid for example can first be linearized by a suitable restriction enzymes, e.g. the plasmid pEpi32 by HindIII, BamHI and EcoRI, then d/G-tailed in the presence of dGTP and the terminal deoxynucleotidyl transferase. The double stranded cDNA insert is dC-tailed in the presence of dCTP and terminal deoxynucleotidyl transferase. Combining both cDNA and vector results in the hybrid vector. Bacteriophages, such as lambda, are preferred for constructing genomic libraries. The lambda cloning systems are described by Maniatis (supra). The suitable vector DNA is digested to completion with the appropriate restriction enzyme, and the left and right arms are separated from the central fragments by velocity gradient centrifugation or gel electrophoresis. Another method is to digest parts of the stuffer fragments with restriction enzymes which lack recognition sites in the left and right arms. The isolated genomic DNA can be partially digested to fragments of 13–20 kb in length. Afterwards the arms are ligated with the fragments of foreign DNA having termini compatible with those of the arms.

The appropriate DNA insert is recloned from the original vector used for the original cloning, into a suitable expression vector. To this end appropriate restriction enzymes are used, possibly in combination with oxonucleones, to produce the desired DNA fragments.

The DNA insert may be subcloned into a multiple site of a suitable well known plasmid vector e.g. derivatives of pC194, pT181 and pUB110 at the restriction sites HindIII/BamHI/EcoRI.

The method of the invention can thus be used to prepare derivatives of known peptides and hormones, in which a cysteine residue in the unmodified peptide is replaced by sulfide-bridged amino acids and serine and threonine are replaced by corresponding dehydroamino acid residues.

These fragments are integrated into an appropriate expression vector by using the cohesive ends directly or by the addition of appropriate chemically synthesized oligonucleotide bridges. For the modification of the ends for example HindIII and BgLII can be used. The method is not limited to any special restriction enzymes. Any desired link can be made between the expression vector and the DNA insert using suitable restriction enzymes in combination with chemically synthesized oligonucleotides.

Appropriate DNA inserts can also be obtained which code for polypeptide having site directed mutagenesis.

A variety of methods may be used to induce mutations of underlying DNA so as to prepare the desired mutants.

One method may comprise first inserting a fragment of a native or basic gene, containing sequences coding for the region to be mutated, into the replicative form of a phage, e.g. phage MI3mp8 to form MI3mp8PA. A synthetic oligonucleotide, complementary to the inserted sequences but containing one or more nucleotidetriplets which code for the amino acid to be substituted, is then annealed to the single stranded form of MI3mp8A to form a double stranded region. This region serves as a primer for DNA polymerase I synthesis of the remaining complementary strand. After replication and identification, the mutant sequence may be further modified or used to construct a suitable vector for expressing the mutated polypeptide.

In the work carried out on epidermin a wobbled DNA probe 5'-GTG(A)CAT(G/A)ATG(A)AAT(C)TT-3' (SEQ ID NO:2) deduced from a suitable pentapeptide segment of the proposed pre-sequence of epidermin LysPheIleCysThr (SEQ ID NO:3) was prepared. This DNA probe was hybridized against plasmid DNA from *S. epidermin* DSM 3095.

Restriction analysis of the isolated plasmid reveals seven DNA fragments with EcoRI (16, 11, 10, 6.5, 5.5., 3.5 and 2.5 kbp), nine DNA fragments with HindIII (17, 14, 10, 5.3, 2.8, 1.8, 0.8, 0.6 and 0.5 kbp) and five DNA fragments with BamHI (20, 19, 10, 3 and 1 kbp).

A 5.4 kbp HindIII fragment was subcloned and subjected to rehybridization whereby the structure gene epiA was located within a 2.2 kbp EcoRI/BglII fragment.

A mixture of 24 different 14-mers was used as a hybridization probe. The probe was applied in a 30-fold excess as a sequencing primer in accordance with the techniques described in Novick et al. *Ann. N.Y. Acad. Sci.* 182, 279–294 (1971), Southern, *J. Molec. Biol.* 98, 503–517 (1975) and Heinrich et al., *Molecul. gen. Genet.* 209, 563–569 (1987). The peptide sequence of epidermin allowed identification of the open reading frame. A single methionine codon is an appropriate distance to a Shine-Daigaro sequence. The structural gene of pre-epidermin terminates at the TAA stop codon, hence pre-epidermin consists of 52 amino acids (FIGS. 1A and 1B (SEQ ID NO:10)) and it is processed to the epidermin between $Arg^{-1}$ and $Ile^{+1}$. Thus, as can clearly be seen, pre-epidermin is not a degradation product of a larger protein but is coded by a distinct structural gene.

Thus, it is apparent that, unexpectedly, the precursor protein of the antibiotics is coded by distinct structural genes.

Figure 2B:
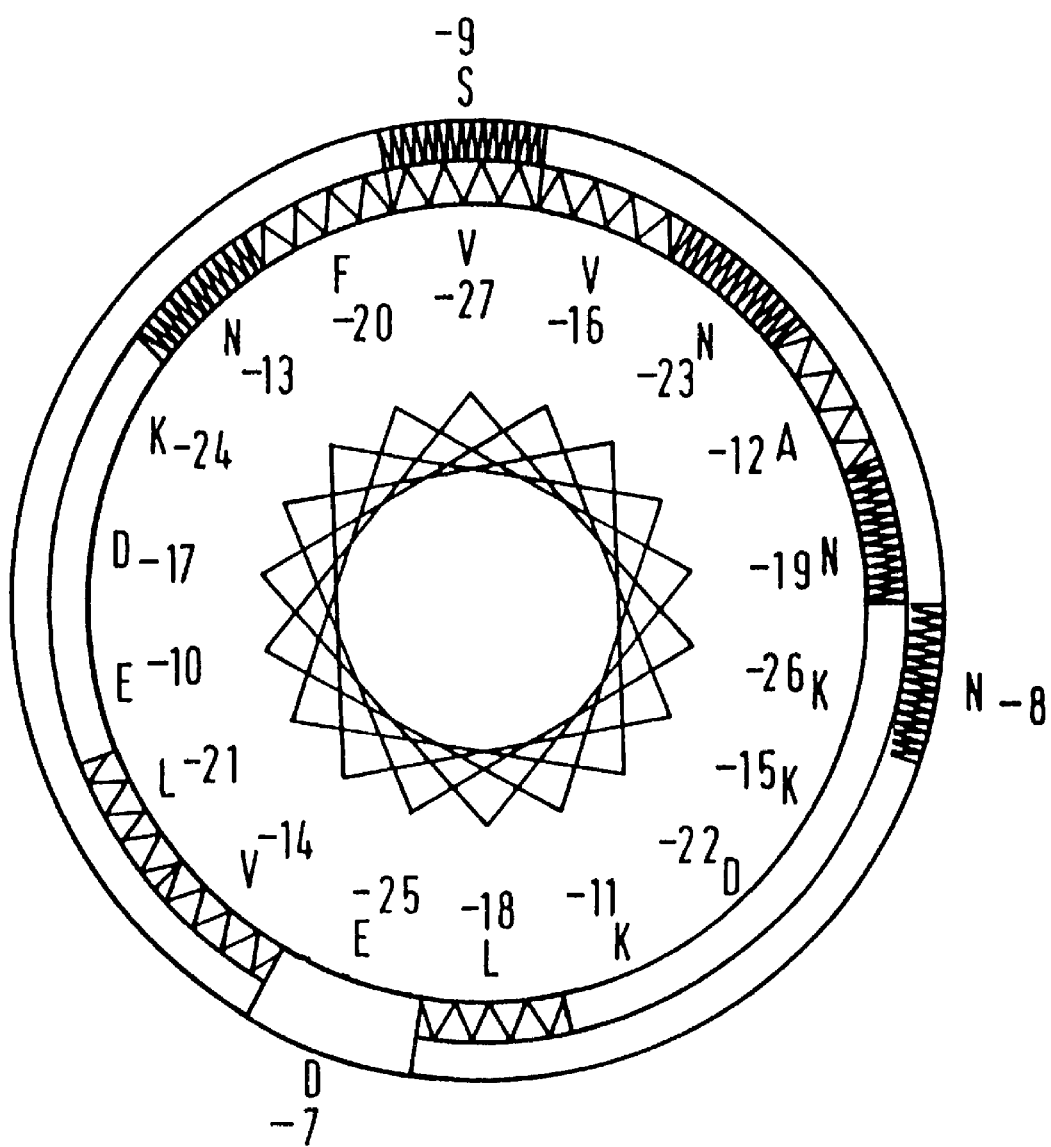
FIG. 2B depicts a helix wheel plot for pre-epidermin showing that the N-terminus may partially adapt an amphophilic α-helical conformation in an appropriate environment.

A combination of prediction profiles for secondary structure ($\alpha,\beta$, turns), flexibility, hydropathy, hydrophilicity (FIG. 2A (SEQ ID NO:11)) and helix wheel plot were made using a Hycon program (FIG. 2B). A high $\alpha$-helix probability is predicted for pre-epidermin −30 to −8 whereas the C-terminal part 1–22 which corresponds to pro-epidermin exhibits very high turn probability. Moreover, the prediction plot shows clearly, that the N-terminus −30 to −1 highly hydrophilic, whereas the C-terminal part is more lipophilic. The N-terminal part −30 to −8 seems to fold partially into an amphophilic $\alpha$-helix.

The N-terminal segment of pre-epidermin −30 to −1 does not contain any cysteine residues, whereas the C-terminal segment 1–22 contains the four cysteine residues, involved in sulphide bridge formation. Sequence −30 to −1 included many cleavage sites for endoproteases whereas even in the pre-epidermin state, sequence 1–22 is highly resistant to proteolytic degradation.

The mature antibiotic can only be attacked by trypsin at Lys in position 13. The processing site $Arg^{-1}$-$Ile^{+1}$ is hydrophilic and accessible, due to the turn forming $pro^{-2}$ residue.

Figure 3:
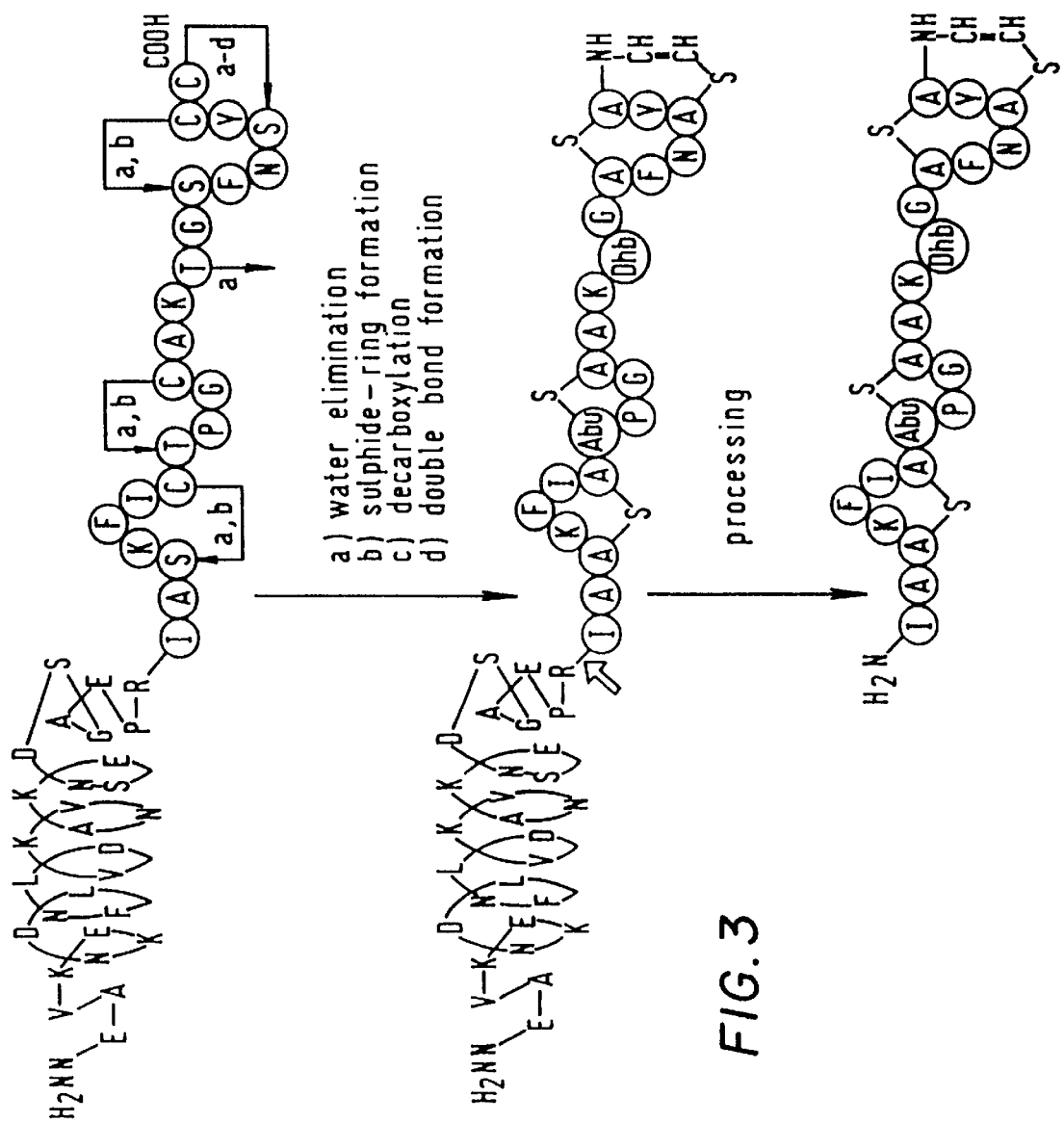
FIG. 3 (SEQ ID NO:12, 13, 14) depicts a postulated naturation procedure for epidermin. The translated polypeptide (pre-epidermin) (SEQ ID NO:12) consists of 52-amino acid residues. Structure predictions indicate a partially α-helical N-terminus from which residues −30 to −10 may form an amphilphilic α-helix conformation. Water elimination occur at the indicated Ser and Thr residues (a). With the exception of $Thr^{+14}$, water elimination is followed by sulphide ring formation (b) and at the C-terminus, decarboxylation (c) and double bond formation (d) to produce pro-epidermin (SEQ ID NO:13). The pro-epidermin (SEQ ID NO:14) structure is then processed by proteolytic cleavage to produce epidermin.
Figure 4:
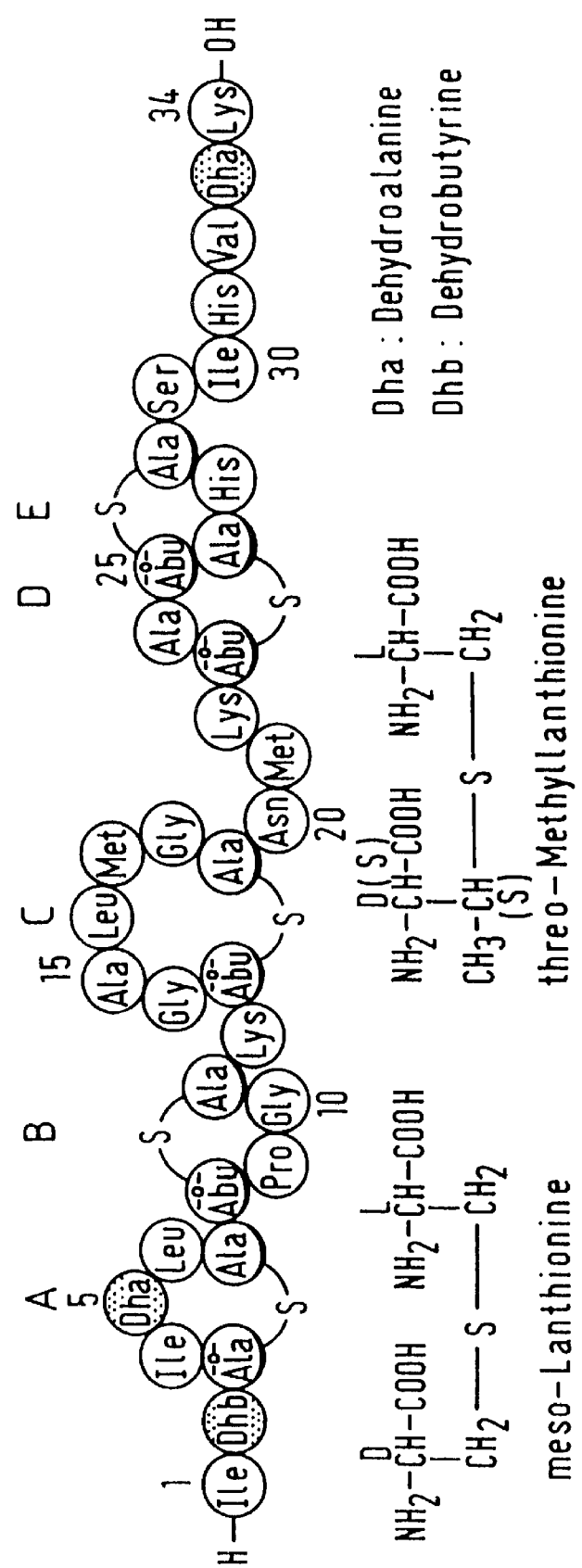
FIG. 4 (SEQ ID NO:15) depicts the structure of epidermin. The ring structures are designated as A, B, C, D and E. The structures of the amino acids mesolanthionine and threo-methyllanthionine, are set forth.

The various enzymatic reactions which occur in the production of the antibiotics such as epidermin include modifications of the pro-polypeptide part 1–22; cleavage of the N-terminal prepeptide fragment −30 to −1 and secretion of the matured antibiotic (see FIGS. 3 (SEQ ID NO:12, 13, 14) and 4 (SEQ ID NO:15)).

The enzymatic modifications occur before cleavage of the prepeptide fragment. Enzymatic modification includes the elimination of water from Ser and Thr residues in position 5, 16, 19 and 8, 14 respectively to form dehydroalanine and dehydrobutyrine residues. Addition of thiol groups of Cys residues in position 2, 11, 21 and 22 to the C=C double bonds, also occurs, yielding the meso-lanthionine or (2S 3S, 6R)-3-methyl-lanthionine bridges. In addition, decarboxylation of residue 22 and double bond formation yields the C-terminal S-(2-aminovinyl)-D-cysteine. The reaction of C-terminally situated cysteine thiol groups with N-terminally located dehydroamino acids occurs with complete stereospecificity in epidermin, nisin and subtilin. Accordingly, during modification these elimination-addition reaction imply a reversal of configuration of the C$\alpha$ carbon atoms at pre-epidermin residues L-Ser and L-Thr to give D-configured C$\alpha$ atoms. On the other hand, the L-configuration of the cysteine halves is still maintained.

The four sulphide rings are also formed, subsequently at the same catalytic site, which is supported by the interaction with the N-terminal amphophilic $\alpha$-helix. Only $Thr^{+14}$ dehydrates without finding a cysteine. This position ($Lys^{+13}$-$Dhb^{+14}$) constitutes the enzymatic cleavage site at which trypsin inactivates the antibiotic epidermin. During sulphide ring formation C-terminal rigidity and hydrophobicity increases and may favor interaction of pro-epidermin with the lipid bilayer and may induce translocation.

Finally, the hydrophilic $\alpha$-helical N-terminus −30 to −1 is cleaved by a specific protease at the characteristic cleavage site described above.

Using the techniques described above plasmids coding for lantibiotics can be modified either by mutation of the gene coding for the respective polypeptide or by replacement of such a gene by a gene coding for a different polypeptide and used to transform the original host or a different host, provided such host also, in its native state, is capable of expressing a lantibiotic.

Generally speaking, where the original functional gene codes for a pre-sequence, as discussed above for example in the case of epidermin, the DNA sequence coding for such a pre-sequence may be retained in the modified plasmid; in this case the DNA-sequence for the new, or mutated pro-polypeptide will be positioned directly upstream of the pre-sequence DNA similarly to the original pro-polypeptide sequence.

Cultivation of a bacterial host according to the present invention may be carried out under conventionally used cultivation conditions as described for instance in our co-pending British Patent Application No. 8811760.1 which was filed on 18th May 1988 and in European Patent Application Publication No. 0 181 578. Purification and isolation of the desired protein may also be carried out using the techniques or suitable modifications thereof described in the foregoing patent applications for epidermin and gallidermin, including the use of adsorbents, ion-exchange resins and if desired HPLC.

The process of the invention can be applied to the formation of novel compounds for experimental purposes, or to the formation of known compounds or derivatives of known compounds in new hosts. For instance a plasmid containing the gene coding for epidermin can be used to transform the species *Streptococcus lactis* to produce epidermin from that host, or the gene coding for Gallidermin (see our co-pending British Patent Application referred to above) can be used to replace the gene coding for the pro-polypeptide for epidermin in e.g. plasmid pEpi32 and used to transform *Staphylococcus epidermidis* DSM 3095 to produce gallidermin from this host. Similarly other biologically active peptide derivatives containing dehydroamino acid residues and/or lanthionine bridges and/or methyl-lanthionine bridges can be produced, such as derivatives of hormones such as human insulin, oxytocin, vasopressin, peptide antibiotics, hormone inhibitors such as elastase inhibitor and fibrinolytically active agents such as human tissue plasminogen activator. Such derivatives, as well as retaining biological activity of the parent compound can have increased stability and improved half-lives.

Ideally the DNA coding for the desired pro-polypeptide should include codons for cystein and serine and/or for cysteine and threonine for the formation of thioether bridges.

For relatively short chain polypeptides these respective codons should normally be no more than eight and preferably no more than six codons apart, inclusive, although it is envisaged that, depending upon the steric conformation of the final polypeptide molecule much greater spacing is possible.

In respect of the formation of dehydroamino acids these will usually be derived from serine and threonine and, accordingly the DNA coding for the desired pro-polypeptide will include codons for such amino acids.

Figure 5B:
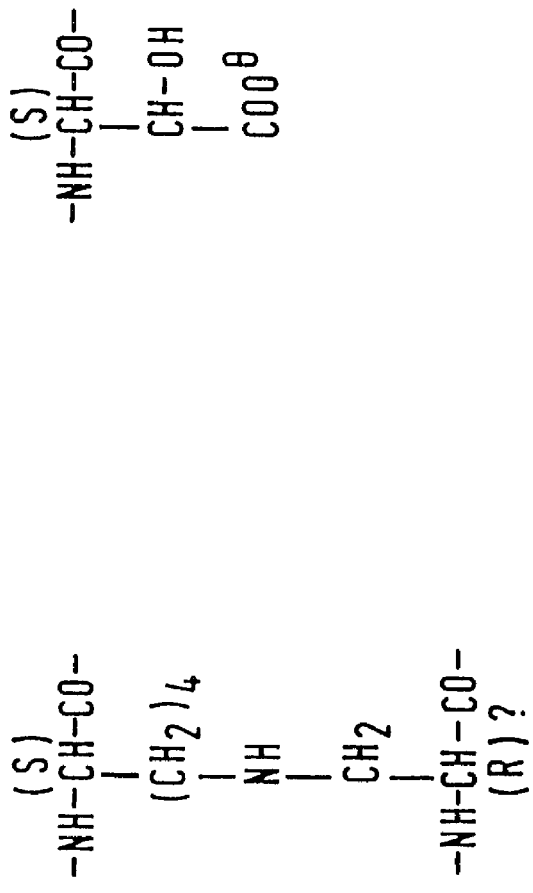

Amongst the unusual amino acids which may be present in a polypeptide produced according to the present invention are, dehydroalanine, 2,3-dehydro-2-aminobutyric acid, meso-lanthionine, (2S, 3S, 6R)-3methyl-lanthionine, S-(2-(Z)-aminovinyl)-D-cystein, lysinoalanine and β-hydroxyaspartic acid; the structure of these residues are shown in FIG. 5.

We have unexpectedly found that the multi enzyme complex responsible for the posttranslational modification of pre-epidermin is located on the 54 kb plasmid pTü32 of *Staphylococcus epidermidis* Tü 3298/DSM 3095.

The six genes (ORFs) responsible for the production of epidermin are designated herein epi A, B, C, D, Q and P and are clustered within 8 kb and the proteins for which they code are designated Epi A, B, C, D, Q and P respectively; epi A encodes the 52 amino acid-long pre-epidermin. As described below, epi B, C and D are involved in the four enzymatic modification reactions (i) water elimination by a serine/threonine dehydratase, (ii) sulfur addition by a lanthinonine synthase, (iii) C-terminal decarboxylation by a cysteine decarboxylase and (iv) double bond formation. Epi P protein is believed to be responsible for cleaving the mature epidermin from the N-terminal leader peptide, based on its striking homologies with the essential domain of serine proteases (Koide et al., *J. Bacteriol.* 167:110–116 (1986); Meloun et al., *FEBS Lett.* 183:195–200 (1985); and Stahl et al., *J. Bacteriol.* 158:411–418 (1984)) whilst Epi Q is believed to be a regulatory protein regulating epidermin biosynthesis, based on its distinct homology to the pho B gene of *E. coli* (Makino et al., *J. Mol. Biol.* 190:37–44 (1986)), the fact that both proteins are of a similar size with 205 (epi Q) and 229 (pho B) amino acid residues, the observed homology of 24.2% extending over the 153 C-terminal amino acid residues and the hydrophilicity plots of both proteins.

As a result of the unexpected finding of the entire genetic information for the epidermin biosynthesis and the elucidation of the genes for the proteins epi B, C, D, Q and P, it is now possible to obtain the isolated DNA coding for the proteins, and to construct plasmids containing one or more of these genes so that upon cultivation of a host containing such plasmids one of these proteins alone or predetermined combinations of the proteins may be expressed and subsequently isolated.

The present invention therefore includes DNA sequences encoding respectively for the protein Epi B or Epi C, or Epi D, or Epi P or Epi Q. These sequences may be isolated DNA either single or double stranded, obtained by cleavage of and isolation from pTü32 in known manner or obtained by chemical synthesis or any other conventional procedure. The DNA may also be integrated in a plasmid, suitably an expression plasmid and under the control of a promoter regulator; such constructs when transformed into a suitable host which is then cultivated will express the protein Epi B, Epi C, Epi D, Epi P or Epi Q or combination of these proteins according to which DNAs were ligated into the plasmid. Alternatively plasmid pTü32 may be treated with suitable restriction nucleases to excise one or other of the DNA sequences, followed by religation after any necessary modification of the free ends of the digested plasmid, so as to create a modified plasmid containing DNA sequences coding for predetermined ones of epi B, C, D, P and Q.

A further variant comprises the substitution of the gene coding for epidermin in pTü32 with a DNA sequence coding for a predetermined amino acid sequence whereby cultivation of a suitable host with the modified plasmid will result in expression of a protein different from epidermin.

It is thus possible to substitute a DNA sequence encoding for gallidermin or mutant epidermin or other lantibiotic or other protein, for the epidermin coding sequence in pTü32 whereby the resulting plasmid can be transformed into a suitable host which may be a host normally incapable of producing a lantibiotic or any of the proteins Epi B, C, D, P or Q and to cultivate the host under conditions whereby the substituted DNA sequence and the genes epi B, C, D, P and Q are expressed, so as to obtain a protein which is gallidermin, mutant epidermin or other protein containing at least one structural feature of a lantibiotic.

Alternatively the genes coding for the proteins Epi B, C, D, P or Q may be inserted into a suitable vector, together with a DNA sequence encoding a predetermined amino acid sequence, the genes coding for the Epi proteins and the predetermined amino acid sequence being operably connected with suitable promoter regulator functions, the resulting plasmid being transformed into a suitable host which may be a host normally incapable of producing a lantibiotic or any of the proteins Epi B, C, D, P or Q, and the host cultivated so that the inserted genes cause the expression of a protein derived from said predetermined amino acid sequence but containing a lantibiotic structural feature, which protein may be gallidermin, epidermin, mutant epidermin, or another protein.

The present invention thus also includes within its scope DNA sequences capable of hybridizing, preferably under stringent conditions, with the DNA sequences described herein and coding for proteins having substantially the activity of the proteins Epi B, C, D, P or Q. Stringent hybridization conditions select for DNA sequences of greater than 85% or, more preferably, greater than about 90% homology. Screening of the cDNA library may be carried out under highly stringent conditions according to the method described in European Patent Application No. 88 119 602.9 and Kashima et al. (*Nature* 313:402–404 (1985)). The DNA sequences capable of hybridizing under stringent conditions with the DNA sequences disclosed in the present application may be, for example, allelic variants of the disclosed DNA sequences, may be naturally present in the particular microorganism but related to the disclosed DNA sequences, or may derived from other sources. General techniques of nucleic acid hybridization are disclosed by Maniatis, T. et al., *In: Molecular Cloning. a Laboratory Manual*, Cold Spring Harbor, NY (1982), and by Haymes, B.D. et al., *In: Nucleic Acid Hybridization, a Practical Approach*, IRL Press, Washington, DC (1985), which references are herein incorporated by reference. The proteins Epi B, C, D, P and Q are valuable and interesting new reagents potentially useful in the preparation of novel proteins or other substances containing structural features such as dehydroalanine, dehydrobutynine, meso-lanthionine, 3-methyl-lanthionine, and S-(2-aminovinyl)-D-cysteine.

As such, they may be utilized as isolated proteins, or as chemical catalytic reagents in chemical synthesis procedures to investigate the extracellular processing of proteins by such enzymes.

The invention also relates to the proteins Epi B, C, D, P and Q in substantially pure form. By the term "substantially pure" is intended that the protein is free of the impurities that are naturally associated therewith. Substantial purity may be evidenced by a single band by electrophoresis.

The polypeptides of the invention may be isolated and purified from the above-described recombinant molecules in accordance with conventional methods, such as extraction, precipitation, chromatography, affinity chromatography, electrophoresis, or the like. Preferably, the polypeptides are produced as part of a fusion protein which further comprises an auxiliary protein. Such auxiliary which facilitates the isolation and purification of the polypeptide of interest. Such auxiliary proteins include, for example, typical secretion signals, the maltose binding protein from E. coli, or protein A. Methods for preparing fusion proteins comprising protein A, the purification thereof by immunoaffinity chromatography, and the cleavage thereof to release the protein of interest is taught for example, in PCT Application Publication No. WO84/03103 (1984).

A necessary condition to permit cleavage of the fusion protein is that it contains a unique cleavage site which may be recognized and cleaved by suitable means. Such a cleavage site may be a unique amino acid sequence recognizable by chemical or enzymatic means and located between the desired protein and the auxiliary protein. Such a specific amino acid sequence must not occur within the desired protein or auxiliary protein. Examples of enzymatic reagents include proteases such as collagenase which may recognize the amino acid sequence $NH_2$-Pro-X-Gly-Pro-COOH, (SEQ ID NO:4) wherein X is an arbitrary amino acid residue, e.g. leucine; chymosin (rennin) which cleaves the Met-Phe bond; kallikrein B which cleaves on the carboxyl side of Arg in X-Phe-Arg-Y; enterokinase which recognizes the sequence X-(Asp)$_n$-Lys-Y, wherein n=2–4, and cleaves it on the carboxyl side of Lys; thrombin which cleaves at specific arginyl bonds. Examples of chemical agents which may be used to cleave the fusion proteins include cyanogen bromide which cleaves after Met; hydroxylamine which cleaves the Asn-Z bond wherein Z may be Gly, Leu or Ala; formic acid which in high concentration (~70%) specifically cleaves Asp-Pro.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

Example 1

1. Overproduction of gallidermin

A DNA fragment containing the open reading frame of gallidermin can be cloned in Staphylococcus epidermidis DSM 3095, the epidermin producing strain by using a medium copy plasmid such as pC194, pE194, pUB110, pT181 or pMK148 gallidermin. An increase of the gene doses usually correlates with an increase of product production; the correlation is not necessarily linear. High copy number plasmid derivatives of pC194 or pT181 can be used as cloning vehicles too.

2. Exchange of leader sequence

The leader-sequence of epidermin corresponding to amino acids −1 to −30, is involved in the secretion of epidermin. The sequence can be used to secrete other peptides in S. epidermidis such as gallidermin.

The leader-sequence DNA can be made portable by inserting respective linkers at the beginning and at the end of its sequence. Thus the leader sequence DNA can be isolated in large amounts from the plasmid and can be inserted at respective positions of other peptides and proteins. The leader-sequence DNA can also be produced by chemical synthesis.

Example 2

Production of Gallidermin using S. epidermidis as host

Figure 6:
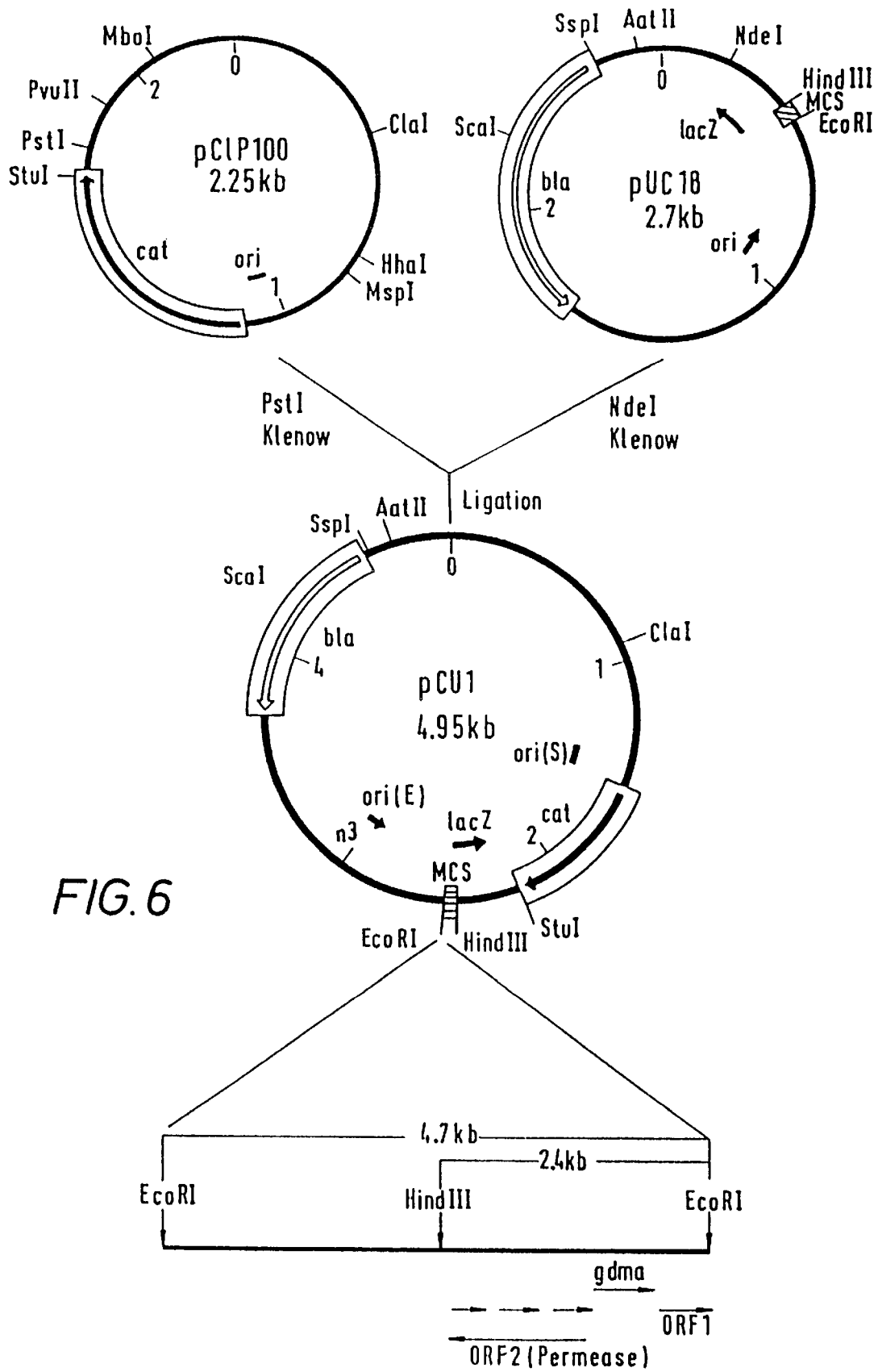
FIG. 6 depicts a schematic representation of the process for preparation of the pCUI plasmid from pCLP100 plasmid and pUC18 plasmid.

1. Preparation of plasmid (see FIG. 6)

a) Plasmid pCUI was prepared by ligating Pst1 digested pCLP100 and NdeI digested pUC18 using Klenow as described in the thesis "Molekular genetische Untersuchungen zur plasmidkodierten Arsenit und Arsenatrestistent bei Staphylococcen", by Dr. Ralf Rosenstein (available from the Technische Universitat, Munich, West Germany). The resulting plasmid was then digested with EcoR1.

b) Chromosomal DNA was isolated from S. gallinarum (DMS 4616) and was digested with EcoR1. A 4.7 kb fragment containing the gallidermin structural gene in a 2.4 kb long sequence between HindIII and EcoR1 restriction sites was isolated using as a primer the sequence.

5' CAC ATC CAG GAG TAC 3' (SEQ ID NO:5)

c) The 4.7 kb Fragment was then ligated into the EcoR1 site of the digested pCUI plasmid from step a) to give a plasmid designated pCUgdm1.

2. Preparation of a S. epidermis host

In this example a mutant strain of S. epidermidis DSM 3095 incapable of producing epidermin was isolated.

The mutagenesis was carried out on a strain which was characterized by chromosomally coded Rifampicin resistance (20 ug/ml).

S. epidermidis DSM 3095 grown on Agar plates was used to inoculate 30 ml basic broth medium which was cultivated overnight. 0.5 ml of the overnight cultivation was then used to inoculate 50 ml of production medium which was shake cultivated at 37° C. for three hours.

Cells were removed from the cultivation medium and suspended in 4.5 ml pre-warmed TM-Buffer (30 mM Tris-Maleate pH 6.5 (the resulting solution is designated Solution A)).

The solution A was checked for spontaneous mutations and for cell count ($1.25 \times 10^{10}$ cells/ml).

4 ml of solution A was thoroughly shaken with 1 ml ethyl methyl sulphonate (final concentration 47 $\mu$g/ml) and then maintained under shaking at 37° C. for one hour.

Cells were then extracted from the cultivation broth, washed twice in TM-Buffer and resuspended in 5 ml TM-Buffer (the resulting solution was designated Solution B and contained mutated cells).

Solution B was found to contain $2 \times 10^8$ cells/ml which corresponds to survival rate of 1.6%.

50 ml of solution B was added to 5 ml production medium and grown overnight at 37° C. (phenotypic expression). The resulting solution was designated Solution C. A cell count showed $7.3 \times 10^8$ cells/ml.

The solution was plated on BM-Agar plates and individual colonies were picked out. These were used to inoculate test plates (consisting of BM-Agar to which Micrococcus luteus has been laid on the surface). Those colonies which had no inhibitory effect on M. luteus were selected as non-producers of Epidermin.

BM Agar contains per liter:

10 gm Peptone No. 140

5 gm Yeast extract 1 mg Glucose 5 mg NaCl 1 mg $K_2HPO_4$ pH 7.5

A mutation rate of about 3% was noted.

The 45 non-producers which were found were sub-cloned 20 times to yield 16 stable non-producers All stable non-producers were found to contain the wild type plasmid pEpi32. From the restriction pattern this is identified as identical to the plasmid in the wild type strain.

Transformation of non-producing *S. epidermidis*

750 ml of BM-medium was inoculated with 5 ml of medium obtained by overnight cultivation of a stable non-producing strain, and the inoculated medium was shake cultivated in a 2 liter flask at 37° C. with a shake speed of 120 rpm.

The initial optical density of the inoculated BM-medium was 0.03–0.04. When the optical density had reached 0.45–0.55 the cells were removed by centrifugation in a GS.-3-Rotor at 8500 rpm for 15 minutes at 4° C. The isolated cells were then washed successively in 750, 350, 40 and 10 ml of 10% glycerin, suspended in 2–3 ml 10% glycerin, and frozen in 110 ml portions in ERGs at −70° C. The cell count amounted to $1-5 \times 10^{10}$/ml.

The frozen cells were thawed at room temperature for 5 minutes, then 50 μl of cell suspension was incubated in an ERG with 2 μl plasmid pCUgdm1 in TE-Buffer for 30 minutes at room temperature.

The mixture was then introduced into an electroporation cuvette having a 0.2 cm electrode gap and immediately electroporated. Thereafter the cells were rapidly resuspended in 950 μl SMMP50-medium, transferred into a 2.5 ml ERG and shaken for 90 minutes at 37° C. The ERGs were inclined at 45° in order to provide for a good aeration of the medium.

SMMP50-medium contains pro 100ml, 55 ml 2SMM, 40 ml 4 PAB and 5 mol 5% BSA. The 2SMM contains 1 mol saccharose, 0.04 mol maleic acid, 0.04 mol $MgCl_2$ and NaOH to pH 6.5. 4 PAB is a solution of 7 g/100 ml of Gibco antibiotic medium 3.

The cell suspension is diluted and spread on a BM-Agar containing gallidermin which is incubated for 20 hours at 37° C.

Testing of growing strains which produce gallidermin was carried out by selection of colonies from a *M. luteus* test plate and by cultivating the respective selected colonies and determining the presence of gallidermin by HPLC.

Three pCUgdm1 transformed mutants capable of producing gallidermin were located.

Determination of the presence of gallidermin produced by pCUgdm1 transformed *S. epidermin* a) Bio assay

FP-Agar was inoculated with *M. luteus* ATCC 9341 and incubated at 37° C. for 18 hours. Half of the produced culture was removed with a loop and suspended in 100 ml FP-medium and was cultivated for 8 hours at 36° C. The cultivation was stopped when the optical density reached 1.0. FP-Agar was inoculated with 0.5% of this suspension, each 10 ml was poured into a Petri dish and stored for 3 weeks at 4° C.

The Plate diffusion test was carried out as described in Zähner and Maas, "Biology of Antibiotics", Springer Verlag, Berlin 1972. 10 ul of culture filtrate from cultivation of the transformed *S. epidermin* was captured on a filter paper and dried. The paper was placed on the test plate which was then incubated for 24 hours at 37° C.

b) HPLC

The selected transformed strain was cultivated for 26 hours in the production medium. The culture broth was centrifuged for 10 minutes at 13.000 rpm.

The isolated culture liquid was then subject to HPLC on a SP 8.700 liquid chromatography apparatus (Spectra Physics, Darmstadt, FRG) using as the mobile phase A) $H_2O$ with 0.5% 70% perchloric acid and B) Acetonitrile. Column packings were Nucleosil −100 C-18 of grain size 7 um and column sizes 125 mm×4.6 mm I.D. and 20 mm×4.6 mm ID for the pre-column.

Gradients were as follows:

| time (min.) | A [%] | B [%] |
|---|---|---|
| 0 | 77.5 | 22.5 |
| 8 | 63.0 | 37.0 |
| 8.5 | 0 | 100 |
| 9.5 | 0 | 100 |
| 10 | 77.5 | 22.5 |
| 14 | 77.5 | 22.5 |

Figure 7A:
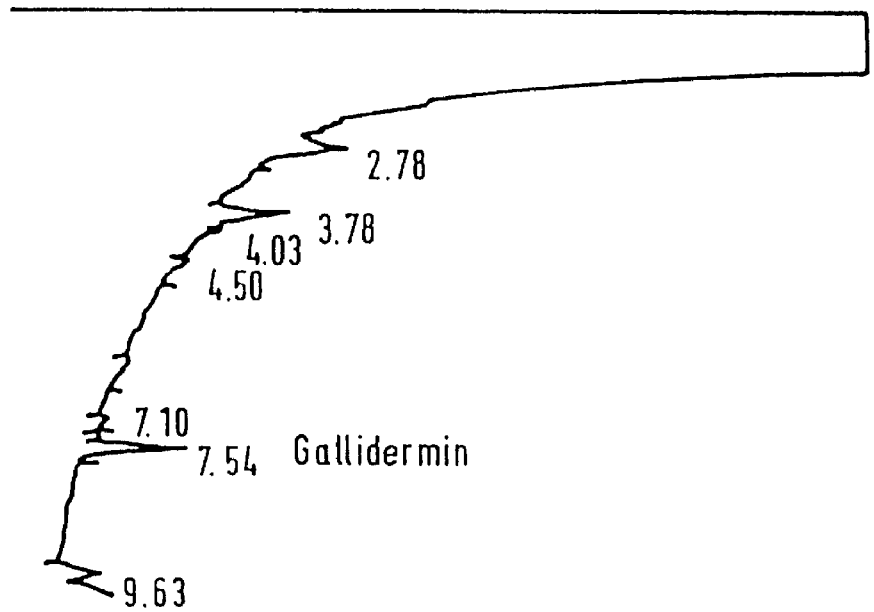
FIGS. 7A–7B depicts the elution pattern of the isolated culture medium prepared in Example 2.
Figure 7B:
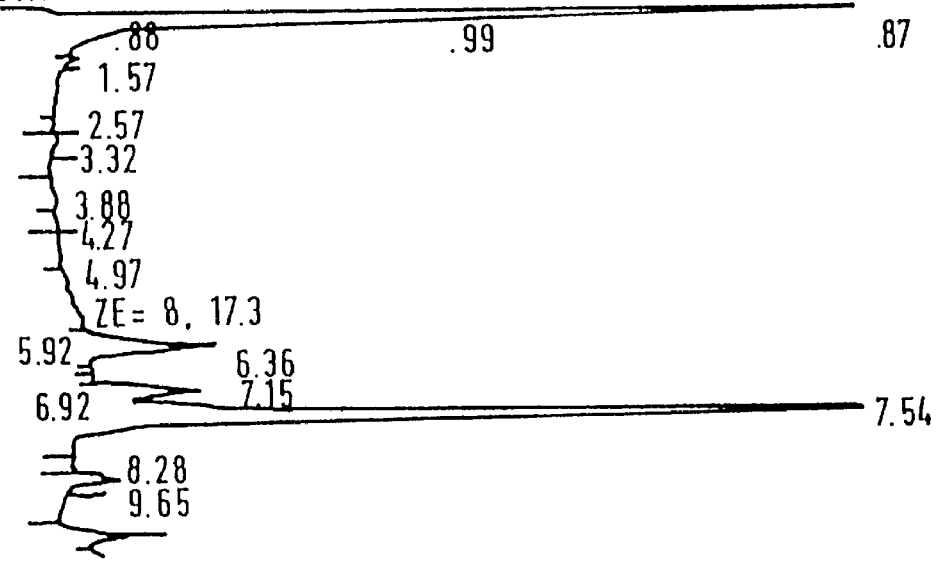

The resulting chromatogram is shown in FIG. 7A. A standard curve is shown in FIG. 7B showing that gallidermin elutes at 7.54 minutes.

The following were used as culture medium.

| 1. FP-Agar | |
|---|---|
| Meat extract | 4 g |
| Peptone | 10 g |
| NaCl | 3 g |
| $Na_2HPO_4$ | 5 g |
| Glucose | 10 g |
| Complex agar | 15 g |
| Water | 1 liter |
| pH | 7.2 |
| 2. FP-Medium | |
| Meat extract | 4 g |
| Peptone | 10 g |
| NaCl | 3 g |
| $Na_2HPO_4$ | 5 g |
| Glucose | 10 g |
| Water | 1 liter |
| pH | 7.2 |
| 3. Production medium | |
| Meat extract | 33 g |
| Malt extract | 30 g |
| NaCl | 40 g |
| Calcium Hydroxide | 3.8 g |
| Water | 1 liter |
| pH | 6.5 |

Example 3

Plasmid Isolation

Plasmid DNA from S. epidermidis Tü3298 was isolated according to a modified procedure of Norick el al., *Ann. NY-Acad. Sci.* 182:279–294 (1971). *S. epidermis* was grown on BM-media (1% peptone 140, Gibco, Neu-Isenburg, F.R.G., 0.5% yeast extract, Difco, Detroit, USA, 0.1% glucose, 0.5% NaCl and 0.1% $K_2HPO_4 \times 2H_2O$) until stationary phase. Cells were centrifuged and washed twice with 0.5M EDTA. The pellet was resuspended in 80 ml NaCl buffer (50 mM Tris/HCl, pH 7, 50 mM EDTA, 2.5M NaCl), 1.5 ml lysostaphin solution (0.5 mg/ml, Sigma, Heidelberg, F.R.G.) was added and the suspension was incubated at 37° C. for 20 min. Cells were lysed by the addition of 80 ml lysis buffer (50 mM Tris/HCl, pH 8, 300 mM EDTA, 500 mM Brij., 40 mM sodium deoxycholate and kept on ice for 1 h. The lysate was centrifuged (30 min, 13,000 rpm, 4° C.) and the supernatant was mixed with one quarter of its volume with 50% solution of PEG-6000. Plasmid DNA was precipitated at 4° C. overnight. The DNA suspension was centrifuged (20 min, 13,000 rpm, 4° C.), resuspended in 8 ml TE buffer and 50 μl of proteinase K solution (20 mg/ml) was added. After incubation at 37° C. for 15 min the DNA was precipitated with ethanol and further purified by CsCl centrifugation (1 g CsCl/ml, 40,000 rpm, 40 h, 20° C.).

RNA isolation and electrophoreses

S.epidermin was grown on SMS minimum medium (Terzaghi et al., Appl. Microbiol. 29:807–813 (1975)) and RNA isolated therefrom, using a modified procedure similar to that described for Bacillus subtilis RNA (Ulmanen et al., J. Bacteriol. 162:176–182 (1985)). Cells were lysed with lysostaphin (0.1 mg/ml) in protoplasting buffer and incubation was performed at 37° C. Total RNA was glyoxylated (McMaster et al., Proc. Natl. Acad. Sci. USA 74:4835–4839 (1977)) and separated on a 1.2% agarose gel using 10 mM $Na_2PO_4$, pH 7, as electrophoresis buffer. RNA was stained with ethidium bromide and blotted to a nitrocellulose membrane (Scheider and Schuell, Dassel, F.R.G.) by capillary transfer with 20×SSC buffer (0.15M NaCl, 0.015M tri sodium citrate, pH 9). 23SrRNA and 16SrRNA were used as size standards.

In vitro transcription

Single stranded RNA probes were obtained by cloning the respective fragment in a pSPT18/19 vector system (Boebringer Mannheim, Mannheim. F.R.G.). The plasmids were linearized with EcoRI or HindIII to get a linear DNA template. For transcription the protocol in Melton et al., Nucl. Acid Res 12:7035–7056 (1984), was modified according to the instructions of the commercial supplier. T7-RNA polymerase or SP6-RNA polymerase was used in the presence of $\alpha^{32}P$-CTP (800 Ci/mMol). Unincorporated ribonucleotides were separated from labeled RNA by Sephadex G50 chromatography.

Northern hybridization

RNA was transferred after electrophoresis according to Thomas, P.S., Proc. Natl. Acad. Sci. USA 77: 5201–5205 (1980). After 2 h incubation at 80° C. the filter was shortly incubated in 20 Tris/HCl, pH 8, at 100° C. to reverse glyoxylation. Afterwards filters were prehybridized at 42° C. in 50% formamide, 5×SSC (0.15M NaCl, 0.015M tri sodium citrate, pH 9), 50 $NaPO_4$, pH 6.5, 0.1% ficoll 400 (Pharmazia, Freiburg, F.R.G.), 0.1% polyvinylpyrollidone, 0.1% bovine serum albumin and 0.25 mg/ml denatured salmon sperm DNA for 2 h. After probe addition hybridization was performed in the same buffer at 42° C. for 12 h. Filters were washed once in 1×SSC, 0.1% SDS at 42° C. for 15 min and exposed to Kodak-X Omat films at −70° C. for 4 h. Thereafter filters were washed twice with 0.5 SSC, 0.1% SDS at 70° C. for 15 min and autoradiograms were exposed at −70° C. for 16 h. Next day washing was continued with 0.1×SSC, 0.1% SDS at 70° C. for 30–60 min and afterwards again exposed to Kodak-X Omat films at −70° C. for 3 days.

Southern hybridization

For southern hybridization (Southern, E.M., J. Mol. Biol. 98:503–517 (1975)) 5' labeled oligonucleotides were used as probes at 23° C. Oligonucleotides were labeled with gamma$^{32}$P-ATP using 4T polynucleotide kinase (Boehringer Mannheim, Mannheim, F.R.G.). Oligonucleotides and primers were synthesized on a 391 DNA synthesizer (Applied Biosystems, Weiterstadt, F.R.G.) and used without further purification.

DNA sequencing

DNA was sequenced radioactively and non-radioactively by the chain termination method (Sanger et al., Proc. Natl. Acad. Sci. USA 74:5463–5467 (1977)) using T7-DNA polymerase (Pharmazia, Freiburg, F.R.G.). Radioactive plasmid sequencing was performed as described in Hattori et al., Anal. Biochem. 152:232–238 (1984) with appropriate primers. The 3.6 kb BamHI/PstI fragment was sequenced non-radioactively on an Applied 373A DNA sequenator (Applied Biosystems, Weiterstadt, F.R.G.). The respective fragment was cloned in phagemid pBSK–/+. The construction was digested with BamHI and SacI and the linearized DNA was unibidirectionally digested from the 5' end with exonuclease III (Boebringer Mannheim, Mannheim, F.R.G.) to obtain a set of nested deletions which were treated with mung bean nuclease (Boehringer Mannheim, Mannheim, F.R.G.) to receive blunt ends. After electrophoresis (1% agarose gel) fragments of appropriate size were isolated from the gel, religated and transformed into E. coli strain XL-1 Blue. Single stranded DNA was isolated by using helper phage CSM13 and sequenced with Taq Polymerase (Promega, Freiburg, F.R.G.) according to the protocol of the commercial supplier.

Plasmid Construction

The staphylococcal tetracycline resistance plasmid pT181 has been sequenced (Kahn et al., Plasmid 10:251–259 (1983)) and found to contain a single NdeI site within the pre-gene which is not necessary for plasmid replication (Gennaro et al., J. Bacteriol. 169:2601–2610 (1987)). The multiple cloning site (mcs) of the E. coli vector pUCl9 (Yanisch-Perron et al., Gene 33:103–119 (1985)) was inserted into the NdeI site to form pT181mcs (see FIG. 14).

A staphylococcus-E. Coli shuttle vector, pCUI (FIG. 10) was constructed from pCLP100, a derivative of the staphylococcal chloramphenicol resistance plasmid pC194 (Horinouchi et al., J. Bacteriol. 150:815–825 (1982)) and the E. coli vector pUCl9. PCUI is stably maintained in both hosts with an insert size up to approximately 6 kb. pT181mcs and pCUI are compatible in staphylococci and were used to subclone DNA fragments from pTü32.

Figure 8C:
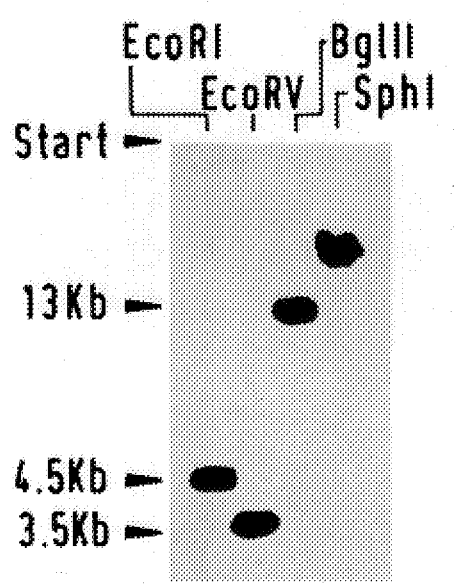

A HindIII fragment of pTü32 was cloned in pUCl9 and used as a probe in Southern hybridization to identify further restriction sites near the HindIII fragment (FIG. 8C).

The 13.5 kbp BglII fragment of the 54 kbp episomal element pTü32 from S. epidermidis was subcloned in pT181mcs to yield pTepi14 (FIG. 8A). For DNA sequencing subclones were made in the E. coli vector pUCl9 (Yaniscb-Perron et al., Gene 33:103–119 (1985)) and pBluescript II$^R$ (Stratagene, Heidelberg, F.R.G). Single stranded RNA probes were obtained from DNA cloned in vector pSPT18/19 (Boebringer Mannheim, Mannheim, F.R.G.).

Gene Analysis

Sequencing the DNA region adjacent to the epidermin structural gene, epi A (nucleotides 1381–1536 of SEQ ID NO:16), revealed five additional complete open reading frames epiB (nucleotides 1593–4662 of SEQ ID NO:16), epiC (nucleotides 4441–5805 of SEQ ID NO:16), epiD (nucleotides 5824–6366 of SEQ ID NO: 16), epiP (nucleotides complimentary to the DNA sequence 8379–6996 of SEQ ID NO: 16), epiQ (nucleotides complimentary to the DNA sequence 6983–6369 of SEQ ID NO: 16) inside the 13.5 kbp BglII fragment of pTü32.

As can be seen in FIGS. 9A–9U, directly adjacent to the sequence encoding for EpiA separated by only 50 nucleotides from the epiA ochre codon there is a large open reading frame preceded by a S/D sequence which spans 2,970 bp. A TTG codon for leucine which can also act as a translation start codon in staphylococci is in appropriate distance (86 p) to a S/D sequence. This open reading frame is designated epiB and as described herein can successfully be used for the complementation of epidermin biosynthesis mutants and an essential role in epidermin biosynthesis.

The protein coded for by epiB (SEQ ID NO:20), starting from the TTG (Leu) has a molecular weight of about 115 kDa, a net charge of −3 at pH7, and is moderately hydrophobic (41% hydrophobic residues) as may also be predicted from a hydrophilicity plot according to Kyte el al., J. Mol. Biol. 157:105–132 (1982).

At the 3' end of epiB no palindromine structure characteristic of transcription termination can be seen. There is, however, a 122 bp overlap with an other reading frame epiC, shifted by −1 base pair also to be seen in FIGS. 9A–9U.

We have established this to be no artefact by independently cloning and sequencing the respective 47 kbp HindIII-fragment twice from two independent plasmid isolations. This was also confirmed by mutant complementation with an epiC containing fragment as described herein.

Inside the overlapping region of epiB and epiC reading frames the first TTG codon (Leu) which is only 36 bp 3' to an AGGA element serves as a translational start codon, indicating that both reading frames overlap by about 40 codons. The actual amino-terminus of the EpiC protein was determined by N-terminal sequencing. Reading frame epiC encodes a protein with 455 amino acid residues commencing with starting codon TTG (Leu). The reading frame epiD directly follows 3' to epiC with a start ATG 86p 3' to a AGGAGG S/D sequence. 3' to epiD is a classical rho dependent transcription terminator structure; epiD encodes a protein of 181 amino acid residues with ATG (Met) on start codon.

None of the proteins Epi B (SEQ ID NO:20), Epi C (SEQ ID NO:21), Epi D (SEQ ID NO:22), Epi P (SEQ ID NO:24), and Epi Q (SEQ ID NO:23) show any similarity with protein sequences filed in the protein data bases Swiss Prot and Gene Bank, and thus represent unknown types of enzymes and regulatory proteins.

Transcription of the biosynthetic genes

Single stranded RNA probes were obtained by cloning the desired fragment in a pSPT 18/19 vector system (Boehringer Mannheim, Mannheim, F.R.G.) as described above.

Figure 10:
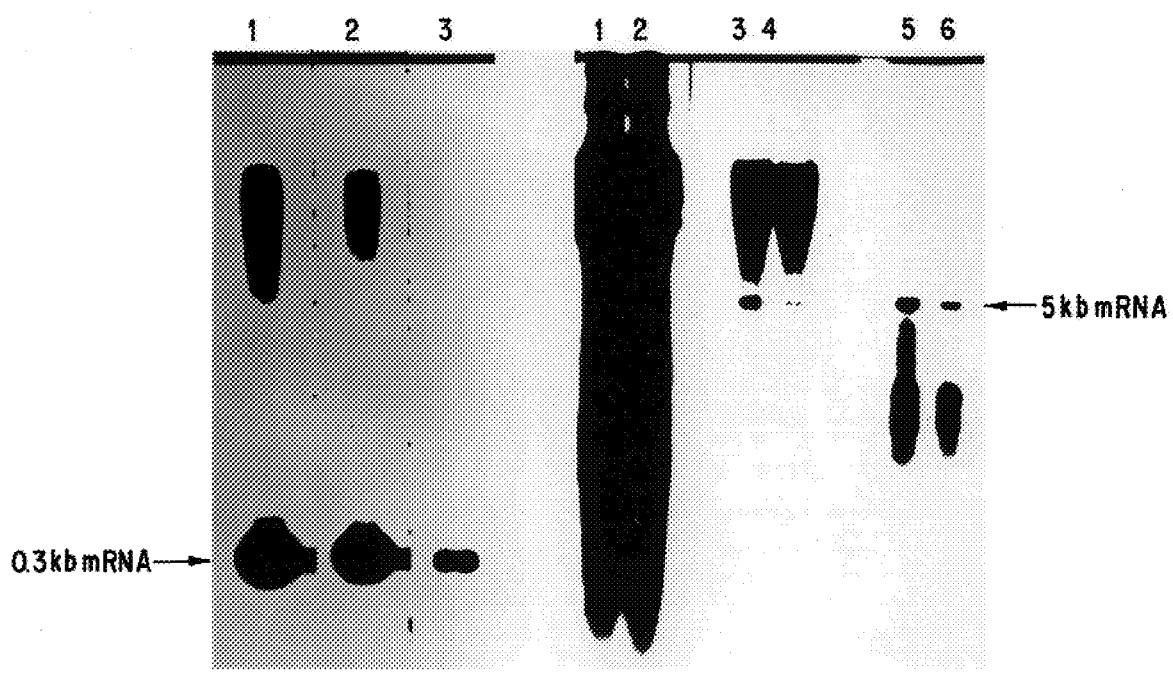

Two transcripts differing considerably in size were obtained as illustrated in FIG. 10. A hybridization probe specific of epiA identified a small transcript of about 300 bp. Transcripts of similar size were also found for the lantibiotics nisin (Buchmann et al., J. Biol Chem. 263:16260–16266 (1988)) and subtilin (Banerjee et al., J. Biol. Chem. 263:9508–9514 (1988)). Additionally a large transcript of approximately 5 kb can be identified with a hybridization probe specific for epiB. As there were no E. coli-like promoter sequences in front of epiB, whereas appropriate sequences were located 5' to epiA it can be seen that the epiA promoter acts as a promoter for a polycistronic mRNA.

Downstream open reading frames

The open reading frames epiP and epiQ are located on the opposite DNA to epiB, C and D with epiQ sharing a termination structure with epiD a perfect hairpin with a 6 bp loop.

Exactly within this loop structure the TAA stop codons for both reading frames epiD and epiQ share two of three nucleotides.

The epiP reading frame starts with an ATG codon which is in appropriate distance (6 bp) to a SID sequence. Taking the ATG codon as the translational start of epiP a protein of 461 amino acid residues with molecular weight of 51.8 kD. epiP shares characteristic homologies with the conserved amino acid motives of serine proteases (see FIGS. 11A and 11B) indicating that epiP is implicated in cleaving the natured lantibiotic from the modified prepeptide.

The epiQ reading frame also starts with an ATG codon and encodes 205 amino acid residues (FIGS. 9A–9U D(SEQ ID NO:22)). A S/D sequence is present 6 bp distance to the ATG codon and a molecular weight of 243 kD can be deduced from the DNA sequence. The epiQ protein shares characteristic homologies with PhoB (see FIG. 12) which is a positive regulatory factor for the phosphate regulatory of E. coli so that epiQ is implicated as a regulatory factor in lantibiotic synthesis.

Preceding epiP is an E. coli-like −10 region (5'-TATAAA) 12 bp in front of the S/D sequence which may serve as a promoter in staphylococci. The distance between the epiP stop codon and the ATG start codon of EpiQ is only 10 nucleotides and the epiQ S/D sequence overlaps with the epiP termination codon as shown in FIGS. 9A–9U.

5' to epiA, B, C, D a further reading frame with opposite orientation can be seen which potentially encodes a maximum of 148 amino acids. A characteristic S/D sequence is present but none of the previously described start codons for staphylococci (ATG, TTG, GTG). With a −1 frame shift a further reading frame follows which exceeds the isolated BglII fragment illustrated in FIGS. 9A–9U (SEQ ID NO:16).

These two reading frames are homologous to a single open reading frame, gdmY, identified adjacent to the structural gene of gallidermin (Schnell, N., Biosynthese der Peptid—Antibiotika Epidermin und Gallidermin; Doctoral Thesis, University of Tubingen, F.R.G. (1989)). The homologous reading frames on the S. epidermidis plasmid are designated epiY' and epiY".

Example 4

S carnosus TM300 was transformed with the plasmid pTepi14, prepared as described above, using standard techniques. The transformed strain was then grown on BM-media (see above).

The resulting transformants were found to be capable of inhibiting the epidermin sensitive tester strain Micrococcus luteus ATCC9341. In this assay 1 ml of an overnight culture of M luteus (adjusted to an $OD_{578}$ of 1.0) was added to 500 ml molten BM-Agar. Petri dishes usually contained 10 ml of this agar. Dilutions of S. epidermidis cultures were spread on the agar surface. Epidermin positive colonies were detected as a zero of growth inhibition of M. luteus around the colonies.

Cells were grown on 3% meat extract, 3.8% malt extract, 0.6% $CaCl_2 \times 2H_2O$ and 4.6% NaCl, pH6.5. According to the transformation used, tetracycline or chloramphenicol was added. After 24 h incubation (37° C., 160 rpm) in 500 ml Erlenmeyer flasks with one extension containing 100 ml medium, the culture both was centrifuged at 10,000 rpm in a Servall centrifuge for 10 min.

Figure 13C:
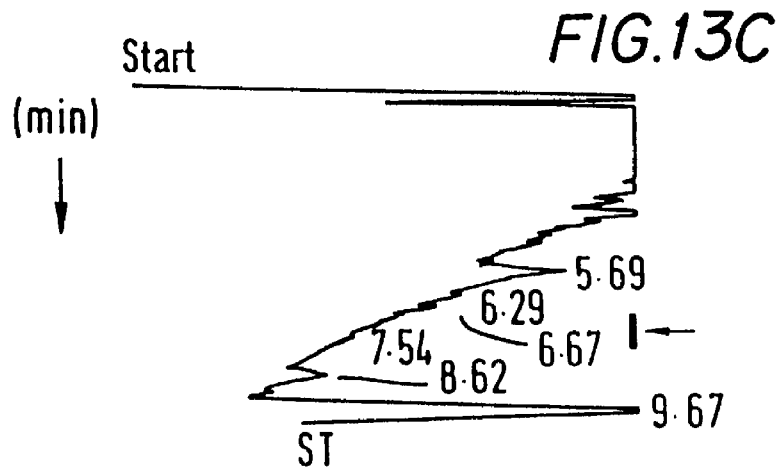

Supernatants of liquid transformant cultures were purified by adsorption chromatography (XAD 1180, impurities eluted with water/methanol (1:1) and epidermin eluted with methanol/0.1N HCl (9:1). after evaporation the eluate was adjusted with 3N NaOH to pH 3.5 and filled up with water to 10 ml) and detected by HPLC chromatography. The inhibitory activity co-migrated with mature epidermin at 6.75/6.76 min (see FIGS. 13A and 13B). Untransformed *S. carnosus* culture media treated similarly had no peak in this elution region (6.72 to 6.79 min, FIG. 13C). These results clearly confirmed the heterologous epidermin biosynthesis in *S. carnosus* and demonstrated that pTepi14 contains all information necessary for epidermin biosynthesis.

covalently closed (ccc) plasmids; when ligation products were used, transformants could only be isolated occasionally.

The results of the complementation studies are summarized in Table 1.

TABLE 1

Epidermin production by non-producing *S. epidermidis* mutants after transformatin with various pTepi14 DNA fragments

| Mutant | pTepi 14 | pTepi ABCDQ | pCUepi ABC | pTepi AB | pCUepi A1 | pCUepi A2 | pCUepi CDQ | pCUepi DQ | pCUepi Q | pCUepi B | Mutation locus |
|---|---|---|---|---|---|---|---|---|---|---|---|
| EMS 5  | + | + | + | + | + | − | − | − | − | − | epiA |
| EMS 6  | + | + | + | + | + | − | − | − | − | − | epiA |
| EMS 11 | + | + | − | − | − | − | + | + | − | − | epiD |
| EMS 12 | + | + | + | − | − | − | + | − | − | − | eipC |
| EMS 13 | + | + | + | − | − | − | + | − | − | − | epiC |
| EMS 18 | + | + | + | + | − | − | − | − | − | − | epiB |
| EMS 19 | + | + | + | − | − | − | + | − | − | − | epiC |
| EMS 33 | + | + | + | + | − | − | − | − | − | − | epiB |
| EMS 39 | + | + | + | − | − | − | + | − | − | − | epiC |
| EMS 45 | + | + | + | + | − | − | − | − | − | − | epiB | pCU: Fragments cloned in pCU1; pT: Fragments cloned in pT181mcs
+ complementation (epidermin production; − no complementation)

As pTepi14 contains the 13.5 kbp BglII fragment this indicates that the epiY' and epiY'' reading frames are not necessary for the production of epidermin in this system as epiY' lacks a translational start codon and epiY'' is incomplete on this fragment.

Example 5

A number of epi-mutants of *S. epidermin* Tü3298 were prepared by ethylmethane sulfonate (EMS) mutagenesis. This procedure was carried out according to Miller, J. H., *Experiments in molecular genetics*, Cold Spring Harbor Laboratory; Cold Spring Harbor, N.Y. (1972). The mutants were screened for epidermin production, or lack of epidermin production using the *M. luteus* assay described above. Epi mutants were transferred several times to test their stability. Of the 40 epi mutants isolated, only 10 were stable; the unstable mutants produced epidermin again after several transfers. All stable epi mutants still contained plasmid pTü32 which suffered no deletions or rearrangements as tested by restriction endonuclease analysis. The 10 epi mutants were used for complementation studies.

Various restriction fragments of plasmid pTü32 were cloned in *S. carnosus* to test for heterologous epidermin production. The fragments were inserted into plasmid vectors T181mcs and pCU1 as described above and the various ORFs which were subcloned as shown in FIG. 16B.

Cloning was first carried out in *S. carnosus* (by protoplast transformation (Gotz et al., *FEMS Microbiol Lett.* 40:285–288 (1987)) or *E. coli* (using $CaCl_2$; Cohen et al., *Proc. Nat. Acad. Sci. USA* 69:2110–2114 (1972)) and then the recombinant plasmids were isolated and transferred into the various *S. epidermidis* epi mutants by electroporation (Augustin et al., *FEMS Microbiol Lett.* 66:203–208 (1990)). Enzymes used for molecular cloning were obtained from Boehringer Mannheim (Mannheim, F.R.G.), BRL (Eggenstein, F.R.G.) or Pharmacia (Sweden). This indirect transformation method was necessary since transformation of *S. epidermin* strains was only successful with circular A series of plasmids were constructed which carry various epi genes (A, B, C, D, P and Q) (FIG. 16B). Two plasmids pTepi14 and pTepiABCDQ were able to complement all epi mutants. The other constructed plasmids pCUepiABC, pTepiAB, pCUepiCDQ, pCUepiB, pCUepiA$_1$ pCUepiA$_2$, pCUepiDQ and pCUepiQ contained the indicated genes.

The various plasmids were able to complement only certain classes of mutants which are classified herein as follows:

EMS 5 and 6 —epiA mutants,
EMS 18, 33 and 45 —epiB mutants,
EMS 12, 13, 19 and 39 —epiC mutants,
EMS 11 —epiD mutant.

The results as shown below indicate at least that the four ORFs epiA, B, C and D are required for epidermin biosynthesis.

The plasmid pCUepiA$_1$ carries the structural gene epiA as the only complete ORF and an additional 1400 bp upstream and 602 bp downstream, the latter encoding 190 amino acids of the epiB N-terminus. Transformation using pCUepiA$_1$ resulted in the complementation of the epidermin mutants EMS 5 and 6 identifying them as epiA mutants. The smaller epiA-containing ScaI fragment cloned in both orientations in pCUepiA$_2$ failed to complement the epi mutants as the epiA promoter was cut by this enzyme.

pCUepiB carries a BstN1 fragment containing the complete epiB and an upstream region of 100 bp which includes 75 bp of the 3' terminus of epiA; the EpiA promoter is missing. Transformation with pCUepiB failed to complement any *S. epidermidis* mutant to epidermin production, indicating that epiB lacks its own promoter and is very likely co-transcribed from the epiA promoter.

This is in agreement with the results obtained with pTepiAB (FIG. 16B; Table 1) which contains epiA promoter and the complete epiA and B genes and the use of which complements both the epiA and epiB mutants.

Plasmid pCUepiCDQ was able to complement both epic and epiD mutants and plasmid pCUepiDQ was only able to complement the epiD mutant (Table 1). The complementation was independent of the orientation of the cloned DNA fragment These results show that both epiC and epiD possess their own promoters.

Example 6

The epiA mutated pTü32 derivatives were isolated from EMS 5 and 6 and the respective epiA ORFs were sequenced. Both plasmids had point mutations within epiA; in the EMS 5 plasmid the codon AGT (Ser$^3$) was changed to AAT (Asn$^3$) and in the EMS 6 plasmid the codon GGA (Gly$^{10}$) was changed to GAA (Gln$^{10}$); both these mutations were located at crucial sites within the unmodified epidermin.

Example 7

An epiB (on a BstN1-fragment) was put under the control of the promoter on plasmid pPS4 (FIG. 17). The resulting plasmid pPS4epiB was able to complement the epiB mutants EMS 18, 33 and 45. A plasmid containing epiB in the opposite orientation did not complement the mutations. This also establishes that pCUepiB was unable to complement any of the EMS mutants, because the epiA promoter is missing.

Example 8

As described above, the presence of pTepi14 (FIG. 16A) resulted in epidermin biosynthesis in S. carnosus; however, the presence of pTepiABCDq did not. The minimum size of DNA required which leads to heterologous epidermin expression in S. carnosus was determined by complementing S. carnosus (pTepiABCDQ) with distally located DNA fragments (FIG. 18). Transformation of S. carnosus (pTepiABCDQ) with plasmids pCA44-90, pCA44-91 and pCA44-92 led to epidermin production, pCA44-92 containing the complete epiQ and epiP ORFs consisted of the smallest DNA fragment able to complement epidermin production. These results indicate that the epidermin biosynthetic genes are clustered within an 8kb DNA fragment containing the six ORFs; epiA, B, C, D, Q and P and that no other genes are involved in epidermin biosynthesis.

In these examples staphyloccal plasmid DNA was prepared by the cleaved lysate method (Makino et al., J. Mol. Biol. 190:37–44 (1986)). Cells were lysed by the addition of lysostaphin (8 μg/ml) and the DNA was isolated by CsCl-centrifugation. E. coli supercoiled plasmid DNA was prepared by the modified alkaline lysis method (Birnboim et al., Nucl. Acid Res. 7:1513–1518 (1979)).

The DNA sequence of the PCR-amplified epiA-containing fragment and the two mutated epiA regions of the S. epidermidis mutants, EMS 5 and 6, was determined by double-stranded DNA sequencing using the dideoxy procedure (McMaster et al., Proc. Natl. Acad. Sci. USA 74:4835–4839 (1977)), the "sequence" list of Pharmacia and (α-$^{35}$S)-dATP from Amersham. Primers used for DNA sequencing and PCR amplification were synthesized using the DNA-synthesizer of Applied Biosystems. The sequences of the two primers for PCR amplification of epiA are as follows:

a)  5'-GGGTTTTAGG(TA)ATCCTTTTTAATAAATTTTTAGGAS-3' (SEQ ID NO:6)

b)  5'-CCTCAAAATTAAGACG(A)GAT(G)CCTCTATTGAAGCCC-3' (SEQ ID NO:7)

Primer a) binds in front of the RBS of epiA and primer b) after the epiA stop codon. These bases indicated by bold letters represent (shown in brackets) used to create BamHI sites in front and at the end of epiA; the epiA promoter is absent in the amplified DNA fragment.

For determination of the DNA sequence of the mutated epiA in the mutants EMS 5 and 6, plasmid pTü32 was isolated and the DNA region was amplified by PCR using another set of DNA primers binding upstream of the postulated epiA promoter region (5'-GGTTTGGTTATTTTCC-3')9SEQ ID NO:8) and downstream of the stop codon (5'-CCTCAAAATTAAGACAGAGCCTC-3')(SEQ ID NO:9); the DNA sequence of epiA is also shown in Schnell et al., Nature (Lond.) 333:276–278 (1988).

Example 9

The epi D gene was isolated from the plasmid pTepi14, multiplied by PCR amplification and cloned into the StuI-restriction site of vector pIH902 (New England, Biolabs) by "blunt end" ligation, with the result that the epi D gene is fused without any intervening base pairs immediately at the Factor Xa-cleavage site of vector pIH902, which was then transformed into E. coli.

Cultivation of the E. coli resulted in expression of the enzyme Epi D fused to the Maltose binding protein of E. coli. The resulting fusion protein was purified by affinity chromatography on Amylose column material.

It was found that the enzyme epiD could be cleaved from the fusion protein in low yield by means of Factor Xa. A modification of the amino acid sequence at the cleavage region will enable the cleavage rate to be improved.

The fusion protein was sequenced at the DNA level from the fusion position to the 3' end of epiD. The epiD sequence corresponded to the wild type sequence of S. epidermidis.

From the foregoing description, one skilled in the art can easily ascertain the essential characteristics of this invention, and without departing from the spirit and scope thereof can make various changes and modifications of the invention to adapt it to various usages and conditions.

What is claimed is:

1. A plasmid capable of transforming a bacterial host, the plasmid comprising (a) a nucleotide molecule coding for the prepeptide sequence −30 to −1 of pre-epidermin; and operably linked, in the 5' to 3' direction, to (b) a DNA molecule coding for gallidermin.

2. A recombinant DNA molecule encoding a protein Epi B, having the amino acid sequence set forth in SEQ ID NO:20.

3. A recombinant DNA molecule encoding a protein Epi C, having the amino acid sequence set forth in SEQ ID NO:21.

4. A recombinant DNA molecule encoding a protein Epi D, having the amino acid sequence set forth in SEQ ID NO:22.

5. A recombinant DNA molecule encoding a protein Epi P, having the amino acid sequence set forth in SEQ ID NO:24.

6. A recombinant DNA molecule encoding a protein Epi Q, having the amino acid sequence set forth in SEQ ID NO:23.

7. A plasmid comprising a DNA molecule according to claim 2 wherein said DNA molecule is operably linked to a promoter.

8. A plasmid comprising a DNA molecule according to claim 3 wherein said DNA molecule is operably linked to a promoter.

9. A plasmid comprising a DNA molecule according to claim 4 wherein said DNA molecule is operably linked to a promoter.

10. A plasmid comprising a DNA molecule according to claim 5 wherein said DNA molecule is operably linked to a promoter.

11. A plasmid comprising a DNA molecule according to claim 6 wherein said DNA molecule is operably linked to a promoter.

12. A method of preparing a protein selected from the group consisting of Epi B, Epi C, Epi D, Epi P and Epi Q, which comprises inserting at least one DNA molecule according to any one of claims 2 to 6 into a plasmid vector such that the DNA molecule is under the control of a regulatory promoter;

inserting the resulting plasmid vector into a suitable host;

culturing said host so that the protein coded by said at least one DNA molecule is expressed; and isolating the expressed protein.

13. A plasmid comprising a DNA molecule encoding Epi P wherein said DNA molecule is operably linked to a promoter.

14. A plasmid comprising a DNA molecule encoding Epi Q wherein said DNA molecule is operably linked to a promoter.

* * * * *

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
        ( A ) LENGTH: 15 base pairs
        ( B ) TYPE: nucleic acid ( C ) STRANDEDNESS: single
            ( D ) TOPOLOGY: linear ( x i ) SEQUENCE DESCRIPTION: SEQ ID NO:1:

CACATCCAGG AGTAC                                                                                15

( 2 ) INFORMATION FOR SEQ ID NO:2:

( i ) SEQUENCE CHARACTERISTICS:
            ( A ) LENGTH: 14 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2:

GTRCADATRA AYTT                                                                                 14

( 2 ) INFORMATION FOR SEQ ID NO:3:

( i ) SEQUENCE CHARACTERISTICS:
            ( A ) LENGTH: 5 amino acids
            ( B ) TYPE: amino acid
            ( D ) TOPOLOGY: linear ( x i ) SEQUENCE DESCRIPTION: SEQ ID NO:3:

Lys  Phe  Ile  Cys  Thr
    1                   5

( 2 ) INFORMATION FOR SEQ ID NO:4:

( i ) SEQUENCE CHARACTERISTICS:
            ( A ) LENGTH: 4 amino acids
            ( B ) TYPE: amino acid
            ( D ) TOPOLOGY: linear ( x i ) SEQUENCE DESCRIPTION: SEQ ID NO:4:

Pro  Xaa  Gly  Pro
    1

( 2 ) INFORMATION FOR SEQ ID NO:5:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:5:

CACATCCAGG AGTAC                                                                                15

( 2 ) INFORMATION FOR SEQ ID NO:6:

( i ) SEQUENCE CHARACTERISTICS:
            ( A ) LENGTH: 35 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:6:

GGGTTTTAGD ATCCTTTTTA ATAAATTTTT AGGAG                                                           35

( 2 ) INFORMATION FOR SEQ ID NO:7:

( i ) SEQUENCE CHARACTERISTICS:
            ( A ) LENGTH: 34 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:7:

CCTCAAAATT AAGACRGAKC CTCTATTGAA GCCC  34

( 2 ) INFORMATION FOR SEQ ID NO:8:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GGTTTGGTTA TTTTCC  16

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

CCTCAAAATT AAGACAGAGC CTC  23

( 2 ) INFORMATION FOR SEQ ID NO:10:

( i ) SEQUENCE CHARACTERISTICS:
        ( A ) LENGTH: 423 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 162..320

( x i ) SEQUENCE DESCRIPTION: SEQ ID NO:10:

```
TTTAAACTTT ATATCATTAA TATAATGTTT AGGAAAAGTA GAAGAAAATT ACACTTTTGT        60

AATTTTCTGA ATATACATAG TATTTATTTT GGGGGAGTAC TAAAATAATA ATTGAAAAGG       120

GTTTTATAAT CCTTTTTAAT AAATTTTTAG GAGTGTTTAA A ATG GAA GCA GTA          173
                                             Met Glu Ala Val
                                              1

AAA GAA AAA AAT GAT CTT TTT AAT CTT GAT GTT AAA GTT AAT GCA AAA        221
Lys Glu Lys Asn Asp Leu Phe Asn Leu Asp Val Lys Val Asn Ala Lys
 5              10                  15                  20

GAA TCT AAC GAT TCA GGA GCT GAA CCA AGA ATT GCT AGT AAA TTT ATA        269
Glu Ser Asn Asp Ser Gly Ala Glu Pro Arg Ile Ala Ser Lys Phe Ile
                 25                  30                  35

TGT ACT CCT GGA TGT GCA AAA ACA GGT AGT TTT AAC AGT TAT TGT TGT        317
Cys Thr Pro Gly Cys Ala Lys Thr Gly Ser Phe Asn Ser Tyr Cys Cys
         40                  45                  50

TAATTCAGAA GAATTAGATT GGCAGGGCTT CAATAGAGGC TCTGTCTTAA TTTTGAGGTG      377

AAATAGAATT GGATAATATA TTTGTTCCAT CGAATATATA TATGGT                    423
```

( 2 ) INFORMATION FOR SEQ ID NO:11:

( i ) SEQUENCE CHARACTERISTICS:
        ( A ) LENGTH: 52 amino acids
        ( B ) TYPE: amino acid
        ( D ) TOPOLOGY: linear ( i i ) MOLECULE TYPE: protein (x i) SEQUENCE DESCRIPTION: SEQ ID NO:11:

| Met | Glu | Ala | Val | Lys | Glu | Lys | Asn | Asp | Leu | Phe | Asn | Leu | Asp | Val | Lys |
| 1 | | | | 5 | | | | | 10 | | | | | 15 | |

| Val | Asn | Ala | Lys | Glu | Ser | Asn | Asp | Ser | Gly | Ala | Glu | Pro | Arg | Ile | Ala |
| | | | 20 | | | | | 25 | | | | | 30 | | |

| Ser | Lys | Phe | Ile | Cys | Thr | Pro | Gly | Cys | Ala | Lys | Thr | Gly | Ser | Phe | Asn |
| | | 35 | | | | | 40 | | | | | 45 | | | |

| Ser | Tyr | Cys | Cys |
| | 50 | | |

(2) INFORMATION FOR SEQ ID NO:12:

(i) SEQUENCE CHARACTERISTICS:
        (A) LENGTH: 52 amino acids
        (B) TYPE: amino acid
        (D) TOPOLOGY: linear (i i) MOLECULE TYPE: protein (x i) SEQUENCE DESCRIPTION: SEQ ID NO:12:

| Asn | Glu | Ala | Val | Lys | Glu | Lys | Asn | Asp | Leu | Phe | Asn | Leu | Asp | Val | Lys |
| 1 | | | | 5 | | | | | 10 | | | | | 15 | |

| Val | Asn | Ala | Lys | Glu | Ser | Asn | Asp | Ser | Gly | Ala | Glu | Pro | Arg | Ile | Ala |
| | | | 20 | | | | | 25 | | | | | 30 | | |

| Ser | Lys | Phe | Ile | Cys | Thr | Pro | Gly | Cys | Ala | Lys | Thr | Gly | Ser | Phe | Asn |
| | | 35 | | | | | 40 | | | | | 45 | | | |

| Ser | Tyr | Cys | Cys |
| | 50 | | |

(2) INFORMATION FOR SEQ ID NO:13:

(i) SEQUENCE CHARACTERISTICS:
        (A) LENGTH: 51 amino acids
        (B) TYPE: amino acid
        (D) TOPOLOGY: linear (i x) FEATURE:
        (A) NAME/KEY: Peptide
        (B) LOCATION: 38
        (D) OTHER INFORMATION: /label=Peptide
            / note= "The amino acid labelled "Xaa"at position 38
            is connected to alanine at position 41 via a
            sulfide bridge. This connection creates the amino
            acid (2S,3S,6R)-3-methyl-lanthionine. See figure 5."

(i x) FEATURE:
        (A) NAME/KEY: Peptide
        (B) LOCATION: 44
        (D) OTHER INFORMATION: /label=Peptide
            / note= "The amino acid labelled "Xaa"at position 44
            is dehydrobutyrine."

(i x) FEATURE:
        (A) NAME/KEY: Peptide
        (B) LOCATION: 33
        (D) OTHER INFORMATION: /label=Peptide
            / note= "Two sulfide bridges, one connecting amino
            acids at positions 33 and 37 and another
            connecting positions 46 and 51 create the amino
            acid meso- lanthionine."

(i x) FEATURE:
        (A) NAME/KEY: Peptide
        (B) LOCATION: 49
        (D) OTHER INFORMATION: /label=Peptide
            / note= "The amino acids at positions 49 and 51
            are connected by a S(CH)2NH bridge."

(x i) SEQUENCE DESCRIPTION: SEQ ID NO:13:

```
Asn Glu Ala Val Lys Glu Lys Asn Asp Leu Phe Asn Leu Asp Val Lys
1               5                   10                  15

Val Asn Ala Lys Glu Ser Asn Asp Ser Gly Ala Glu Pro Arg Ile Ala
            20              25                  30

Ala Lys Phe Ile Ala Xaa Pro Gly Ala Ala Lys Xaa Gly Ala Phe Asn
        35              40                  45

Ala Tyr Ala
        50
```

(2) INFORMATION FOR SEQ ID NO:14:

(i) SEQUENCE CHARACTERISTICS:
        (A) LENGTH: 21 amino acids
        (B) TYPE: amino acid
        (D) TOPOLOGY: linear (ix) FEATURE:
        (A) NAME/KEY: Peptide
        (B) LOCATION: 8
        (D) OTHER INFORMATION: /label=Peptide
            / note= "The amino acid labelled "Xaa"at position 8
            is connected to alanine at position 11 via a
            sulfide bridge. This connection creates the amino
            acid (2S,3S,6R)-3-methyl-lanthionine. See figure 5."

(ix) FEATURE:
        (A) NAME/KEY: Peptide
        (B) LOCATION: 14
        (D) OTHER INFORMATION: /label=Peptide
            / note= "The amino acid labelled "Xaa"at position 14
            is dehydrobutyrine."

(ix) FEATURE:
        (A) NAME/KEY: Peptide
        (B) LOCATION: 3
        (D) OTHER INFORMATION: /label=Peptide
            / note= "Two sulfide bridges, one connecting amino
            acids at positions 3 and 7 and another
            connecting positions 16 and 21 create the amino
            acid meso- lanthionine."

(ix) FEATURE:
        (A) NAME/KEY: Peptide
        (B) LOCATION: 19
        (D) OTHER INFORMATION: /label=Peptide
            / note= "The amino acids at positions 19 and 21
            are connected by a S(CH)2NH bridge."

(xi) SEQUENCE DESCRIPTION: SEQ ID NO:14:

```
Ile Ala Ala Lys Phe Ile Ala Xaa Pro Gly Ala Ala Lys Xaa Gly Ala
1               5                   10                  15

Phe Asn Ala Tyr Ala
            20
```

(2) INFORMATION FOR SEQ ID NO:15:

(i) SEQUENCE CHARACTERISTICS:
        (A) LENGTH: 34 amino acids
        (B) TYPE: amino acid
        (D) TOPOLOGY: linear (ix) FEATURE:
        (A) NAME/KEY: Peptide
        (B) LOCATION: 2
        (D) OTHER INFORMATION: /label=Peptide
            / note= "The amino acid labelled "Xaa"at position 2 is
            dehydrobutyrine."

(ix) FEATURE:
        (A) NAME/KEY: Peptide
        (B) LOCATION: 3
        (D) OTHER INFORMATION: /label=Peptide
            / note= "The amino acids at positions 3 and 7 are connected via a sulfide bridge."

(ix) FEATURE:
(A) NAME/KEY: Peptide
(B) LOCATION: 5
(D) OTHER INFORMATION: /label=Peptide
/ note= "The amino acid labelled "Xaa" at position 5 is dehydroalanine."

(ix) FEATURE:
(A) NAME/KEY: Peptide
(B) LOCATION: 8
(D) OTHER INFORMATION: /label=Peptide
/ note= "The amino acid labelled "Xaa" at position 8 is connected to alanine at position 11 via a sulfide bridge. This connection creates the amino acid (2S,3S,6R)-3-methyl-lanthionine. See figure 5."

(ix) FEATURE:
(A) NAME/KEY: Peptide
(B) LOCATION: 13
(D) OTHER INFORMATION: /label=Peptide
/ note= "The amino acid labelled "Xaa" at position 13 is connected to alanine at position 19 via a sulfide bridge. This connection creates the amino acid (2S,3S,6R)-3-methyl-lanthionine. See figure 5."

(ix) FEATURE:
(A) NAME/KEY: Peptide
(B) LOCATION: 23
(D) OTHER INFORMATION: /label=Peptide
/ note= "The amino acid labelled "Xaa" at position 23 is connected to alanine at position 26 via a sulfide bridge. This connection creates the amino acid (2S,3S,6R)-3-methyl-lanthionine. See figure 5."

(ix) FEATURE:
(A) NAME/KEY: Peptide
(B) LOCATION: 25
(D) OTHER INFORMATION: /label=Peptide
/ note= "The amino acid labelled "Xaa" at position 25 is connected to alanine at position 28 via a sulfide bridge. This connection creates the amino acid (2S,3S,6R)-3-methyl-lanthionine. See figure 5."

(ix) FEATURE:
(A) NAME/KEY: Peptide
(B) LOCATION: 33
(D) OTHER INFORMATION: /label=Peptide
/ note= "The amino acid labelled "Xaa" at position 33 is dehydroalanine."

(xi) SEQUENCE DESCRIPTION: SEQ ID NO:15:

Ile Xaa Ala Ile Xaa Leu Ala Xaa Pro Gly Ala Lys Xaa Gly Ala Leu
1               5                   10                  15

Met Gly Ala Asn Met Lys Xaa Ala Xaa Ala His Ala Ser Ile His Val
            20                  25                  30

Xaa Lys (2) INFORMATION FOR SEQ ID NO:16:

(i) SEQUENCE CHARACTERISTICS:
(A) LENGTH: 8700 base pairs
(B) TYPE: nucleic acid
(C) STRANDEDNESS: single
(D) TOPOLOGY: linear (xi) SEQUENCE DESCRIPTION: SEQ ID NO:16:

```
AGATCTTGTG  TTATATAACT  AAACAAATTT  CTCCATTCGT  ATTTAGAAAA  TTGACTTTTA    60

TCAAGTTTAT  CCAAATATAT  ATTTCCAGTA  TATTCTGTAT  TTAACCCAGC  TAATATATTT   120

AATAATGTAC  TTTTTCCACA  CCCACTTTCA  CCTATAATAT  TGTAGATATA  ACCTTTATGA   180

AGATCCAAAC  TTATAGAATT  TATTATTTGT  TTATTGTCTT  TTGTGAAGTT  CAAATCATTT   240
```

```
ATTTCCATTT TTTGAACAAA GTTATTGTAA GTTGTTTTAA TAGTTAATAC CTCTTCTGGT    300

TCTTTATTTA TTTTTAAAAT TCTATCTGAA GATCCAATTG CTCGTTGTAC TTCCGTCCAA    360

TAAGATGTAA TAGATACTAT TGGATTAATA ATTTGAAATA AATATAAAAC ATAAGCAAAC    420

ATATCTCCGC TTTTCATCAT ATTATTTTCC ATTAAGTAAT AACCCAAAAA TAAAATACCA    480

AAAATGTTAA TAAATAGAAT TAAGTTCATA ATTGGTTCGA AAAAAGATAA TACTTTGATC    540

TTATGTAACT CTATATCGAA TATATTTTTT AATAGGGTAT AGTTTTTAT TTTTTCGATA    600

TTATATGTAC TTAAAGTTTT TATTAATTTT ATTGTAGATA ATCTATTACT ATAATAAGAA    660

GATAATTTAG CAGTAGCTTC TTGAGATTTA CTTGATACTC TTTTCATTAT ATTTCCTATA    720

GGTAGTATTA CAATTATCAA TATAGGTAAT GTACACACTA AATATAATGT CAAGGTTTTG    780

TTAATTATAT ATAAAAATAT TAGTGATACT ATAACTGAAA ATAAATTCTA CAGAAAAAC    840

TCTAGTTATG TTCATAGTAT CGTTACTAA CCTACTAGTT AAGTTACTTG CTGAGTTTTT    900

TAAGTGAAAA CTATAAGGTA ACTTATCAC TTATTCCAT GTAACACTTC TAATGTTTTG    960

TATTATTTTT TGACCTATAT ATCCAAGAAT ATAAGTAGAA ACACCAGAAA ATATTAAAGT   1020

CAGACCAAAA CATATAATAA TGATTACAAT TTATCTGTT GATAAGCTAG ATTTGTTTAA   1080

GGCATTTCTA ATTATTAAAG GAATGTATAA TGAAAAACTA GTTCCAATCA AACTAAATAT   1140

TAGTCCAATA CTTAAAAGTA GAGTGTTAGG TTTGGTTATT TTCCATAAAT CATATAGACC   1200

TTTGATAATA TCATCACCTT TTAAACTTTA TATCATTAAT ATAATGTTTA GGAAAAGTAG   1260

AAGAAAATTA CACTTTTGTA ATTTTCTGAA TATACATAGT ATTTATTTTG GGGGAGTACT   1320

AAAATAATAA TTGAAAAGGG TTTTATAATC CTTTTTAATA AATTTTTAGG AGTGTTTAAA   1380

ATGGAAGCAG TAAAAGAAAA AAATGATCTT TTAATCTTG ATGTTAAAGT TAATGCAAAA   1440

GAATCTAACG ATTCAGGAGC TGAACCAAGA ATTGCTAGTA AATTTATATG TACTCCTGGA   1500

TGTGCAAAAA CAGGTAGTTT TAACAGTTAT TGTTGTTAAT TCAGAAGAAT TAGATTGGCA   1560

GGGCTTCAAT AGAGGCTCTG TCTTAATTTT GAGGTGAAAT AGAATTGGAT AATATATTTG   1620

TTCCATCGAA TATATATATG GTAAGAACTC CTATATTTTC AATTGAATTA TATAATCAAT   1680

TCTTAAAATC TGACAATATA GATTATGACT TAATTTTACA AAACGATATT TTTAAAGAAT   1740

CTATAATGAC AACGACATAT AATCTTTATC AAAGTATTGG CAAAATAGAC TGGGAAAAGG   1800

ATAATAAAAA AACCAGAAAT GTAAAAGAAA GTTATTAAAA ATATCTCATA AGAATGAGTA   1860

CTAGAAGTAC ACCATATGGA ATGCTAAGCG GTGTAGCTTT AGGGGAATTT AGTGAAAATA   1920

ATAATATTAA AATTAAGGAC TCTTCGTTTC ATAAAAAGA TGTAAAAATA GATGGGCAAT   1980

GGTTATATAA ATTAGTCCAT TATTTAGAAA GCGATTACAC ATATTATAAA GACAGTTTTG   2040

TCATATGGAA TCAACAAAAT TATATTTATA ACAATCGTTT ATATTTAGAT AATAATTCAT   2100

CAATCACTGA AAATAAAAGA AATGATGTAT TATCTGTCAA ATACAATTCT ATATTAGTGT   2160

TTATACATGA GAATTCTAAA AAAAATATTA CTTATGAAGA ACTTGTACAA TTGATATCTA   2220

GTAAGTACAG TATAGAAAAT AAAGAAGAAG TAAAAGTATT TGTTCAAGAA CTCATAAATA   2280

AAGAAATTAT ATTTCTGAT TTGAGACCTA CATTAGAGAA TAAAAATCCT TTAGATTACA   2340

TTATTAATAG TTTAAATCCA AAAAATAGTT TAGTTGGAAC ACTTATTAAT ATTTCTAATG   2400

AAATTACAAA ATATTCTAAA ATGCCTTTAG GAAAAGGAGA ATATAAATAT TTAGATATTG   2460

TTAATTTAAT GTCACAATTA TTTGTTTCTA AAAACTATTT GCAAATAGAT ACCTATATAG   2520

ATTATTCAAG AAATGAATTA AAACAAAGTT TAGCTGATAA TATTAGTGAA GCAGCATATA   2580

TTCTCTGGTT ATTATCTCCT AATCATTTTG GTACAAAAAC TATTAGGAAT TATCACGAAT   2640
```

-continued

| | | | | | |
|---|---|---|---|---|---|
| TTTTTATGGA | TAAATATGGA | TTTGAACAAC | TAGTAAATTT | AAAGCAATTG | CTCTCAGATA 2700 |
| TAAATGGATT | TGGCTATCCC | AAAAAAGACA | GTTATAGTTT | TTCTAATAAC | ATTGCATTTT 2760 |
| TAAAAGAAAA | GTATTTGCTT | GCAATTCAAA | ATAACAGCCA | TATTGAAATA | ACAGAAAACG 2820 |
| ACGTTAAAAA | TTTAGAAAAG | AATAATACAG | TTTCTAAAAT | CAATGCGCCT | GTTTCAACTG 2880 |
| AAATATATAG | TGAGATATAT | TTTGGAAATT | CAATAAAAGG | TTATGAGGAT | TTTGCCGTGA 2940 |
| TAAGTCCAAT | ATTAGGATCT | TTTAATGCCG | GTGCAACTTT | TGGAAGGTTT | ACGGGAAATT 3000 |
| TCAATATAAA | GAAAAAAAT | CAATTACAAA | AAGAAATAGT | GCATCATTAC | AATAATTACA 3060 |
| TGAATGAAAA | TGGTTTAGAA | ATAAGCCAAT | TAAATGAAGG | TCCTCTTAAC | TCAAGAAATG 3120 |
| TAAATATTTT | GAATAATAAT | AGAATATATA | ATACTTGTTT | AAATTTAAAT | TTACCTAAAA 3180 |
| GTGATATAGA | TATAAATGAC | ATATTTATTG | GAGCTACATT | TAACAAACTT | TATCTATATT 3240 |
| CTGAAAAACA | TGATTCAAGA | ATTGTATTCG | TATCTAATTC | AATGTTAAT | TATGAGTTTG 3300 |
| GATCTGAATT | ATACAAATTT | TTAAGAGAAA | TTTCATTTGA | AAAACAAAA | TTTATACAAC 3360 |
| CTATAACTGA | AGAAGGCATT | GACTCATTAC | CTTTTGTCC | AAGAATTATT | TATAAAAATA 3420 |
| TTATTTTAAA | ACCAGCTACT | TGGAAAATAA | ATTCAGAAAT | GTTTCTGAA | ACTGAAAATT 3480 |
| GGTTAAATAG | GTTCGCAACT | ATTAGAGAAA | AATGGCATAT | TCCAAAAGAT | GTAATTATTG 3540 |
| CTTTTGGAGA | TAATCGATTG | CTATTAAATT | TATTAAATGA | CAAGCATCTC | ATTATACTAA 3600 |
| AAAAAGAACT | AAAAAAACAT | GGTAGGATTC | GAATATTAGA | AAGCTTATC | AATGAATCTA 3660 |
| ATAATGAGAG | AATGTTAGAA | ATTGTTACGC | CATTATATAA | AAAAACTAGT | TTAAAAGAAC 3720 |
| AATCTTTCAT | TATACCTAAA | AATAGAAATA | AGCACTTCAA | TAATCTTAAA | GATTGGTTTT 3780 |
| CAATTCATTT | AAGTATTCCT | AAAACATACC | AAGATAATTT | TATTCAAGAT | TATCTATTAC 3840 |
| CATTTATAAC | GGAATTAAAA | GTTAATAATT | TTATTAATAA | ATTTTTTTAC | ATAAAATTTA 3900 |
| AAGAAGATGA | AGATTTTATA | AAATTAAGAT | TATTAAGAGA | AGATGAAGAT | TATTCTCAAA 3960 |
| TTTATTCTTT | CATAAAAAAT | TGGAAAGATT | ATTGCTTATT | AAATAGTGAA | TTATATGACT 4020 |
| ATTCTATAGT | TGATTATGTT | CCTGAAGTAT | ATAGATATGG | TGGTCCACAC | GTAATTGAAG 4080 |
| ATATTGAGAA | TTTTTTTATG | TATGATAGTC | TATTATCAAT | AAATATAATA | CAATCAGAGT 4140 |
| TCAAAATTCC | AAAAGAATTT | ATCGTTGCTA | TATCAATAGA | TTTTTTATTA | GATTATTTAG 4200 |
| AAATTAATAA | AAGTGAGAAA | GAAGAAATTT | TAATTAATAA | TGCGGAAGAT | TTATATCGTA 4260 |
| GTAATGACAT | AAGAGAATAT | AAAAATTTAT | TAGCTAAACT | TACCAATCCT | AAAAATGACT 4320 |
| ATGAAATTTT | AAAAAAAGAA | TTTCCGAATC | TTCATGAATT | TCTATTTAAT | AAAATTAGTA 4380 |
| TTTTAGAAAA | TCTTAAAAAG | ACACTACAAA | AAAGCTTATA | TACTTCACGT | TCTAGGATAA 4440 |
| TTGGCAGTTT | TATAAACATG | CGTTGTAATA | GAATATTCGG | TATTAATCCT | GAAAAGAAA 4500 |
| AATTTGTTTT | ATCTATTTTT | AATGAAATTA | CAAAAACTAA | AAAATATTGG | GATGGTTGTG 4560 |
| ATTAATATTA | ATAACATTAA | AAAAATTTTA | GAAATAAAA | TCACCTTTTT | GTCTGACATT 4620 |
| GAAAAGCTA | CATATATTAT | AGAAAATCAA | AGTGAGTATT | GGGATCCTTA | TACTCTATCT 4680 |
| CATGGTTATC | CAGGTATAAT | ACTTTTTTTA | AGCGCATCAG | AAAAGTATT | TCATAAAGAT 4740 |
| TTAGAAAAAG | TAATACATCA | ATATATTAGA | AAACTAGGCC | CTTATTTAGA | AAGTGGTATT 4800 |
| GATGGATTTT | CACTTTTTAG | TGGTCTTTCC | GGAATTGGAT | TTGCGCTAGA | CATTGCGTCT 4860 |
| GATAAACAGT | ACTCTTATCA | AAGTATCTTA | GAACAAATTG | ATAATTTACT | TGTTCAATAT 4920 |
| GTTTTTGATT | TTTTAAATAA | CGATGCATTG | GAAGTAACCC | CTACTAACTA | TGATATAATA 4980 |
| CAAGGATTTT | CTGGTATAGG | AAGGTACTTG | TTAAATAGAA | TATCGTATAA | TTATAATGCA 5040 |

```
AAAAAAGCAT  TAAAGCATAT  ACTTAATTAC  TTCAAAACAA  TTCATTACTC  TAAAGACAAT    5100

TGGTTAGTTT  CAAATGAACA  TCAATTTTTA  GATATAGATA  AGCAAAATTT  TCCGTCAGGA    5160

AATATAAATT  TAGGATTAGC  GCATGGTATT  TTAGGTCCTC  TATCATTAAC  AGCTTTGAGT    5220

AAAATGAATG  GGATTGAAAT  CGAAGGCCAT  GAAGAGTTTT  TACAAGACTT  CACTTCATTT    5280

TTGCTCAAAC  CTGAATTCAA  AAATAATAAT  GAATGGTTCG  ATCGCTATGA  TATATTAGAA    5340

AATTATATAC  CTAATTATTC  CGTCAGAAAC  GGTTGGTGTT  ACGGTGATAC  AGGGATTATG    5400

AATACATTAC  TTTTGTCTGG  TAAAGCCTTA  AATAATGAAG  GCTTAATTAA  AATGTCTAAA    5460

AATATTTTAA  TTAACATAAT  AGATAAGAAT  AATGATGATT  TAATCAGTCC  AACCTTCTGT    5520

CACGGACTAG  CATCGCACTT  AACCATTATT  CATCAAGCGA  ATAAATTCTT  TAATCTATCT    5580

CAAGTAAGCA  CATATATCGA  TACCATTGTC  AGAAAAATTA  TTAGTCATTA  TTCTGAAGAA    5640

AGTAGTTTTA  TGTTCCAAGA  CATAGAGTAC  TCATACGGAC  AAAAAATTTA  TAAAAACAAA    5700

GTGGGAATTC  TAGAGGGTGA  ATTAGGTGTT  CTTTTAGCTT  TACTAGATTA  TATTGATACA    5760

CAAAACCAAT  CAAGGAAAAA  TTGGAAAAAT  ATGTTTTTAA  TAACATAATA  GGAGGAATAA    5820

GATATGTATG  GAAAATTATT  GATATGCGCT  ACAGCATCGA  TAAATGTAAT  TAATATTAAT    5880

CACTACATAG  TTGAGTTAAA  GCAACATTTT  GATGAAGTTA  ATATATTATT  TAGTCCTAGT    5940

AGTAAAAATT  TTATAAATAC  TGATGTTCTC  AAGTTATTTT  GTGATAACTT  GTACGATGAA    6000

ATTAAGATC  CTCTTTTAAA  TCATATCAAT  ATTGTAGAAA  ATCATGAATA  TATTTTAGTA    6060

TTACCTGCAT  CAGCAAATAC  TATTAATAAA  ATAGCTAATG  GTATATGTGA  TAATCTTTTA    6120

ACTACTGTAT  GTTTAACCGG  ATATCAAAAA  TTATTTATAT  TTCCAAATAT  GAACATAAGA    6180

ATGTGGGGAA  ATCCATTTTT  ACAAAAAAAT  ATTGATTTAC  TTAAAAATAA  TGATGTGAAA    6240

GTGTATTCCC  CTGATATGAA  TAAATCATTC  GAAATATCTA  GTGGCCGTTA  CAAAAACAAT    6300

ATCACAATGC  CTAATATTGA  AAATGTACTA  AATTTTGTAT  TAAATAACGA  AAAAAGACCT    6360

TTGGATTAAC  AAAGGTCTTT  TCTAATTAAA  ATTTTATATC  CGAGTTTACG  TTCATTAATA    6420

ATTTCTATCT  CTTTACAATT  TTTTAAACTA  TCCCTTAATC  GATGGATATA  TACATTTATT    6480

GTATTAGAAT  CAACAAAGTC  TTCTGTATCC  CACACTCCCT  TTTTTAATTC  CTCTTTTGAT    6540

ACATATCTTC  CAAGATTAAT  ATATAAGCAC  CGTAGAATTT  TAATTCTAT  ATTAGAAAGA    6600

TTAACTAAGT  AATTATTAAA  CACAAATTGA  TGGTTTTCAA  AGTCTATAAA  ATCATCATTA    6660

ACATATTTAA  TATACTTTTT  TATTTCATTT  AAAATTCTAC  ATAATATTAA  ACTTTTGCTT    6720

TCATTATTTT  TTATAATATA  TAAATCTATG  CCTAAACTAT  AAAAATAACA  CTTCCTACTA    6780

TAGCTAGTAT  TACCTGTTAT  TATAACTATT  GGAATTTTTC  CTATAAATTC  TTTTAAAAAC    6840

GTATAATACT  CATCAAACTT  TTCATACACA  ATTATAAAAT  TTGGGTCTAT  ATTTGAAGAA    6900

TTAATTGTAA  TTCTTCTATC  TAATTCTAAA  ATACTTTCAA  TAAGAATAGA  ATCTACCTCA    6960

CCGACAATAT  TAATAGAAAT  CATTTTATTC  CCTTCATTCT  TTAAGTAATT  TGTATACGTC    7020

TAGTTTTCCA  TTACCATAAT  GTTTTTTATC  CATATATTTT  TCTTTTTCTA  TCCCTTTTTT    7080

CTTAAATAAC  TCTATAGCTG  TTTCGGGTTG  GTCTTTTAAT  TGATACTTAT  CAATTTCTAG    7140

TGCTAAAGCT  CCAGAAACCT  TGGGTGCAGC  AAGTGATGTC  CCTGATTGAT  ATATGTATCT    7200

TCCATTAGAA  GAAGTACTTA  AAACACTTTG  TTTTTGCATA  TATCCTTTTT  CTAACCAAGC    7260

ATCTTTTCCA  TACTTATCTA  AAAGTTTATA  AGAACCTCCT  ATCGTCATTA  AATCTATAAA    7320

ATTATTTCCA  TAATTAGAAA  ACTCAGAAAT  ATAATCATTA  TCATCGATGG  ATCCTACAGT    7380

CATAACATTA  TTTAGATTTG  CTGGGCTATC  ATATACCTTT  TTTGATGTTT  TAGAATTTAG    7440
```

| | | | | | | |
|---|---|---|---|---|---|---|
| ATTTCTTTTT | TTATTTATTT | CTTTTACTTT | TTTTACATTG | ATACCGTCAT | TACCCACAGC | 7500 |
| TGCAACAACA | ATACTACCTT | TTTTTGAGC | ATAGTTTATA | GCTTTCTGTA | GTGCATCGTA | 7560 |
| ATCAACTTTT | TCATCATCTC | TTAATTTTTT | TTTATTTTGA | TTATCTTTAA | TTAAATAATT | 7620 |
| TCCTAAACTA | ACGTTGATTA | CATCATTGTC | ATCATTTGCT | GCATCAATAA | TTCCTTTAGA | 7680 |
| TACCCAAAGC | ATTTCACTTT | TCTTTGAGCC | AAATACTCGG | TATACATTCA | TCTCTACTCC | 7740 |
| AGGGTTTACA | CCTTTTAAAT | TACCGTTTGC | TCCTATTTGT | CCTGCTACTA | ATGTACCATG | 7800 |
| ATTCAATTTA | TCTTCTTCAA | AATTTTTATT | TCCTGATTCA | TCGTTTCGC | TACCTCTAAA | 7860 |
| ACCATTTTTA | GGCACTTCAT | TAACTATCTT | ATTTATACTC | TTTAAATCTG | TATGACTACT | 7920 |
| ATTCACACCA | GAATCTACTA | AAGCAACTTT | TGCTTTTTTT | CTATCTGGAC | TTAGCTTATA | 7980 |
| ACTTTTACCT | TCATTTGTTA | TTTTTCGCAT | ATCCCATTGT | CTGTCAAATA | AATCATGGCT | 8040 |
| GCCATTTTTT | TTATTATTA | AATTTTTTCC | TGTCTTTACA | GATTTTTCAA | CTACACAAGT | 8100 |
| GGAACAGGTA | GGATTTACAA | ACTTGACGTT | TTTATTACTC | TTTATTAGTG | AATTTAATTT | 8160 |
| TGATTTGCTA | GTTTAATTT | GTGCTGTATG | TAGTTCAGGA | ATTTTATAAG | TTAACTCGAT | 8220 |
| ATTTTTTTGT | TTAATGGATT | CTTTAAAAGT | TTTTGCATTA | TCATATTCAA | CACTATAATA | 8280 |
| ACTTAATTCT | TCATTTAGTG | AACTTCCAAA | AGCATACTCA | TTTTGCAAAA | AAACTAATGA | 8340 |
| CAATATTAAA | AAAACAATGA | AAAATTTAAA | TTTGTTCATA | TAGCACCTCT | AACATATTAT | 8400 |
| TTATATTAAA | CATTAATTTA | ACACTTATGT | TTTTACTTTT | TTATTTATAT | TATCTTTAAT | 8460 |
| AATGTTCTGT | TGCAAGATGA | AAAATACGAG | GTATCAAAGT | ACCGATACAG | CGAGTATTAC | 8520 |
| ACTCAATTAA | TTAAAAATAA | AATATGTTGT | GATTAAAATT | TATTTTATAA | AAGTATGGGC | 8580 |
| AATTTATTAT | TATTCAAGTT | AAAACAAAGA | GTCCGGGACA | TAAAGTTTCA | GCCTCTTCGT | 8640 |
| CCTAATTACC | AAAAAACTTA | CTCCAAAATC | CTTTTTAGA | TTGGTTTTTT | CTAATTTTTT | 8700 |

( 2 ) INFORMATION FOR SEQ ID NO:17:

( i ) SEQUENCE CHARACTERISTICS:
    ( A ) LENGTH: 275 amino acids
    ( B ) TYPE: amino acid
    ( D ) TOPOLOGY: linear ( x i ) SEQUENCE DESCRIPTION: SEQ ID NO:17:

```
Asp  Gln  Thr  Ile  Tyr  Ser  Phe  Leu  Asn  Arg  Trp  Glu  Tyr  Lys  Ser  Phe
 1                  5                       10                      15

Gln  Ser  Asp  Leu  Lys  Lys  Asp  Leu  Tyr  Ile  Asn  Gly  Thr  Tyr  Glu  Thr
              20                       25                      30

Asn  Leu  Gly  Ala  Leu  Ile  Asn  Leu  Leu  Thr  Ser  Lys  Gly  Cys  Gly  Ser
              35                       40                      45

Glu  Gly  Ile  Ile  Asn  Tyr  Ile  Tyr  Gly  Lys  His  Leu  Asp  Leu  Ser  Ile
        50                       55                      60

Ser  Asn  Ile  Ile  Gln  Lys  Asn  Asp  Lys  Thr  Phe  Asn  Leu  Asp  Asn  Ile
 65                      70                       75                      80

Glu  Met  Lys  Gln  Val  Phe  Asn  Asn  Tyr  Thr  Thr  Lys  Ile  Thr  Leu  Val
                   85                       90                      95

Glu  Glu  Pro  Glu  Lys  Asn  Ile  Lys  Leu  Ile  Arg  Asp  Ser  Ser  Gly  Ile
              100                      105                     110

Ala  Arg  Gln  Val  Glu  Thr  Trp  Tyr  Ser  Thr  Ile  Ser  Val  Ile  Pro  Asn
              115                      120                     125

Ile  Ile  Gln  Glu  Leu  Tyr  Leu  Val  Tyr  Ala  Phe  Met  Asp  Gly  Ser  Lys
              130                      135                     140
```

| Met | Met | Asn | Asn | Glu | Met | Leu | Tyr | Tyr | Gly | Leu | Phe | Leu | Ile | Gly | Phe |
145 | | | | | 150 | | | | | 155 | | | | | 160

| Ile | Asn | Ile | Phe | Leu | Ile | Leu | Asn | Met | Ile | Pro | Glu | Phe | Phe | Ser | Leu |
| | | | | 165 | | | | 170 | | | | | 175 | |

| Val | Lys | Ile | Lys | His | Leu | Glu | Ile | Asp | Phe | Ile | Asn | Lys | Leu | Leu | Thr |
| | | | 180 | | | | | 185 | | | | | 190 | | |

| Tyr | Asn | Lys | Ile | Lys | Glu | Ile | Asn | Tyr | Thr | Ser | Leu | Thr | Lys | Ile | Leu |
| | | 195 | | | | | 200 | | | | | 205 | | | |

| Lys | Ile | Thr | Ser | Leu | Arg | Asn | Ser | Tyr | Tyr | Ser | Ser | Leu | Lys | Ala | Thr |
| | 210 | | | | | 215 | | | | | 220 | | | | |

| Ala | Glu | Gln | Ser | Lys | Ser | Ser | Val | Arg | Lys | Met | Ile | Asn | Gly | Ile | Pro |
225 | | | | | 230 | | | | | 235 | | | | | 240

| Leu | Ile | Val | Ile | Ile | Leu | Ile | Pro | Leu | Thr | Cys | Val | Leu | Tyr | Leu | Thr |
| | | | 245 | | | | | 250 | | | | | 255 | | |

| Leu | Thr | Lys | Asn | Ile | Ile | Tyr | Leu | Phe | Ile | Leu | Ser | Val | Ile | Val | Ser |
| | | | 260 | | | | | 265 | | | | | 270 | | |

| Phe | Leu | Asn |
| | | 275 |

( 2 ) INFORMATION FOR SEQ ID NO:18:

( i ) SEQUENCE CHARACTERISTICS:
( A ) LENGTH: 148 amino acids
( B ) TYPE: amino acid
( D ) TOPOLOGY: linear ( x i ) SEQUENCE DESCRIPTION: SEQ ID NO:18:

| Ser | Leu | Lys | Gly | Asp | Asp | Ile | Ile | Lys | Gly | Leu | Tyr | Asp | Leu | Trp | Lys |
1 | | | | 5 | | | | | 10 | | | | | 15 | |

| Ile | Thr | Lys | Pro | Asn | Thr | Leu | Leu | Leu | Ser | Ile | Gly | Leu | Ile | Phe | Ser |
| | | 20 | | | | | 25 | | | | | 30 | | | |

| Leu | Ile | Gly | Thr | Ser | Phe | Ser | Leu | Tyr | Ile | Pro | Leu | Ile | Ile | Arg | Asn |
| | 35 | | | | | 40 | | | | | 45 | | | | |

| Ala | Leu | Asn | Lys | Ser | Ser | Leu | Ser | Thr | Asp | Lys | Ile | Val | Ile | Ile | Ile |
| 50 | | | | | 55 | | | | | 60 | | | | | |

| Ile | Cys | Phe | Gly | Leu | Thr | Leu | Ile | Phe | Ser | Gly | Val | Ser | Thr | Tyr | Ile |
65 | | | | | 70 | | | | | 75 | | | | | 80

| Leu | Gly | Tyr | Ile | Gly | Gln | Lys | Ile | Ile | Gln | Asn | Ile | Arg | Ser | Val | Thr |
| | | | 85 | | | | | 90 | | | | | 95 | | |

| Trp | Asn | Lys | Val | Ile | Lys | Leu | Pro | Tyr | Ser | Phe | His | Leu | Lys | Asn | Ser |
| | | | 100 | | | | | 105 | | | | | 110 | | |

| Ala | Ser | Asn | Leu | Thr | Ser | Arg | Leu | Val | Asn | Asp | Thr | Met | Asn | Ile | Thr |
| | | 115 | | | | | 120 | | | | | 125 | | | |

| Arg | Val | Phe | Ser | Val | Glu | Phe | Ile | Phe | Ser | Tyr | Ser | Ile | Thr | Asn | Ile |
| | 130 | | | | | 135 | | | | | 140 | | | | |

| Phe | Ile | Tyr | Asn |
145 | | | |

( 2 ) INFORMATION FOR SEQ ID NO:19:

( i ) SEQUENCE CHARACTERISTICS:
( A ) LENGTH: 52 amino acids
( B ) TYPE: amino acid
( D ) TOPOLOGY: linear ( x i ) SEQUENCE DESCRIPTION: SEQ ID NO:19:

| Met | Glu | Ala | Val | Lys | Glu | Lys | Asn | Asp | Leu | Phe | Asn | Leu | Asp | Val | Lys |
1 | | | | 5 | | | | | 10 | | | | | 15 | |

| Val | Asn | Ala | Lys | Glu | Ser | Asn | Asp | Ser | Gly | Ala | Glu | Pro | Arg | Ile | Ala |
|||| 20 |||| 25 ||||| 30 |||

| Ser | Lys | Phe | Ile | Cys | Thr | Pro | Gly | Cys | Ala | Lys | Thr | Gly | Ser | Phe | Asn |
||| 35 ||||| 40 |||| 45 ||||

| Ser | Tyr | Cys | Cys |
||| 50 ||

( 2 ) INFORMATION FOR SEQ ID NO:20:

( i ) SEQUENCE CHARACTERISTICS:
        ( A ) LENGTH: 990 amino acids
        ( B ) TYPE: amino acid
        ( D ) TOPOLOGY: linear ( x i ) SEQUENCE DESCRIPTION: SEQ ID NO:20:

| Gly | Glu | Ile | Glu | Leu | Asp | Asn | Ile | Phe | Val | Pro | Ser | Asn | Ile | Tyr | Met |
| 1 |||| 5 |||| 10 |||| 15 ||

| Val | Arg | Thr | Pro | Ile | Phe | Ser | Ile | Glu | Leu | Tyr | Asn | Gln | Phe | Leu | Lys |
|||| 20 |||| 25 |||| 30 |||

| Ser | Asp | Asn | Ile | Asp | Tyr | Asp | Leu | Ile | Leu | Gln | Asn | Asp | Ile | Phe | Lys |
||| 35 ||||| 40 |||| 45 |||

| Glu | Ser | Ile | Met | Thr | Thr | Thr | Tyr | Asn | Leu | Tyr | Gln | Ser | Ile | Gly | Lys |
|| 50 |||| 55 |||||| 60 |||

| Ile | Asp | Trp | Glu | Lys | Asp | Asn | Lys | Lys | Thr | Arg | Asn | Val | Lys | Glu | Ser |
| 65 |||| 70 |||||| 75 |||| 80 |

| Leu | Leu | Lys | Tyr | Leu | Ile | Arg | Met | Ser | Thr | Arg | Ser | Thr | Pro | Tyr | Gly |
|||| 85 |||||| 90 |||| 95 ||

| Met | Leu | Ser | Gly | Val | Ala | Leu | Gly | Glu | Phe | Ser | Glu | Asn | Asn | Asn | Ile |
|||| 100 |||| 105 |||| 110 |||

| Lys | Ile | Lys | Asp | Ser | Ser | Phe | His | Lys | Lys | Asp | Val | Lys | Ile | Asp | Gly |
||| 115 |||| 120 |||| 125 |||

| Gln | Trp | Leu | Tyr | Lys | Leu | Val | His | Tyr | Leu | Glu | Ser | Asp | Tyr | Thr | Tyr |
||| 130 |||| 135 |||| 140 |||

| Tyr | Lys | Asp | Ser | Phe | Val | Ile | Trp | Asn | Gln | Gln | Asn | Tyr | Ile | Tyr | Asn |
| 145 |||| 150 |||| 155 |||||| 160 |

| Asn | Arg | Leu | Tyr | Leu | Asp | Asn | Asn | Ser | Ser | Ile | Thr | Glu | Asn | Lys | Arg |
|||| 165 |||| 170 |||| 175 ||

| Asn | Asp | Val | Leu | Ser | Val | Lys | Tyr | Asn | Ser | Ile | Leu | Val | Phe | Ile | His |
|||| 180 |||| 185 |||| 190 |||

| Glu | Asn | Ser | Lys | Lys | Asn | Ile | Thr | Tyr | Glu | Glu | Leu | Val | Gln | Leu | Ile |
||| 195 |||| 200 |||| 205 |||

| Ser | Ser | Lys | Tyr | Ser | Ile | Glu | Asn | Lys | Glu | Glu | Val | Lys | Val | Phe | Val |
|| 210 |||| 215 |||| 220 ||||

| Gln | Glu | Leu | Ile | Asn | Lys | Glu | Ile | Ile | Phe | Ser | Asp | Leu | Arg | Pro | Thr |
| 225 |||| 230 |||| 235 |||||| 240 |

| Leu | Glu | Asn | Lys | Asn | Pro | Leu | Asp | Tyr | Ile | Ile | Asn | Ser | Leu | Asn | Pro |
|||| 245 |||| 250 |||| 255 ||

| Lys | Asn | Ser | Leu | Val | Gly | Thr | Leu | Ile | Asn | Ile | Ser | Asn | Glu | Ile | Thr |
|||| 260 |||| 265 |||| 270 |||

| Lys | Tyr | Ser | Lys | Met | Pro | Leu | Gly | Lys | Gly | Glu | Tyr | Lys | Tyr | Leu | Asp |
||| 275 |||| 280 |||| 285 |||

| Ile | Val | Asn | Leu | Met | Ser | Gln | Leu | Phe | Val | Ser | Lys | Asn | Tyr | Leu | Gln |
|| 290 |||| 295 |||| 300 ||||

| Ile | Asp | Thr | Tyr | Ile | Asp | Tyr | Ser | Arg | Asn | Glu | Leu | Lys | Gln | Ser | Leu |
| 305 |||| 310 |||| 315 |||||| 320 |

| Ala | Asp | Asn | Ile | Ser | Glu | Ala | Ala | Tyr | Ile | Leu | Trp | Leu | Leu | Ser | Pro |

-continued

```
                               325                           330                           335
         His  Glu  Phe  Gly  Thr  Lys  Thr  Ile  Arg  Asn  Tyr  His  Glu  Phe  Phe  Met
                        340                           345                           350
         Asp  Lys  Tyr  Gly  Phe  Glu  Gln  Leu  Val  Asn  Leu  Lys  Gln  Leu  Leu  Ser
                        355                           360                           365
         Asp  Ile  Asn  Gly  Phe  Gly  Tyr  Pro  Lys  Lys  Asp  Ser  Tyr  Ser  Phe  Ser
                        370                           375                           380
         Asn  Asn  Ile  Ala  Phe  Leu  Lys  Glu  Lys  Tyr  Leu  Leu  Ala  Ile  Gln  Asn
         385                           390                           395                           400
         Asn  Ser  His  Ile  Glu  Ile  Thr  Glu  Asn  Asp  Val  Lys  Asn  Leu  Glu  Lys
                                  405                           410                           415
         Asn  Asn  Thr  Val  Ser  Lys  Ile  Asn  Ala  Pro  Val  Ser  Thr  Glu  Ile  Tyr
                        420                           425                           430
         Ser  Glu  Ile  Tyr  Phe  Gly  Asn  Ser  Ile  Lys  Gly  Tyr  Glu  Asp  Phe  Ala
                             435                           440                           445
         Val  Ile  Ser  Pro  Ile  Leu  Gly  Ser  Phe  Asn  Ala  Gly  Ala  Thr  Phe  Gly
                   450                           455                           460
         Arg  Pro  Thr  Gly  Asn  Phe  Asn  Ile  Lys  Lys  Lys  Asn  Gln  Leu  Gln  Lys
         465                           470                           475                           480
         Glu  Ile  Val  His  His  Tyr  Asn  Asn  Tyr  Met  Asn  Glu  Asn  Asp  Leu  Glu
                                  485                           490                           495
         Ile  Ser  Gln  Leu  Asn  Glu  Ala  Pro  Leu  Asn  Ser  Arg  Asn  Val  Asn  Ile
                             500                           505                           510
         Leu  Asn  Asn  Asn  Arg  Ile  Tyr  Asn  Thr  Cys  Leu  Asn  Leu  Asn  Leu  Pro
                        515                           520                           525
         Lys  Ser  Asp  Ile  Asp  Ile  Asn  Asp  Ile  Phe  Ile  Gly  Ala  Thr  Phe  Asn
              530                           535                           540
         Lys  Leu  Tyr  Leu  Tyr  Ser  Glu  Lys  His  Asp  Ser  Arg  Ile  Val  Phe  Val
         545                           550                           555                           560
         Ser  Asn  Ser  Met  Phe  Asn  Tyr  Glu  Phe  Gly  Ser  Glu  Leu  Tyr  Lys  Phe
                                  565                           570                           575
         Leu  Arg  Glu  Ile  Ser  Phe  Glu  Lys  Thr  Lys  Phe  Ile  Gln  Pro  Ile  Thr
                             580                           585                           590
         Glu  Glu  Gly  Ile  Asp  Ser  Leu  Pro  Phe  Cys  Pro  Arg  Ile  Ile  Tyr  Lys
                        595                           600                           605
         Asn  Ile  Ile  Leu  Lys  Pro  Ala  Thr  Trp  Lys  Ile  Asn  Ser  Glu  Met  Phe
              610                           615                           620
         Ser  Glu  Thr  Glu  Asn  Trp  Leu  Asn  Arg  Phe  Ala  Thr  Ile  Arg  Lys  Trp
         625                           630                           635                           640
         His  Ile  Pro  Lys  Asp  Val  Ile  Ile  Ala  Phe  Gly  Asp  Asn  Arg  Leu  Leu
                                  645                           650                           655
         Leu  Asn  Leu  Leu  Asn  Asp  Lys  His  Leu  Ile  Ile  Leu  Lys  Lys  Glu  Leu
                             660                           665                           670
         Lys  Lys  His  Gly  Arg  Ile  Arg  Ile  Leu  Glu  Ser  Phe  Ile  Asn  Glu  Ser
                        675                           680                           685
         Asn  Asn  Glu  Arg  Met  Leu  Glu  Ile  Val  Thr  Pro  Leu  Tyr  Lys  Lys  Thr
              690                           695                           700
         Ser  Leu  Lys  Glu  Gln  Ser  Phe  Ile  Ile  Pro  Lys  Asn  Arg  Asn  Lys  His
         705                           710                           715                           720
         Phe  Asn  Asn  Leu  Lys  Asp  Trp  Phe  Ser  Ile  His  Leu  Ser  Ile  Pro  Lys
                                  725                           730                           735
         Thr  Tyr  Gln  Asp  Asn  Phe  Ile  Gln  Asp  Tyr  Leu  Leu  Pro  Phe  Ile  Thr
                             740                           745                           750
```

```
Glu  Leu  Lys  Val  Asn  Asn  Phe  Ile  Asn  Lys  Phe  Phe  Tyr  Ile  Lys  Phe
          755                 760                           765

Lys  Glu  Asp  Glu  Asp  Phe  Ile  Lys  Leu  Arg  Leu  Leu  Arg  Glu  Asp  Glu
          770                 775                      780

Asp  Tyr  Ser  Gln  Ile  Tyr  Ser  Phe  Ile  Lys  Asn  Trp  Lys  Asp  Tyr  Cys
785                      790                 795                           800

Leu  Leu  Asn  Ser  Glu  Leu  Tyr  Asp  Tyr  Ser  Ile  Val  Asp  Tyr  Val  Pro
               805                      810                      815

Glu  Val  Tyr  Arg  Tyr  Gly  Gly  Pro  His  Val  Ile  Glu  Asp  Ile  Glu  Asn
               820                 825                           830

Phe  Phe  Met  Tyr  Asp  Ser  Leu  Leu  Asp  Ser  Ile  Asn  Ile  Ile  Gln  Ser
          835                      840                      845

Glu  Phe  Lys  Ile  Pro  Lys  Glu  Phe  Ile  Val  Ala  Ile  Ser  Ile  Asp  Phe
     850                      855                      860

Leu  Leu  Asp  Tyr  Leu  Glu  Ile  Asn  Lys  Ser  Glu  Lys  Glu  Glu  Ile  Leu
865                      870                 875                           880

Ile  Asn  Asn  Ala  Glu  Asp  Leu  Tyr  Arg  Ser  Asn  Asp  Ile  Arg  Glu  Tyr
               885                      890                      895

Lys  Asn  Leu  Leu  Ala  Lys  Leu  Thr  Asn  Pro  Lys  Asn  Asp  Tyr  Glu  Ile
               900                 905                           910

Leu  Lys  Lys  Glu  Phe  Pro  Asn  Leu  His  Glu  Phe  Leu  Phe  Asn  Lys  Ile
          915                      920                      925

Ser  Ile  Leu  Glu  Asn  Leu  Lys  Lys  Thr  Leu  Gln  Lys  Ser  Leu  Tyr  Thr
          930                      935                 940

Ser  Arg  Ser  Arg  Ile  Ile  Gly  Ser  Phe  Ile  His  Met  Arg  Cys  Asn  Arg
945                      950                      955                      960

Ile  Phe  Gly  Ile  Asn  Pro  Glu  Lys  Glu  Lys  Phe  Val  Leu  Ser  Ile  Phe
               965                      970                      975

Asn  Glu  Ile  Thr  Lys  Thr  Lys  Lys  Tyr  Trp  Asp  Gly  Cys  Asp
               980                      985                 990
```

( 2 ) INFORMATION FOR SEQ ID NO:21:

( i ) SEQUENCE CHARACTERISTICS:
        ( A ) LENGTH: 455 amino acids
        ( B ) TYPE: amino acid
        ( D ) TOPOLOGY: linear ( x i ) SEQUENCE DESCRIPTION: SEQ ID NO:21:

```
Leu  Ala  Val  Leu  Tyr  Thr  Cys  Val  Val  Ile  Glu  Tyr  Ser  Val  Leu  Ile
1              5                        10                       15

Leu  Lys  Lys  Lys  Asn  Leu  Phe  Tyr  Leu  Phe  Leu  Met  Lys  Leu  Gln  Lys
               20                 25                      30

Leu  Lys  Asn  Ile  Gly  Met  Val  Val  Ile  Asn  Ile  Asn  Asn  Ile  Lys  Lys
          35                 40                      45

Ile  Leu  Glu  Asn  Lys  Ile  Thr  Phe  Leu  Ser  Asp  Ile  Glu  Lys  Ala  Thr
     50                      55                 60

Tyr  Ile  Ile  Glu  Asn  Gln  Ser  Glu  Tyr  Trp  Asp  Pro  Tyr  Thr  Leu  Ser
65                      70                 75                            80

His  Gly  Tyr  Pro  Gly  Ile  Ile  Leu  Phe  Leu  Ser  Ala  Ser  Glu  Lys  Val
               85                      90                      95

Phe  His  Lys  Asp  Leu  Glu  Lys  Val  Ile  His  Gln  Tyr  Ile  Arg  Lys  Leu
               100                     105                     110

Gly  Pro  Tyr  Leu  Glu  Ser  Gly  Ile  Asp  Gly  Phe  Ser  Leu  Phe  Ser  Gly
               115                     120                     125

Leu  Ser  Gly  Ile  Gly  Phe  Ala  Leu  Asp  Ile  Ala  Ser  Asp  Lys  Gln  Tyr
```

|     |     |     |     | 130 |     |     |     |     | 135 |     |     |     |     | 140 |     |
|---|---|---|---|---|---|---|---|---|---|---|---|---|---|---|---|

Ser Tyr Gln Ser Ile Leu Glu Gln Ile Asp Asn Leu Leu Val Gln Tyr
145                     150                     155                     160

Val Phe Asp Phe Leu Asn Asn Asp Ala Leu Glu Val Thr Pro Thr Asn
                165                     170                     175

Tyr Asp Ile Ile Gln Gly Phe Ser Gly Val Gly Arg Tyr Leu Leu Asn
            180                     185                     190

Arg Ile Ser Tyr Asn Tyr Asn Ala Lys Lys Ala Leu Lys His Ile Leu
        195                     200                     205

Asn Tyr Phe Lys Thr Ile His Tyr Ser Lys Asp Asn Trp Leu Val Ser
    210                     215                     220

Asn Glu His Gln Phe Leu Asp Ile Asp Lys Gln Asn Phe Pro Ser Gly
225                     230                     235                     240

Asn Ile Asn Leu Gly Leu Ala His Gly Ile Leu Gly Pro Leu Ser Leu
                245                     250                     255

Thr Ala Leu Ser Lys Met Asn Gly Ile Glu Ile Glu Gly His Glu Glu
            260                     265                     270

Phe Leu Gln Asp Phe Thr Ser Phe Leu Leu Lys Pro Glu Phe Lys Asn
        275                     280                     285

Asn Asn Glu Trp Phe Asp Arg Tyr Asp Ile Leu Glu Asn Tyr Ile Pro
    290                     295                     300

Asn Tyr Ser Val Arg Asn Gly Trp Cys Tyr Gly Asp Thr Gly Ile Met
305                     310                     315                     320

Asn Thr Leu Leu Leu Ser Gly Lys Ala Leu Asn Asn Glu Gly Leu Ile
                325                     330                     335

Lys Met Ser Lys Asn Ile Leu Ile Asn Ile Ile Asp Lys Asn Asn Asp
            340                     345                     350

Asp Leu Ile Ser Pro Thr Phe Cys His Gly Leu Ala Ser His Leu Thr
        355                     360                     365

Ile Ile His Gln Ala Asn Lys Phe Phe Asn Leu Ser Gln Val Ser Thr
    370                     375                     380

Tyr Ile Asp Thr Ile Val Arg Lys Ile Ile Ser His Tyr Ser Glu Glu
385                     390                     395                     400

Ser Ser Phe Met Phe Gln Asp Ile Glu Tyr Ser Tyr Gly Gln Lys Ile
                405                     410                     415

Tyr Lys Asn Lys Val Gly Ile Leu Glu Gly Glu Leu Gly Val Leu Leu
            420                     425                     430

Ala Leu Leu Asp Tyr Ile Asp Thr Gln Asn Gln Ser Arg Lys Asn Trp
        435                     440                     445

Lys Asn Met Phe Leu Ile Thr
450                     455

( 2 ) INFORMATION FOR SEQ ID NO:22:

( i ) SEQUENCE CHARACTERISTICS:
        ( A ) LENGTH: 181 amino acids
        ( B ) TYPE: amino acid
        ( D ) TOPOLOGY: linear ( x i ) SEQUENCE DESCRIPTION: SEQ ID NO:22:

Met Tyr Gly Lys Leu Leu Ile Cys Ala Thr Ala Ser Ile Asn Val Ile
1               5                       10                      15

Asn Ile Asn His Tyr Ile Val Glu Leu Lys Gln His Phe Asp Glu Val
            20                      25                      30

Asn Ile Leu Phe Ser Pro Ser Ser Lys Asn Phe Ile Asn Thr Asp Val
        35                      40                      45

```
Leu Lys Leu Phe Cys Asp Asn Leu Tyr Asp Glu Ile Lys Asp Pro Leu
    50                  55                  60
Leu Asn His Ile Asn Ile Val Glu Asn His Glu Tyr Ile Leu Val Leu
65                  70                  75                  80
Pro Ala Ser Ala Asn Thr Ile Asn Lys Ile Ala Asn Gly Ile Cys Asp
                85                  90                  95
Asn Leu Leu Thr Thr Val Cys Leu Thr Gly Tyr Gln Lys Leu Phe Ile
            100                 105                 110
Phe Pro Asn Met Asn Ile Arg Met Trp Gly Asn Pro Phe Leu Gln Lys
        115                 120                 125
Asn Ile Asp Leu Leu Lys Asn Asn Asp Val Lys Val Tyr Ser Pro Asp
    130                 135                 140
Met Asn Lys Ser Phe Glu Ile Ser Ser Gly Arg Tyr Lys Asn Asn Ile
145                 150                 155                 160
Thr Met Pro Asn Ile Glu Asn Val Leu Asn Phe Val Leu Asn Asn Glu
                165                 170                 175
Lys Arg Pro Leu Asp
            180
```

(2) INFORMATION FOR SEQ ID NO:23:

(i) SEQUENCE CHARACTERISTICS:
      (A) LENGTH: 205 amino acids
      (B) TYPE: amino acid
      (D) TOPOLOGY: linear (xi) SEQUENCE DESCRIPTION: SEQ ID NO:23:

```
Met Ile Ser Ile Asn Ile Val Gly Glu Val Asp Ser Ile Leu Ile Glu
1               5                   10                  15
Ser Ile Leu Glu Leu Asp Arg Arg Ile Thr Ile Asn Ser Ser Asn Ile
            20                  25                  30
Asp Pro Asn Phe Ile Ile Val Tyr Glu Lys Phe Asp Glu Tyr Tyr Thr
        35                  40                  45
Phe Leu Lys Glu Phe Ile Gly Lys Ile Pro Ile Val Ile Ile Thr Gly
    50                  55                  60
Asn Thr Ser Tyr Ser Arg Lys Cys Tyr Phe Tyr Ser Leu Gly Ile Asp
65                  70                  75                  80
Leu Tyr Ile Ile Lys Asn Asn Glu Ser Lys Ser Leu Ile Leu Cys Arg
                85                  90                  95
Ile Leu Asn Glu Ile Lys Lys Tyr Ile Lys Tyr Val Asn Asp Asp Phe
            100                 105                 110
Ile Asp Phe Glu Asn His Gln Phe Val Phe Asn Asn Tyr Leu Val Asn
        115                 120                 125
Leu Ser Asn Ile Glu Leu Lys Ile Leu Arg Cys Leu Tyr Ile Asn Leu
    130                 135                 140
Gly Arg Tyr Val Ser Lys Glu Glu Leu Lys Lys Gly Val Trp Asp Thr
145                 150                 155                 160
Glu Asp Phe Val Asp Ser Asn Thr Ile Asn Val Tyr Ile His Arg Leu
                165                 170                 175
Arg Asp Ser Leu Lys Asn Cys Lys Glu Ile Glu Ile Ile Asn Glu Arg
            180                 185                 190
Lys Leu Gly Tyr Lys Ile Leu Ile Arg Lys Asp Leu Cys
        195                 200                 205
```

(2) INFORMATION FOR SEQ ID NO:24:

( i ) SEQUENCE CHARACTERISTICS:
   ( A ) LENGTH: 461 amino acids
   ( B ) TYPE: amino acid
   ( D ) TOPOLOGY: linear ( x i ) SEQUENCE DESCRIPTION: SEQ ID NO:24:

| Met | Asn | Lys | Phe | Lys | Phe | Phe | Ile | Val | Phe | Leu | Ile | Leu | Ser | Leu | Val |
|---|---|---|---|---|---|---|---|---|---|---|---|---|---|---|---|
| 1 | | | | 5 | | | | | 10 | | | | | 15 | |
| Phe | Leu | Gln | Asn | Glu | Tyr | Ala | Phe | Gly | Ser | Ser | Leu | Asn | Glu | Glu | Leu |
| | | | 20 | | | | | 25 | | | | | 30 | | |
| Ser | Tyr | Tyr | Ser | Val | Glu | Tyr | Asp | Asn | Ala | Lys | Thr | Phe | Lys | Glu | Ser |
| | | 35 | | | | | 40 | | | | | 45 | | | |
| Ile | Lys | Gln | Lys | Asn | Ile | Glu | Leu | Thr | Tyr | Lys | Ile | Pro | Glu | Leu | His |
| | 50 | | | | | 55 | | | | | 60 | | | | |
| Thr | Ala | Gln | Ile | Lys | Thr | Ser | Lys | Ser | Lys | Leu | Asn | Ser | Leu | Ile | Lys |
| 65 | | | | | 70 | | | | | 75 | | | | | 80 |
| Ser | Asn | Lys | Asn | Val | Lys | Phe | Val | Asn | Pro | Thr | Cys | Ser | Thr | Cys | Val |
| | | | | 85 | | | | | 90 | | | | | 95 | |
| Val | Glu | Lys | Ser | Val | Lys | Thr | Gly | Lys | Asn | Leu | Asn | Asn | Lys | Lys | Asn |
| | | | 100 | | | | | 105 | | | | | 110 | | |
| Gly | Ser | His | Asp | Leu | Phe | Asp | Arg | Gln | Trp | Asp | Met | Arg | Lys | Ile | Thr |
| | | 115 | | | | | 120 | | | | | 125 | | | |
| Asn | Glu | Gly | Lys | Ser | Tyr | Lys | Leu | Ser | Pro | Asp | Arg | Lys | Lys | Ala | Lys |
| | 130 | | | | | 135 | | | | | 140 | | | | |
| Val | Ala | Leu | Val | Asp | Ser | Gly | Val | Asn | Ser | Ser | His | Thr | Asp | Leu | Lys |
| 145 | | | | | 150 | | | | | 155 | | | | | 160 |
| Ser | Ile | Asn | Lys | Ile | Val | Asn | Glu | Val | Pro | Lys | Asn | Gly | Phe | Arg | Gly |
| | | | | 165 | | | | | 170 | | | | | 175 | |
| Ser | Glu | Asn | Asp | Glu | Ser | Gly | Asn | Lys | Asn | Phe | Glu | Glu | Asp | Lys | Leu |
| | | | 180 | | | | | 185 | | | | | 190 | | |
| Asn | His | Gly | Thr | Leu | Val | Ala | Gly | Gln | Ile | Gly | Ala | Asn | Gly | Asn | Leu |
| | | | | 195 | | | | | 200 | | | | | 205 | |
| Lys | Gly | Val | Asn | Pro | Gly | Val | Glu | Met | Asn | Val | Tyr | Arg | Val | Phe | Gly |
| | 210 | | | | | 215 | | | | | 220 | | | | |
| Ser | Lys | Lys | Ser | Glu | Met | Leu | Trp | Val | Ser | Lys | Gly | Ile | Ile | Asp | Ala |
| 225 | | | | | 230 | | | | | 235 | | | | | 240 |
| Ala | Asn | Asp | Asp | Asn | Asp | Val | Ile | Asn | Val | Ser | Leu | Gly | Asn | Tyr | Leu |
| | | | | 245 | | | | | 250 | | | | | 255 | |
| Ile | Lys | Asp | Asn | Gln | Asn | Lys | Lys | Lys | Leu | Arg | Asp | Asp | Glu | Lys | Val |
| | | | 260 | | | | | 265 | | | | | 270 | | |
| Asp | Tyr | Asp | Ala | Leu | Gln | Lys | Ala | Ile | Asn | Tyr | Ala | Gln | Lys | Lys | Gly |
| | | 275 | | | | | 280 | | | | | 285 | | | |
| Ser | Ile | Val | Val | Ala | Ala | Val | Gly | Asn | Asp | Gly | Ile | Asn | Val | Lys | Lys |
| | 290 | | | | | 295 | | | | | 300 | | | | |
| Val | Lys | Glu | Ile | Asn | Lys | Lys | Arg | Asn | Leu | Asn | Ser | Lys | Thr | Ser | Lys |
| 305 | | | | | 310 | | | | | 315 | | | | | 320 |
| Lys | Val | Tyr | Asp | Ser | Pro | Ala | Asn | Leu | Asn | Asn | Val | Met | Thr | Val | Gly |
| | | | | 325 | | | | | 330 | | | | | 335 | |
| Ser | Ile | Asp | Asp | Asn | Asp | Tyr | Ile | Ser | Glu | Phe | Ser | Asn | Tyr | Gly | Asn |
| | | | 340 | | | | | 345 | | | | | 350 | | |
| Asn | Phe | Ile | Asp | Leu | Met | Thr | Ile | Gly | Gly | Ser | Tyr | Lys | Leu | Leu | Asp |
| | | 355 | | | | | 360 | | | | | 365 | | | |
| Lys | Tyr | Gly | Lys | Asp | Ala | Trp | Leu | Glu | Lys | Gly | Tyr | Met | Gln | Lys | Gln |
| | 370 | | | | | 375 | | | | | 380 | | | | |
| Ser | Val | Leu | Ser | Thr | Ser | Ser | Asn | Gly | Arg | Tyr | Ile | Tyr | Gln | Ser | Gly |

```
                385                 390                 395                 400
            Thr Ser Leu Ala Ala Pro Lys Val Ser Gly Ala Leu Ala Leu Glu Ile
                            405                 410                 415
            Asp Lys Tyr Gln Leu Lys Asp Gln Pro Glu Thr Ala Ile Glu Leu Phe
                        420                 425                 430
            Lys Lys Lys Gly Ile Glu Lys Glu Lys Tyr Met Asp Lys Lys His Tyr
                    435                 440                 445
            Gly Asn Gly Lys Leu Asp Val Tyr Lys Leu Leu Lys Glu
                    450                 455                 460
```

( 2 ) INFORMATION FOR SEQ ID NO:25:

( i ) SEQUENCE CHARACTERISTICS:
        ( A ) LENGTH: 41 amino acids
        ( B ) TYPE: amino acid
        ( D ) TOPOLOGY: linear ( x i ) SEQUENCE DESCRIPTION: SEQ ID NO:25:

```
            Glu Gly Lys Ser Tyr Lys Leu Ser Pro Asp Arg Lys Lys Ala Lys Val
            1               5                   10                  15
            Ala Leu Val Asp Ser Gly Val Asn Ser Ser His Thr Asp Leu Lys Ser
                        20                  25                  30
            Ile Asn Lys Ile Val Asn Glu Val Pro
                    35                  40
```

( 2 ) INFORMATION FOR SEQ ID NO:26:

( i ) SEQUENCE CHARACTERISTICS:
        ( A ) LENGTH: 41 amino acids
        ( B ) TYPE: amino acid
        ( D ) TOPOLOGY: linear ( x i ) SEQUENCE DESCRIPTION: SEQ ID NO:26:

```
            Ala Pro Ala Leu His Ser Gln Gly Tyr Thr Gly Ser Asn Val Lys Val
            1               5                   10                  15
            Ala Val Ile Asp Ser Gly Ile Asp Ser Ser His Pro Asp Leu Asn Val
                        20                  25                  30
            Arg Gly Gly Ala Ser Phe Val Pro Ser
                    35                  40
```

( 2 ) INFORMATION FOR SEQ ID NO:27:

( i ) SEQUENCE CHARACTERISTICS:
        ( A ) LENGTH: 41 amino acids
        ( B ) TYPE: amino acid
        ( D ) TOPOLOGY: linear ( x i ) SEQUENCE DESCRIPTION: SEQ ID NO:27:

```
            Ala Pro Glu Met Trp Ala Lys Gly Val Lys Gly Lys Asn Ile Lys Val
            1               5                   10                  15
            Ala Val Leu Asp Thr Gly Cys Asp Thr Ser His Pro Asp Leu Lys Asn
                        20                  25                  30
            Gln Ile Ile Gly Gly Lys Asn Phe Ser
                    35                  40
```

( 2 ) INFORMATION FOR SEQ ID NO:28:

( i ) SEQUENCE CHARACTERISTICS:
        ( A ) LENGTH: 41 amino acids
        ( B ) TYPE: amino acid
        ( D ) TOPOLOGY: linear ( x i ) SEQUENCE DESCRIPTION: SEQ ID NO:28:

```
        Gln  Ala  Pro  Gln  Ala  Trp  Asp  Ile  Ala  Glu  Gly  Ser  Gly  Ala  Lys  Ile
        1              5                        10                       15

Ala  Ile  Val  Asp  Thr  Gly  Val  Gln  Ser  Asn  His  Pro  Asp  Leu  Ala  Gly
                       20                       25                       30

Lys  Val  Val  Gly  Gly  Trp  Asp  Phe  Val
                       35                  40
```

( 2 ) INFORMATION FOR SEQ ID NO:29:

( i ) SEQUENCE CHARACTERISTICS:
        ( A ) LENGTH: 51 amino acids
        ( B ) TYPE: amino acid
        ( D ) TOPOLOGY: linear ( x i ) SEQUENCE DESCRIPTION: SEQ ID NO:29:

```
        Pro  Lys  Asn  Gly  Phe  Arg  Gly  Ser  Glu  Asn  Asp  Glu  Ser  Gly  Asn  Lys
        1              5                        10                       15

Asn  Phe  Glu  Glu  Asp  Lys  Leu  Asn  His  Gly  Thr  Leu  Val  Ala  Gly  Gln
                       20                       25                       30

Ile  Gly  Ala  Asn  Gly  Asn  Leu  Lys  Gly  Val  Asn  Pro  Gly  Val  Glu  Met
                       35                       40                       45

Asn  Val  Tyr
                  50
```

( 2 ) INFORMATION FOR SEQ ID NO:30:

( i ) SEQUENCE CHARACTERISTICS:
        ( A ) LENGTH: 51 amino acids
        ( B ) TYPE: amino acid
        ( D ) TOPOLOGY: linear ( x i ) SEQUENCE DESCRIPTION: SEQ ID NO:30:

```
        Pro  Asp  Leu  Asn  Val  Arg  Gly  Gly  Ala  Ser  Phe  Val  Pro  Ser  Glu  Thr
        1              5                        10                       15

Asn  Pro  Tyr  Gln  Asp  Gly  Ser  Ser  His  Gly  Thr  His  Val  Ala  Gly  Thr
                       20                       25                       30

Ile  Ala  Ala  Leu  Asn  Asn  Ser  Ile  Gly  Val  Leu  Gly  Val  Ser  Pro  Ser
                       35                       40                       45

Ala  Ser  Leu
                  50
```

( 2 ) INFORMATION FOR SEQ ID NO:31:

( i ) SEQUENCE CHARACTERISTICS:
        ( A ) LENGTH: 51 amino acids
        ( B ) TYPE: amino acid
        ( D ) TOPOLOGY: linear ( x i ) SEQUENCE DESCRIPTION: SEQ ID NO:31:

```
        Gln  Ile  Ile  Gly  Gly  Lys  Asn  Phe  Ser  Asp  Asp  Gly  Gly  Lys  Glu
        1              5                        10                       15

Asp  Ala  Ile  Ser  Asp  Tyr  Asn  Gly  His  Gly  Thr  His  Val  Ala  Gly  Thr
                       20                       25                       30

Ile  Ala  Ala  Asn  Asp  Ser  Asn  Gly  Gly  Ile  Ala  Gly  Val  Ala  Pro  Glu
                       35                       40                       45

Ala  Ser  Leu
                  50
```

( 2 ) INFORMATION FOR SEQ ID NO:32:

( i ) SEQUENCE CHARACTERISTICS:

(A) LENGTH: 21 amino acids
    (B) TYPE: amino acid
    (D) TOPOLOGY: linear ( x i ) SEQUENCE DESCRIPTION: SEQ ID NO:32:

Asn Gly Asn Gly His Gly Thr His Cys Ala Gly Ile Ala Ala Ala Val
1               5                   10                  15

Thr Asn Asn Ser Thr
                20

( 2 ) INFORMATION FOR SEQ ID NO:33:

( i ) SEQUENCE CHARACTERISTICS:
        (A) LENGTH: 41 amino acids
        (B) TYPE: amino acid
        (D) TOPOLOGY: linear ( x i ) SEQUENCE DESCRIPTION: SEQ ID NO:33:

Tyr Met Gln Lys Gln Ser Val Leu Ser Thr Ser Ser Asn Gly Arg Tyr
1               5                   10                  15

Ile Tyr Gln Ser Gly Thr Ser Leu Ala Ala Pro Lys Val Ser Gly Ala
                20                  25                  30

Leu Ala Leu Glu Ile Asp Lys Tyr Gln
                35              40

( 2 ) INFORMATION FOR SEQ ID NO:34:

( i ) SEQUENCE CHARACTERISTICS:
        (A) LENGTH: 41 amino acids
        (B) TYPE: amino acid
        (D) TOPOLOGY: linear ( x i ) SEQUENCE DESCRIPTION: SEQ ID NO:34:

Met Ala Pro Gly Val Ser Ile Gln Ser Thr Leu Pro Gly Gly Thr Tyr
1               5                   10                  15

Gly Ala Tyr Asn Gly Thr Ser Met Ala Thr Pro His Val Ala Gly Ala
                20                  25                  30

Ala Ala Leu Ile Leu Ser Lys His Pro
                35              40

( 2 ) INFORMATION FOR SEQ ID NO:35:

( i ) SEQUENCE CHARACTERISTICS:
        (A) LENGTH: 35 amino acids
        (B) TYPE: amino acid
        (D) TOPOLOGY: linear ( x i ) SEQUENCE DESCRIPTION: SEQ ID NO:35:

Val Ala Pro Gly Glu Asn Ile Leu Ser Thr Leu Pro Asn Lys Lys Tyr
1               5                   10                  15

Gly Lys Leu Thr Gly Thr Ser Met Ala Ala Pro His Val Ser Gly Ala
                20                  25                  30

Leu Ala Leu
        35

( 2 ) INFORMATION FOR SEQ ID NO:36:

( i ) SEQUENCE CHARACTERISTICS:
        (A) LENGTH: 5 amino acids
        (B) TYPE: amino acid
        (D) TOPOLOGY: linear ( x i ) SEQUENCE DESCRIPTION: SEQ ID NO:36:

Ile Lys Ser Tyr Glu (2) INFORMATION FOR SEQ ID NO:37:

(i) SEQUENCE CHARACTERISTICS:
        (A) LENGTH: 41 amino acids
        (B) TYPE: amino acid
        (D) TOPOLOGY: linear (xi) SEQUENCE DESCRIPTION: SEQ ID NO:37:

```
Ala Ala Pro Gly Ser Trp Ile Tyr Ser Thr Tyr Pro Thr Ser Thr Tyr
 1               5                   10                  15
Ala Ser Leu Ser Gly Thr Ser Met Ala Thr Pro His Val Ala Gly Val
            20                  25                  30
Ala Gly Leu Leu Ala Ser Gln Gly Arg
            35                  40
```

(2) INFORMATION FOR SEQ ID NO:38:

(i) SEQUENCE CHARACTERISTICS:
        (A) LENGTH: 115 amino acids
        (B) TYPE: amino acid
        (D) TOPOLOGY: linear (xi) SEQUENCE DESCRIPTION: SEQ ID NO:38:

```
Met Ile Ser Ile Asn Ile Val Gly Glu Val Asp Ser Ile Leu Ile Glu
 1               5                   10                  15
Ser Ile Leu Glu Leu Asp Arg Arg Ile Thr Ile Asn Ser Ser Asn Ile
            20                  25                  30
Asp Pro Asn Phe Ile Ile Val Tyr Glu Lys Phe Asp Glu Tyr Tyr Thr
            35                  40                  45
Phe Leu Lys Glu Phe Ile Gly Lys Ile Pro Ile Val Ile Ile Thr Gly
    50                  55                  60
Asn Thr Ser Tyr Ser Arg Lys Cys Tyr Phe Tyr Ser Leu Gly Ile Asp
65                  70                  75                  80
Leu Tyr Ile Ile Lys Asn Asn Glu Ser Lys Ser Leu Ile Leu Cys Arg
                85                  90                  95
Ile Leu Asn Glu Ile Lys Lys Tyr Ile Lys Tyr Val Asn Asp Asp Phe
            100                 105                 110
Ile Asp Phe
        115
```

(2) INFORMATION FOR SEQ ID NO:39:

(i) SEQUENCE CHARACTERISTICS:
        (A) LENGTH: 93 amino acids
        (B) TYPE: amino acid
        (D) TOPOLOGY: linear (xi) SEQUENCE DESCRIPTION: SEQ ID NO:39:

```
Val Leu Glu Gln Asn Gly Phe Gln Pro Val Glu Ala Glu Asp Tyr Asp
 1               5                   10                  15
Ser Ala Val Asn Gln Leu Asn Glu Pro Trp Pro Asp Leu Ile Leu Leu
            20                  25                  30
Asp Trp Met Leu Pro Gly Gly Ser Gly Ile Gln Phe Ile Lys His Leu
            35                  40                  45
Lys Arg Glu Ser Met Thr Arg Asp Ile Pro Val Val Met Leu Thr Ala
        50                  55                  60
Arg Gly Glu Glu Glu Asp Arg Val Arg Gly Leu Glu Thr Gly Ala Asp
65                  70                  75                  80
```

Asp  Tyr  Ile  Thr  Lys  Pro  Phe  Ser  Pro  Lys  Glu  Leu  Val
                                    85                       90

(2) INFORMATION FOR SEQ ID NO:40:

(i) SEQUENCE CHARACTERISTICS:
        (A) LENGTH: 116 amino acids
        (B) TYPE: amino acid
        (D) TOPOLOGY: linear (xi) SEQUENCE DESCRIPTION: SEQ ID NO:40:

Ala  Arg  Ile  Lys  Ala  Val  Met  Arg  Arg  Ile  Ser  Pro  Met  Ala  Val  Glu
        1                   5                        10                       15

Glu  Val  Ile  Glu  Met  Gln  Gly  Leu  Ser  Leu  Asp  Pro  Thr  Ser  His  Arg
                        20                      25                       30

Val  Met  Ala  Gly  Glu  Glu  Pro  Leu  Glu  Met  Gly  Pro  Thr  Glu  Phe  Lys
                   35                      40                       45

Leu  Leu  His  Phe  Phe  Met  Thr  His  Pro  Glu  Arg  Val  Tyr  Ser  Arg  Glu
                   50                      55                       60

Gln  Leu  Leu  Asn  His  Val  Trp  Gly  Thr  Asn  Val  Tyr  Val  Glu  Asp  Arg
        65                      70                       75                       80

Thr  Val  Asp  Val  His  Ile  Arg  Arg  Leu  Arg  Lys  Ala  Leu  Glu  Pro  Gly
                        85                      90                       95

Gly  His  Asp  Arg  Met  Val  Gln  Thr  Val  Arg  Gly  Thr  Gly  Tyr  Arg  Phe
                        100                     105                      110

Ser  Thr  Arg  Phe
                   115

(2) INFORMATION FOR SEQ ID NO:41:

(i) SEQUENCE CHARACTERISTICS:
        (A) LENGTH: 76 amino acids
        (B) TYPE: amino acid
        (D) TOPOLOGY: linear (xi) SEQUENCE DESCRIPTION: SEQ ID NO:41:

Glu  Asn  His  Gln  Phe  Val  Phe  Asn  Asn  Tyr  Leu  Val  Asn  Leu  Ser  Asn  Ile
        1                   5                        10                       15

Glu  Leu  Lys  Ile  Leu  Arg  Cys  Leu  Tyr  Ile  Asn  Leu  Gly  Arg  Tyr  Val
                        20                      25                       30

Ser  Lys  Glu  Glu  Leu  Lys  Lys  Gly  Val  Trp  Asp  Thr  Glu  Asp  Phe  Val
                   35                      40                       45

Asp  Ser  Asn  Thr  Ile  Asn  Val  Tyr  Ile  His  Arg  Leu  Arg  Asp  Ser  Leu
        50                      55                       60                       65

Lys  Asn  Cys  Lys  Glu  Ile  Glu  Ile  Ile  Asn  Glu
                        70                      75

(2) INFORMATION FOR SEQ ID NO:42:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO:42:

Arg  Lys  Leu  Gly  Tyr  Lys  Ile  Leu  Ile  Arg  Lys  Asp  Leu  Cys
        1                   5                        10